US005885815A

United States Patent [19]
Sassanfar et al.

[11] Patent Number: 5,885,815
[45] Date of Patent: Mar. 23, 1999

[54] CANDIDA ISOLEUCYL-TRNA SYNTHETASE PROTEINS, NUCLEIC ACIDS AND STRAINS COMPRISING SAME

[75] Inventors: Mandana Sassanfar, Dedham, Mass.; Christoph Kaufmann, Buechenbeuren, Germany; Paul L. Gallant, Dedham, Mass.; Janice E. Kranz, Jamaica Plain; Fariba Houman, Belmont, both of Mass.

[73] Assignee: Cubist Pharmaceuticals, Inc., Cambridge, Mass.

[21] Appl. No.: 742,026

[22] Filed: Nov. 1, 1996

[51] Int. Cl.$^6$ .............................. C12N 9/00; C12N 1/14; C12N 15/00; C07H 21/04

[52] U.S. Cl. ............... 435/183; 435/252.3; 435/254.11; 435/320.1; 435/325; 536/23.2; 536/23.4

[58] Field of Search ................................ 435/183, 252.3, 435/254.11, 320.1, 325; 536/23.2, 23.4

[56] References Cited

U.S. PATENT DOCUMENTS

| | | | |
|---|---|---|---|
| 4,713,337 | 12/1987 | Jasin et al. | 435/172.3 |
| 4,788,148 | 11/1988 | Nilsson et al. | 435/320 |
| 4,952,501 | 8/1990 | Jasin et al. | 435/69.2 |
| 4,963,487 | 10/1990 | Schimmel et al. | 435/172.3 |
| 5,370,995 | 12/1994 | Hennecke et al. | 435/69.1 |
| 5,561,054 | 10/1996 | Kron et al. | 435/69.1 |

FOREIGN PATENT DOCUMENTS

WO 95/09927   4/1995   WIPO.

OTHER PUBLICATIONS

Webster, T., et al., "Specific Sequence Homology and Three–Dimensional Structure of an Aminoacyl Transfer RNA Synthetase," *Science* 266:1315–1317, Dec. 1984.

Edwards, H., et al., "An *E. coli* Aminoacyl–tRNA Synthetase Can Substitute for Yeast Mitochondrial Enzyme Function In Vivo," *Cell*, 51:643–649 (1987).

Englisch, U., et al., "Structure of the Yeast Isoleucyl–tRNA Synthetase Gene (ILS1)," *Biol. Chem. Hoppe–Seyler* 368:971–979, Aug. 1987.

Martindale, D.W., et al., "Isolation and complete sequence of the yeast isoleucyl–tRNA synthetase gene (ILS1)," *Current Genetics* 15:99–106 (1989).

Jenal, U., et al., "Isoleucyl–tRNA Synthetase of *Methanobacterium thermautotrophicum* Marburg," *The Journal of Biological Chemistry* 266(16):10570–10577, Jun. 5, 1991.

Shiba, K. and Schimmel, P., "Functional Assembly of a Randomly Cleaved Protein," *Proc. Natl. Acad. Sci USA*, 89:1880–1884 (1992).

Racher, K.I., et al., "Expression and Characterization of a Recombinant Yeast Isoleucyl–tRNA Synthetase," *The Journal of Biological Chemistry*, 266(26):17158–17164 (1991).

Iaccarino, M. and Berg, P., "Isoleucine Auxotrophy as a Consequence of a Mutationally Altered Isoleucyl–Transfer Ribonucleic Acid Synthetase," *J. Bacteriol.*, 105:527–537 (1970).

Walter, R.D. and Kuhlow, F., "Parasite–Specific Interaction of N–[4–(4'Nitroanilino)–Phenyl]–S–(β–Carboxyethyl)– Dithiocarbamic Acid–Ester with Arginyl–tRNA–Synthetase from *Dirofiliaria immitis*," *Trop. Med. Parasit.*, 36:230–232 (1985).

Chalker, A.F., et al., "Analysis and Toxic Overexpression in *Escherichia coli* of a Staphylococcal Gene Encoding Isoleucyl–tRNA Synthetase," *Gene*, 141:103–108 (1994).

Hughes, J. and Mellows, G., "Interaction of Pseudomonic Acid A with *Escherichia coli* B Isoleucyl–tRNA Synthetase," *Biochem J.*, 191:209–219 (1980).

von der Haar, F. et al, "Target Directed Drug Synthesis: The Aminoacyl–tRNA Synthetases as Possible Targets," *Angew. Chen. Int. Ed.*, 20(3):217–223 (1981).

Weygand–Duraševič, I. "Yeast Seryl–tRNA Synthetase Expressed in *Escherichia coli* Recognizes Bacterial Serine–Specific tRNAs in vivo," *Eur. J. Biochem.*, 214:869–877 (1993).

Printout of a computer record of parts of a poster presented at Cap d'Agde, France, May 30–Jun. 4, 1993, 15th International tRNA Workshop, Société Francaise de Biochimie et Biologie Moléculaire.

Meinnel, T., et al., "Aminoacyl–tRNA Synthetases: Occurrence, Structure, and Function." In tRNA: *Structure, Biosynthesis, and Function*, Söll, D. and RajBhandary, U., eds. (Washington, DC: American Society for Microbiology), pp. 251–300 (1995).

(List continued on next page.)

*Primary Examiner*—Robert A. Wax
*Assistant Examiner*—Lisa J. Hobbs
*Attorney, Agent, or Firm*—Hamilton, Brook, Smith & Reynolds, P.C.

[57] ABSTRACT

The present invention relates to isolated and/or recombinant nucleic acids which encode Candida isoleucyl-tRNA synthetases, portions thereof, or fusion proteins comprising a Candida isoleucyl-tRNA synthetase or portion thereof. Also disclosed are constructs comprising the nucleic acids of the present invention, host cells comprising a recombinant nucleic acid or construct, and methods of producing a Candida isoleucyl-tRNA synthetase, portion thereof, or fusion protein comprising same. Also described are tester strains, which are cells engineered to rely on the function of a Candida isoleucyl-tRNA synthetase or functional fragment thereof encoded by an introduced cloned gene, and which can be used in a method of detecting an inhibitor of Candida isoleucyl-tRNA synthetase function.

The invention further relates to isolated and/or recombinant Candida isoleucyl-tRNA synthetases, portions thereof, or fusion proteins comprising a Candida isoleucyl-tRNA synthetase or portion thereof, methods of use of these polypeptides in an assay to identify inhibitors of Candida isoleucyl-tRNA synthetase function, and antibodies reactive with Candida isoleucyl-tRNA synthetases.

51 Claims, 6 Drawing Sheets

OTHER PUBLICATIONS

Shepard, A., et al., "RNA Binding Determinant in Some Class I tRNA Synthetases Identified by Alignment–Guided Mutagenesis," *Proc. Natl. Acad. Sci. USA*, 89:9964–9968 (1992).

Jasin, M. and Schimmel, P., "Deletion of an Essential Gene in *Escherichia coli* by Site–Specific Recombination with Linear DNA Fragments," *J. Bacteriol.*, 159(2):783–786 (1984).

Edwards, H. and Schimmel, P., "A Bacterial Amber Suppressor in *Saccharomyces cerevisiae* Is Selectively Recognized by a Bacterial Aminoacyl–tRNA Synthetase," *Molecular and Cellular Biology*, 10(4):1633–1641 (1990).

Shiba, K., et al., "Isolation of Higher Eukaryote Aminoacyl–tRNA Synthetase Genes by and Alignment–Guided Cross–Species PCR: Application to Human Isoleucine tRNA Synthetase," [From *Programme and Abstracts*, p. F.46], 15th International tRNA Workshop, Société Francaise de Biochimie et Biologie Moléculaire, Cap d'Agde, France, May 30–Jun. 4 (1993), Abstract No. 364.

Kaufmann, C., "Cloning, Expression and Characterization of the Isoleucyl–tRNA Synthetase of *Candida albicans*," Thesis, Naturwissenschaftliche Fakultät, Universität Witten/Herdecke, 1995.

Ohama, Takeshi et al., "Non–Universal Decoding of the Leucine Codon CUG is Several *Candida Species*," *Nucleic Acids Research*, 21(17):4039–4045 (1993).

Hughes, J., et al., "Inhibition of Isoleucyl–Transfer Ribonucleic Acid Synthetase in *Escherichia coli* by Pseudomonic Acid," *Biochem. J.*, 176:305–318 (1978), Great Britain.

Leuker, Christoph E. and Ernst, Joachim F., "Toxicity of a Heterologous Leucyl–tRNA (anticodon CAG) in the Pathogen *Candida albicans*: In Vivo Evidence for Non–Standard Decoding of CUG Codons," *Mol. Gen. Genet.*, 245:212–217 (1994).

Houman, F., et al., "Cloning, Expression and Characterization of Isoleucyl–tRNA Synthetase from *Candida albicans*," poster presented at Gordon Research Conference on Cellular and Molecular Mycology, Holderness School, Plymouth, New Hampshire, Jun. 16–17, 1996.

Csank, C., et al., "Isoleucyl–tRNA Synthetase from the Ciliated Protozoan *Tetrahymena thermophila*," *The Journal of Biological Chemistry* 267(7):4592–4599, Mar. 5, 1992.

Kim, Sunghoon et al., "Diversified Sequences of Peptide Epitope for Same–RNA Recognition," *Proc. Natl. Acad. Sci. USA*, 90:10046–10050 (1993).

Tzagoloff, Alexander and Shtanko, Andrey, "Mitochondrial and Cytoplasmic Isoleucyl–, Glutamyl–and Arginyl–tRNA Synthetases of Yeast are Encoded by Separate Genes," *Eur. J. Biochem.*, 230:582–586 (1995).

Capobianco, John O., et al., "Anti–Candida Activity of Cispentacin: The Active Transport by Amino Acid Permeases and Possible Mechanisms of Action," *Biochemical and Biophysical Research Communications* 190(3):1037–1044 (1993).

Shiba, Kiyotaka. et al., "Human Cytoplasmic Isoleucyl–tRNA Synthetase: Selective Divergence of the Anticodon–Binding Domain and Acquisition of a New Structural Unit," *Proc. Natl. Acad. Sci. USA*, 91:7435–7439 (1994).

Orlova, V.S., et al., "Effect of Aerobic and Anaerobic Conditions on Chemical Composition and Enzyme Activity of Buds and Mother Cells of *Candida utilis*," *Prikladnaya Biokhimiya i Mikrobiologiya* 13(2):260–264 (1977).

Vinogradov, B.D., et al., "Activation of L–Amino Acids By a Preparation of Aminoacyl–tRNA Synthetases From the Yeast *Candida utilis*," *Prikladnaya Biokhimiya i Mikrobiologiya* 11(3):378–381 (1975).

Ogawa, Kazuko, et al., "Anticodon Loop Structure of *Torulopsis utilis* tRNA$^{Val}$ and Valine Acceptance," *Journal of Advanced Science* 5(2):43–49 (1993).

Murasugi, A. and Hayashi, H., "Purification and Properties of Leucyl–tRNA Synthetase from *Candida utilis*," *Eur. J. Biochem.* 57:169–175 (1975).

Suzuki, Tsutomu, et al., "Characterization of Serine and Leucine tRNAs in an Asporogenic Yeast *Candida cylindracea* and Evolutionary Implications of Genes for tRNA$^{Ser}$-CAG Responsible for Translation of a Non–Universal Genetic Code,"*Nucleic Acids Research* 22(2):115–123 (1994).

CANDIDA ISOLEUCYL-TRNA SYNTHETASE PROTEINS, NUCLEIC ACIDS AND STRAINS COMPRISING SAME

BACKGROUND OF THE INVENTION

*Candida albicans* is an opportunistic pathogen and the most common fungus causing systemic infections in man including both bloodstream infections in hospital immunocompromised patients and vaginal infections (for review, see: Mandell, G. L.; Bennett, J. E.; and Dolin, R. (Eds), *Principles and Practice of Infectious Disease*, 4th ed., Churchill Livingston: New York, 1995; Vol 2, Chapter 237). The increasing use of immunosuppressive therapy for malignancy and transplantation, the increase of intensive care patients receiving broad spectrum antibiotic therapy, and the AIDS epidemic have greatly increased the number of patients susceptible to opportunistic infections caused by *C. albicans*. In particular, infections due to Candida increased by almost 500% over the decade of the 1980s and continue to rise in the 1990s, becoming the fourth most common blood-stream pathogen (see: Pfaller, M. A. *Journal of Hospital Infection* 30 suppl. 329–38 1995). It has been reported that 90% of AIDS patients have some type of Candida infection. *C. albicans* can invade the kidneys, heart, liver, lungs, spleen, brain and eyes. These infections are difficult to detect and can lead to death.

A limited number of antifungal agents are available for the treatment for *C. albicans* infections. Amphotericin B, the mainstay of antifungal therapy, has limited clinical utility in treating Candida infection due to its associated toxicities and requirement for intravenous administration. Flucytosine too is limited due to its bone marrow toxicity and to the appearance of resistance. The azole antifungal agents have become the first choice of therapy for Candida infection and fluconazole is the most frequent drug prescribed in the 1990's. However, reports of resistance to these azole antifungals have appeared in recent years (see: Dupont, B. *Current Opinion in Infectious Diseases* 8, 424–427 1995). Because of the development of resistance to antifungals and adverse side-effects of current therapies for Candida infection, there is continuing need for new drug targets and new antibiotics.

SUMMARY OF THE INVENTION

The invention relates to isolated and/or recombinant nucleic acids which encode isoleucyl-tRNA synthetases of Candida origin. The invention also relates to recombinant DNA constructs and vectors containing DNA having a sequence which encodes an isoleucyl-tRNA synthetase of Candida origin or portions of the enzyme. These nucleic acids and constructs can be used to produce recombinant isoleucyl-tRNA synthetases of Candida origin.

A further embodiment of the invention is antisense nucleic acid which can hybridize to the nucleic acid which encodes an isoleucyl-tRNA synthetase of Candida. In cells, antisense nucleic acid can inhibit the function of an RNA which encodes an isoleucyl-tRNA synthetase of Candida.

The invention also relates to proteins or polypeptides, including fusion proteins, referred to herein as isolated and/or recombinant Candida isoleucyl-tRNA synthetases. These proteins are useful in the synthesis of peptides and related products, in assays to identify inhibitors of isoleucyl-tRNA synthetase function (including inhibitors having antimicrobial activity), in biochemical separations of isoleucine, and in quantitations of isoleucine and ATP. Antibodies which bind to isoleucyl-tRNA synthetases can be made and can be used in the purification and study of these enzymes.

Recombinant Candida isoleucyl-tRNA synthetases can be produced in host cells using cells and methods described herein. Tester strains, which are cells engineered to rely on the function of the tRNA synthetase encoded by an introduced cloned gene, are also an embodiment of the invention. Tester strains can be used to test the effectiveness and/or specificity of drug candidates in the inhibition of the essential tRNA synthetase enzyme encoded by the introduced cloned gene. In this way, potential inhibitors of the enzyme can be screened for antimicrobial or antibiotic effects, without requiring the culture of pathogenic strains of Candida, such as *Candida albicans*.

BRIEF DESCRIPTION OF THE DRAWINGS

SEQ ID NO:1 is an illustration of the 3720 basepair nucleotide sequence determined for the isoleucyl-tRNA synthetase (IleRS) gene of *C. albicans*, and SEQ ID NO:2 is the predicted amino acid sequence of the encoded protein (translated using the standard genetic code, as opposed to the non-universal genetic code used by *C. albicans*), starting from the initiator methionine codon at base 375.

(FIG. 1A) lane 1: molecular weight markers; lane 2: total soluble proteins in crude extracts; lane 3: flow-through from Glutathione Sepharose 4B column; lane 4: eluent from Glutathione Sepharose 4B column (affinity purified GST-IleRS).

(FIG. 1B) lane 1: high molecular weight markers; lane 2: affinity purified GST-IleRS protein after 14 hours of incubation at 16° C. in the absence of thrombin; lane 3: purified GST-IleRS protein after 14 hours of incubation at 16° C. with 0.5 units thrombin; lane 4: purified GST-IleRS protein after 14 hours of incubation at room temperature in the absence of thrombin; lane 5: purified GST-IleRS protein after 14 hours of incubation at room temperature in the presence of 0.5 units of thrombin; lane 6: molecular weight markers.

FIG. 4A is a photograph of an ethidium bromide-stained agarose gel containing molecular weight markers λHindIII (lane 1), 10 μg of EcoRI-digested rat DNA (lane 2), 1 μg of EcoRI digested *E. coli* DNA (lane 3), 2.5 μg of EcoRI-digested *C. albicans* DNA (lane 4), 2.5 μg of EcoRI-digested S. cerevisiae DNA (lane 5) and DNA molecular weight marker X (Boehringer Mannheim) (lane 6).

FIG. 4B is a scan onto photographic paper of an autoradiogram showing the result of hybridization of C. albicans-specific probe DNA (as obtained in Example 3A) with the DNA on the gel shown in FIG. 4A.

DETAILED DESCRIPTION OF THE INVENTION

Figure 1A:
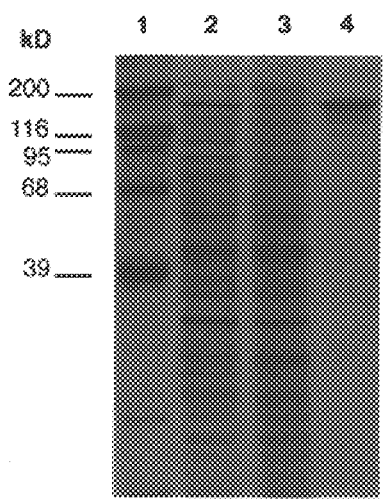
FIGS. 1A and 1B are photographs of 10% polyacrylamide gels stained with Coomassie blue which show the expression and affinity purification of an N-terminal GST-fusion protein of *Candida albicans* IleRS (GST-IleRS) (FIG. 1A), and products of thrombin cleavage of the purified GST-fusion protein of *C. albicans* IleRS (FIG. 1B) (Example 6A).

The aminoacyl-tRNA synthetases are enzymes with the common general function of catalyzing the following reaction:

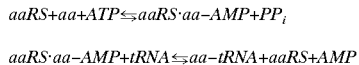

(aaRS=aminoacyl-tRNA synthetase; aa=amino acid; ATP=adenosine 5'-triphospate; AMP=adenosine 5'-monophosphate; PP$_i$=inorganic pyrophosphate) The second (aminoacylation) step is often referred to as "charging" the tRNA.

Generally, in each bacterial organism, there are 20 aminoacyl-tRNA synthetases, each specific for a different amino acid. Eucaryotic organisms also typically encode 20 cytoplasmic aaRSs, one specific for each amino acid. In addition, eucaryotic organisms generally encode a separate set of mitochondrial aaRSs. In the yeast *Saccharomyces cerevisiae*, the cytoplasmic and mitochondrial enzymes are usually encoded by separate nuclear genes, however exceptions have been found in which one gene encodes both cytoplasmic and mytochondrial enzyme (Natsoulis, G., et al., *Cell* 46:235–243 (1986); Chatton, B., et al., *J. Biol. Chem.* 263:52–57 (1988)). Each aminoacyl-tRNA synthetase enzyme recognizes and reacts with a specific amino acid and with one or more tRNAs that recognize the codons specific for that amino acid (cognate tRNAs). The specificity of the aaRS for the amino acid is determined by protein-amino acid interactions, and the specificity of the aaRS for the tRNA is determined by protein-RNA interactions, using different sites on the aaRS and tRNA molecules.

The tRNA synthetases can be subdivided into two groups of enzymes, class I and class II, based on short regions of sequence homology as well as distinct active site core tertiary structures (Eriani, G., et al., *Nature* 347:203–206 (1990); Moras, D., *Trends Biochem. Sci.* 17:159–164 (1992); Burbaum, J. J. and Schimmel, P., *J. Biol Chem.* 266(26) :16965–16968 (1991)). The large monomeric isoleucyl-tRNA synthetase has been classified as a class I synthetase. This enzyme contains the signature peptide sequences, HIGH and KMSKS, that are part of the nucleotide binding fold present in all class I synthetases.

Nucleic Acids, Constructs and Vectors

The present invention relates to isolated and/or recombinant (including, e.g., essentially pure) nucleic acids having sequences which encode a Candida isoleucyl-tRNA synthetase, or a portion of a Candida isoleucyl-tRNA synthetase. In one embodiment, the nucleic acid or portion thereof encodes a protein or polypeptide having at least one function characteristic of a Candida isoleucyl-tRNA synthetase, such as a catalytic activity (e.g., catalysis of isoleucyl-adenylate formation, catalysis of aminoacylation of a tRNA with isoleucine), and/or binding function (e.g., tRNA-, isoleucine- or ATP-binding), and/or antigenic function (e.g., binding of antibodies that also bind to naturally occurring Candida IleRS), and/or oligomerization function. Oligomerization activity is the ability of a protein subunit or protein fragment to bind together with one or more other protein subunits or protein fragments, thus altering the quaternary structure of the resulting complex. For example, "adhesive" fragments with oligomerization activity can bind to another fragment with no catalytic activity of its own to restore or partially restore enzymatic activity (Jasin, M., et al., U.S. Pat. No. 4,952,501). The present invention also relates more specifically to isolated and/or recombinant nucleic acids or a portion thereof having sequences which encode a isoleucyl-tRNA synthetase of *Candida albicans* origin, or a portion thereof.

The invention further relates to isolated and/or recombinant nucleic acids that are characterized by (1) their ability to hybridize to (a) a nucleic acid having the sequence of SEQ ID NO:1 or of SEQ ID NO:22 or portions of either of the foregoing (e.g., a portion comprising the open reading frame); or (2) by their ability to encode a polypeptide having the amino acid sequence of a Candida isoleucyl-tRNA synthetase (e.g., SEQ ID NO:23) or portions thereof, or functional equivalents thereof (e.g., a polypeptide which aminoacylates the isoaccepting cognate tRNAs (such as tRNA$^{Ile}$ of *C. albicans*) with isoleucine); or (3) by both characteristics. A nucleic acid which hybridizes to a nucleic acid encoding a Candida IleRS such as SEQ ID NO:1, can be double- or single-stranded. Hybridization to DNA such as DNA having the sequence SEQ ID NO:1 includes hybridization to the strand shown or its complementary strand. In one embodiment, the percent amino acid sequence similarity between a Candida isoleucyl-tRNA synthetase, such as the polypeptide encoded by SEQ ID NO:1 and functional equivalents thereof is at least about 80% (≧80%). In a preferred embodiment, the percent amino acid sequence similarity between between a Candida isoleucyl-tRNA synthetase and its functional equivalents is at least about 85% (≧85%). More preferably, the percent amino acid sequence similarity between between a Candida isoleucyl-tRNA synthetase and its functional equivalents is at least about 90%, and still more preferably, at least about 95%.

Isolated and/or recombinant nucleic acids meeting these criteria comprise nucleic acids having sequences identical to sequences of naturally occurring Candida IleRS genes, including allelic variants, and portions thereof, or variants of the naturally occurring sequences. Such variants include mutants differing by the addition, deletion or substitution of one or more residues, modified nucleic acids in which one or more residues are modified (e.g., DNA or RNA analogs), and mutants comprising one or more modified residues. Preferred embodiments of isolated and/or recombinant nucleic acids are those encoding isoleucyl-tRNA synthetases of Candida species other than *C. utilis*; particularly preferred are isolated and/or recombinant nucleic acids encoding isoleucyl-tRNA synthetases of pathogenic species, including, but not limited to, *C. albicans, C. pseudotropicalis, C. stellatoidea, C. guilliermondi, C. glabrata, C. krusei, C. parapsilosis*, and *C. tropicalis*.

Such nucleic acids, including DNA or RNA, can be detected and isolated by hybridization under high stringency conditions or moderate stringency conditions, for example. "Stringency conditions" for hybidization is a term of art which refers to the conditions of temperature and buffer concentration which permit hybridization of a particular nucleic acid to another nucleic acid in which the first nucleic acid may be perfectly complementary to the second, or the first and second may share only some degree of complementarity. For example, certain high stringency conditions can be used which distinguish perfectly complementary nucleic acids from those of less complementarity. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M., et al., Eds., Vol. 1, containing supplements up through Supplement 29, 1995), the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus high or moderate stringency conditions can be determined empirically.

For example, if a set of hybridization conditions is used which is determined to allow hybridization between nucleic acids which are too dissimilar in sequence for the purposes of an experiment, then the hybridization conditions can be altered in subsequent experiments to a higher stringency to achieve selectivity to the desired level of sequence similarity. Higher stringency conditions can be achieved, for example, by raising the temperature of the hybridization and post-hybridization washes, and/or by decreasing the ionic strength (usually, the SSC concentration) of the hybridization buffer and post-hybridization washes. This strategy can be applied, for example, to exclude cross-hybridization of a *C. albicans*-probe to *S. cerevisiae* DNA which may occur. For example, starting from the "high stringency" conditions given in Example 3A, stringency can be increased to "very high stringency" conditions under which hybridization to *S. cerevisiae* DNA does not occur.

By varying hybridization conditions from a level of stringency at which no hybridization occurs to a level at which hybridization is first observed, conditions which will allow a given sequence to hybridize with the most similar sequences in the sample can also be determined.

Exemplary conditions are described in Krause, M. H. and Aaronson, A. S.; *Methods in Enzymology*, 200:546–556 (1991). Also see especially page 2.10.11 in *Current protocols in Molecular Biology* (supra), which describes how to determine washing conditions. Washing is the step in which conditions are usually set so as to determine a minimum level of complementarity of the hybrids and eliminate free non-hybridized radioactive probe as well as background and non-specific weak interaction. Generally, starting from the lowest temperature at which only homologous hybridization occurs, each degree Celsius by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought.

Isolated and/or recombinant nucleic acids that are characterized by their ability to hybridize to a nucleic acid encoding a Candida isoleucyl-tRNA synthetase such as the nucleic acid depicted in SEQ ID NO:1 or a portion therof (e.g. under high or moderate stringency conditions), may further encode a protein or polypeptide having at least one function characteristic of a Candida isoleucyl-tRNA synthetase, such as a catalytic activity (e.g., isoleucyl-adenylate formation, aminoacylation of a tRNA with isoleucine), binding function (e.g., tRNA-, isoleucine-, or ATP-binding), antigenic function (e.g., binding of antibodies that also bind to non-recombinant Candida IleRS), and/or oligomerization function. The catalytic or binding function of a protein or polypeptide encoded by hybridizing nucleic acid may be detected by standard enzymatic assays for activity or binding (e.g., assays which monitor aminoacyl-adenylate formation, aminoacylation of tRNA with isoleucine). Functions characteristic of a isoleucyl-tRNA synthetase may also be assessed by in vivo complementation activity or other suitable methods. Enzymatic assays, complementation tests, or other suitable methods can also be used in procedures for the identification and/or isolation of nucleic acids which encode a polypeptide such as a polypeptide of the amino acid sequence SEQ ID NO:2, or functional equivalents of these polypeptides. The antigenic properties of proteins or polypeptides encoded by hybridizing nucleic acids can be determined by immunological methods employing antibodies that bind to a Candida isoleucyl-tRNA synthetase, such as immunoblot, immunoprecipitation and radioimmunoassay.

The identification of nucleic acids with sequences related to those of the *C. albicans* IleRS gene is not limited to hybridization methods. The identification of additional Candida IleRS genes can also be accomplished by an extension of the methods used to isolate *Candida albicans* IleRS-specific fragments as explained in Examples 1–3. For example, pairs of degenerate oligonucleotides that were successfully used in a PCR reaction to identify the *C. albicans* cytoplasmic IleRS gene and IleRS mitochondrial fragment can be used in PCR reactions using the reaction conditions described below or other suitable conditions. Since these primer pairs, which were created based upon DNA sequence information of non-Candida species, were able to amplify a *C. albicans* PCR product, it is reasonable to expect that they can amplify a PCR product from other related Candida species. The same degenerate primer pairs that were used in PCR reactions to isolate *C. albicans* IleRS-specific fragments can be used with other Candida species (e.g., genomic DNA, a cloned library). Once a fragment of the Candida species IleRS is generated by PCR, it can be sequenced. To determine if the DNA sequence of the PCR product encodes an IleRS, the sequence of the product can be compared to other DNA sequences. The entire gene sequence (including the 5' and 3' ends) can then be identified. For example, semi-specific PCR can be used.

An isoleucyl-tRNA synthetase gene or portion thereof is producible by methods described herein or other suitable methods. For example, primers (e.g., a pair of primers or nested primers) can be designed which comprise a sequence which is complementary or substantially complementary to a portion of the gene encoding *C. albicans* IleRS. Primers can contain portions which are complementary to other sequences as appropriate, such as restriction recognition sequences, template sequences (e.g., vector sequences flanking the inserts in a gene library) or other sequences. For instance, primers complementary to the 5'- and 3'-ends of the coding sequence and or flanking regions shown in SEQ ID NO:1 can be designed. Such primers can be used in a polymerase chain reaction with a suitable nucleic acid template (e.g., a construct described herein, a library or another suitable nucleic acid) to obtain a C. albicans IleRS gene or portion thereof.

Nucleic acids of the present invention can be used in the production of proteins or polypeptides. For example, DNA containing all or part of the coding sequence for a Candida isoleucyl-tRNA synthetase, or DNA which hybridizes to DNA having the sequence SEQ ID NO:1, can be incorporated into various constructs and vectors created for further manipulation of sequences or for production of the encoded polypeptide in suitable host cells.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction into the cells of nucleic acids designed to allow and make probable a desired recombination event.

Portions of the isolated nucleic acids which code for polypeptides having a certain function can be identified and isolated by, for example, the method of Jasin, M., et al., U.S. Pat. No. 4,952,501.

A further embodiment of the invention is antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In a particular embodiment, the antisense nucleic acid is wholly or partially complementary to and can hybridize with a target nucleic acid, wherein the target nucleic acid can hybridize to a nucleic acid having the sequence of the complement of the top strand shown in FIGS. 1A–1D SEQ ID NO:1. For example, antisense nucleic acid can be complementary to a target nucleic acid having the sequence shown as the top strand of the open reading frame in SEQ ID NO:1, or to a portion thereof sufficient to allow hybridization. In another embodiment, the antisense nucleic acid is wholly or partially complementary to and can hybridize with a target nucleic acid which encodes a Candida isoleucyl-tRNA synthetase.

C. albicans is the most important human pathogen among Candida species. Because advances in the understanding and treatment of C. albicans infection would be of benefit, it was the species selected for most of the experimental work described herein. As described in the Exemplification, PCR fragments of C. albicans IleRS genes were isolated, cloned and used as probes to screen two genomic libraries of C. albicans (Goshorn, A., et al., Infect. Immun. 60:876–884 (1992), Goshorn, A. and Scherer, S. Genetics 123:667–673 (1989), Kwon-Chung, K. J. et al., Infect. Immun. 49:571–575 (1985), Slutsky, B. M., et al., J. Bacteriol.169:189 (1987); Baldari, C. and Cesareni, G., Gene 35:27, (1985)).

The isolated C. albicans gene is representative of a broader class of Candida isoleucyl-tRNA synthetase genes derived from various species of Candida. These additional genes can also be used to express Candida isoleucyl-tRNA synthetases, with utilities corresponding to those described herein, and can be used in the production of host cells and tester strains comprising recombinant Candida isoleucyl-tRNA synthetase genes using methods described herein. The approaches described herein, including, but not limited to, the approaches to isolate and manipulate the isoleucyl-tRNA synthetase gene of C. albicans, to construct vectors and host strains, and to produce and use the protein, to produce antibodies, etc., can be applied to other members of the genus Candida, including, but not limited to, pathogenic species such as C. pseudotropicalis, C. stellatoidea, C. guilliermondi, C. glabrata, C. krusei, C. parapsilosis, and C. tropicalis. For example, the isoleucyl-tRNA synthetase gene described here or sufficient portion thereof, whether isolated and/or recombinant or synthetic, including fragments produced by PCR, can be used to detect and/or recover homologous genes of the other Candida species (e.g., as probes for hybridization, or primers for PCR or other suitable techniques).

Proteins

It should be noted that certain species of Candida, including C. albicans, C. parapsilosis, C. zeylanoldes, C. rugosa, C. melibiosica and C. cylindracea, are known to use a variation of the "universal" genetic code which appears in genetics textbooks and treatises (for example, see pages 104–105 in Lewin, B., Genes, 3rd edition, John Wiley and Sons, New York, 1987; Ohama, T. et al., Nucleic Acids Res. 21:4039–4045 (1993)). It is known that in these species of Candida, the codon CUG, which codes for leucine in the universal genetic code, is decoded as serine by a non-universal genetic code of these species of Candida. It is possible that in these species of Candida, other codons may also determine a different amino acid from that determined by the universal code. Thus, the expression of a gene, such as a IleRS gene, in certain species of Candida, can result in a protein having a different amino acid sequence from the amino acid sequence that would result from the expression of the same gene in an organism using the universal genetic code. Other species of Candida which decode CUG as leucine include C. magnoliae, C. azyma, C. diversa, and C. rugopelliculosa (Ohama et al.).

The invention relates further to proteins or polypeptides encoded by nucleic acids of the present invention. The proteins and polypeptides of the present invention can be isolated and/or recombinant. Proteins or polypeptides referred to herein as "recombinant" are proteins or polypeptides produced by the expression of recombinant nucleic acids. Proteins or polypeptides referred to herein as "isolated" are proteins or polypeptides purified to a state beyond that in which they exist in cells, and include proteins or polypeptides obtained by methods described herein, similar methods or other suitable methods, including essentially pure proteins or polypeptides, proteins or polypeptides produced by chemical synthesis, or by combinations of biological and chemical methods, and recombinant proteins or polypeptides which are isolated. Preferred embodiments of isolated and/or recombinant proteins are isoleucyl-tRNA synthetases of Candida other than C. utilis; particularly preferred are isolated and/or recombinant isoleucyl-tRNA synthetases of pathogenic species, including, but not limited to, *C. albicans, C. pseudotropicalis, C. stellatoidea, C. guilliermondi, C. glabrata, C. krusei, C. parapsilosis*, and *C. tropicalis*.

In one embodiment, proteins or polypeptides are isolated to a state at least about 65% pure; more preferably at least about 75% pure, and still more preferably at least about 85% pure, as determined by Coomassie blue staining of proteins on SDS-polyacrylamide gels.

In a preferred embodiment, the protein or portion thereof has at least one function characteristic of a Candida isoleucyl-tRNA synthetase, for example, catalytic activity (e.g., catalysis of aminoacyl-adenylate formation, catalysis of aminoacylation of tRNA with isoleucine), binding function (e.g., tRNA-, amino acid-, or ATP-binding), antigenic function (e.g., binding of antibodies that also bind to non-recombinant Candida isoleucyl-tRNA synthetase), and/or oligomerization activity. As such, these proteins are referred to as isoleucyl-tRNA synthetases of Candida origin or Candida isoleucyl-tRNA synthetases, and include, for example, naturally occurring Candida isoleucyl-tRNA synthetases (including allelic variants), variants (e.g. mutants) of those proteins and/or portions thereof. Such variants include mutants differing by the addition, deletion or substitution of one or more amino acid residues, or modified polypeptides in which one or more residues are modified, and mutants comprising one or more modified residues.

In a particularly preferred embodiment, like naturally occurring Candida isoleucyl-tRNA synthetase, isolated and/or recombinant Candida isoleucyl-tRNA synthetases of the present invention aminoacylate the isoaccepting cognate tRNAs of the Candida organism with isoleucine in a two-step reaction. For example, an isolated, recombinant *C. albicans* isoleucyl-tRNA synthetase is able to aminoacylate each of the isoaccepting species of cognate tRNA$^{ile}$ of *C. albicans* with isoleucine. In the first step, the Candida isoleucyl-tRNA synthetase catalyzes the covalent linkage of isoleucine to ATP to form an adenylate complex (isoleucyl-adenylate) with the release of pyrophosphate, and, in a second step, catalyzes the covalent linkage of isoleucine to a specific tRNA recognized by the enzyme, releasing AMP.

The invention further relates to fusion proteins, comprising a Candida isoleucyl-tRNA synthetase (as described above) as a first moiety, linked to second moiety not occurring in the Candida IleRS as found in nature. Thus, the second moiety can be an amino acid or polypeptide. The first moiety can be in an N-terminal location, C-terminal location or internal to the fusion protein. In one embodiment, the fusion protein comprises a *C. albicans* isoleucyl-tRNA synthetase as the first moiety, and a second moiety comprising a linker sequence and affinity ligand.

Fusion proteins can be produced by a variety of methods. For example, a fusion protein can be produced by the insertion of a IleRS gene or portion thereof into a suitable expression vector, such as Bluescript SK +/− (Stratagene), pGEX-4T-2 (Pharmacia) and pET-15b (Novagen). The resulting construct is then introduced into a suitable host cell for expression. Upon expression, fusion protein can be purified from a cell lysate by means of a suitable affinity matrix (see e.g., *Current Protocols in Molecular Biology* (Ausubel, F. M., et al., Eds., Vol. 2, Suppl. 26, pp. 16.4.1–16.7.8 (1991)).

The invention also relates to isolated and/or recombinant portions or fragments of a isoleucyl-tRNA synthetase of Candida origin. Portions of the enzyme can be made which have full or partial function on their own, or which when mixed together (though fully, partially, or nonfunctional alone), spontaneously assemble with one or more other polypeptides to reconstitute a functional protein having at least one function characteristic of a Candida isoleucyl-tRNA synthetase. (See, e.g., Shiba, K. and Schimmel, P., *J. Biol. Chem.* 267:22703–22706 (1992) for an example of three inactive peptides from *E. coli* IleRS spontaneously assembling in vivo to reconstitute active enzyme; see also, Burbaum, J. and Schimmel, P., *Biochemistry* 30(2): 319–324 (1991), describing non-overlapping segments of *E. coli* MetRS that can fold together to reconstitute an active enzyme capable of recognizing and charging tRNA in vitro and in vivo; see also Jasin, M., et al., (U.S. Pat. No. 4,952,501) describing deletion studies of *E. coli* alanyl-tRNA synthetase which showed that large portions of the protein were unnecessary for specific aminoacylation activity). Based on this type of analysis, portions of a Candida IleRS can be made which have at least one function characteristic of a Candida isoleucyl-tRNA synthetase, such as a catalytic function, binding function, antigenic function and/or oligomerization function. Studies on the structure and function of the aaRSs provide the basis for being able to divide the Candida aaRS enzymes into functional domains (Schimmel, P., *Current Biology* 1:811–816 (1991)).

The sequences and structures of the catalytic domains of several tRNA synthetases which have been purified and studied have led to the identification of two distinct classes designated class I and class II (Schimmel, P., *Ann. Rev. Biochem.* 56:125–158 (1987); Webster, T. A., et al., *Science* 226:1315–1317 (1984); Eriani, G., et al, *Nature* 347:203–206 (1990) and Cusack, S., et al., *Nature* 347:249–255 (1990)). Class I enzymes have a well-conserved N-terminal nucleotide binding fold responsible for amino acid binding, aminoacyl-adenylate formation, and tRNA acceptor helix docking. The N-terminal Rossman nucleotide binding fold is comprised of alternating β-strands and α-helices and comprises conserved motifs such as the HIGH tetrapeptide located in the first half of the Rossman fold and the KMSKS pentapeptide located in the second half of the Rossman fold. These elements are landmarks of class I synthetases. The C-terminal domain is rich in α-helices and contains residues needed for interactions with the parts of the tRNA distal to the amino acid attachment site (Shepard, A., et al., *Proc. Natl. Acad. Sci. U.S.A.* 89:9964–9968 (1992); Hou, Y.-M., et al., *Proc. Natl. Acad. Sci. U.S.A.* 88:976–980 (1991)). In some tRNA synthetases, this second domain interacts directly with the anticodon (Rould, M. A., et al., *Science* 246:1135–1142 (1989) and Cavarelli, J., et al., *Nature* 362:181–184 (1993)), while in other enzymes there is no contact made between the second domain and the anticodon (Biou, V., et al., *Science* 263:1404–1410 (1994)). To a first approximation, the two domains in class I tRNA synthetases interact with the two distinct domains of the L-shaped tRNA structure. Thus, the recognition elements of the tRNA synthetase and of the tRNA which are needed for the operational RNA code are segregated into discrete protein and RNA domains.

Consideration of this information, along with the remaining teachings of the specification, allows the construction of *C. albicans* isoleucyl-tRNA synthetase derivatives which possess at least one function characteristic of a Candida isoleucyl-tRNA synthetase.

Method of Producing Recombinant IleRSs

Another aspect of the invention relates to a method of producing a Candida isoleucyl-tRNA synthetase or a portion thereof, and to expression systems and host cells containing a vector appropriate for expression of the Candida isoleucyl-tRNA synthetase.

Cells that express a recombinant isoleucyl-tRNA synthetase or a portion thereof can be made and maintained in culture under conditions suitable for expression to produce protein for isolation and purification. These cells can be procaryotic or eucaryotic. Examples of procaryotic cells that can be used to express Candida isoleucyl-tRNA synthetases include *Escherichia coli* (e.g., BL21, BL22, JM109), *Bacillus subtilis* and other bacteria. Examples of eucaryotic cells that can be used to express the isoleucyl-tRNA synthetases include yeasts such as *Saccharomyces cerevisiae, S. pombe, Pichia pastoris*, and other lower eucaryotic cells, as well as cells of higher eucaryotes, such as those from insects and mammals. (See, e.g., Ausubel, F. M. et al., Eds. *Current Protocols in Molecular Biology*, Greene Publishing Associates and John Wiley & Sons Inc., (1993)).

In one embodiment, host cells that produce a recombinant Candida IleRS protein or portion thereof for isolation and purification can be made as follows. A gene encoding a IleRS can be inserted into a nucleic acid vector, e.g., a DNA vector, such as a plasmid, virus or other suitable replicon, which can be present in a single copy or multiple copies, or the gene can be integrated in a host cell chromosome. Such a suitable replicon contains all or part of the coding sequence for Candida isoleucyl-tRNA synthetase operably linked to one or more expression control sequences whereby the coding sequence is under the control of transcription signals and linked to appropriate translation signals to permit translation of the IleRS, portion thereof, or of a fusion protein comprising an IleRS or portion thereof. The vector can be introduced into cells by a method appropriate to the type of host cells (e.g., transformation, electroporation, transfection, infection). For expression from the IleRS gene, the host cells can be maintained under appropriate conditions, e.g., in the presence of inducer, normal growth conditions, etc.).

For example, Candida isoleucyl-tRNA synthetase can be produced by integrating a gene encoding the *C. albicans* IleRS into the genome of a virus that enters the host cells. By infection of the host cells, the components of a system which permits the transcription and translation of the Candida IleRS gene are present in the host cells. Alternatively, an RNA polymerase gene, inducer, or other component required to complete such a gene expression system may be introduced into the host cells already containing the Candida IleRS gene, for example, by means of a virus that enters the host cells and contains the required component. The Candida IleRS gene can be under the control of an inducible or constitutive promoter. The promoter can be one that is recognized by the host cell RNA polymerase. The promoter can, alternatively, be one that is recognized by a viral RNA polymerase and is transcribed following infection of the host cells with a virus.

Antibodies

The invention further relates to antibodies that bind to an isolated and/or recombinant Candida isoleucyl-tRNA synthetase, including portions of antibodies (e.g., a peptide), which can specifically recognize and bind to the isoleucyl-tRNA synthetase. These antibodies can be used in methods to purify the enzyme or portion thereof, for example by immunoaffinity chromatography, or to selectively inactivate one of the enzyme's active sites, or to study other aspects of enzyme structure, for example.

The antibodies of the present invention can be polyclonal or monoclonal, and the term antibody is intended to encompass both polyclonal and monoclonal antibodies. Antibodies of the present invention can be raised against an appropriate immunogen, including proteins or polypeptides of the present invention, such as an isolated and/or recombinant Candida isoleucyl-tRNA synthetase or portion thereof, or synthetic molecules, such as synthetic peptides. The immunogen, for example, can be a protein having at least one function of a Candida isoleucyl-tRNA synthetase, as described herein.

The term antibody is also intended to encompass single chain antibodies, chimeric, humanized or primatized (CDR-grafted) antibodies, and the like, as well as chimeric or CDR-grafted single chain antibodies, comprising portions from more than one species. For example, the chimeric antibodies can comprise portions of proteins derived from two different species, joined together chemically by conventional techniques or prepared as a contiguous protein using genetic engineering techniques (e.g., DNA encoding the protein portions of the chimeric antibody can be expressed to produce a contiguous protein chain). See, e.g., Cabilly, et al., U.S. Pat. No. 4,816,567; Cabilly, et al., European Patent No. 0,125,023 B1; Boss, et al., U.S. Pat. No. 4,816,397; Boss, et al., European Patent No. 0,120,694 B1; Neuberger, M. S., et al., WO 86/01533; Neuberger, M. S., et al., European Patent No. 0,194,276 B1; Winter, U.S. Pat. No. 5,225,539; and Winter, European Patent No. 0,239, 400 B1. See also, Newman, R., et al., *BioTechnology* 10: 1455–1460 (1992), regarding primatized antibody, and Ladner, et al., U.S. Pat. No. 4,946,778 and Bird, R. E., et al., *Science* 242: 423–426 (1988)) regarding single chain antibodies.

Whole antibodies and biologically functional fragments thereof are also encompassed by the term antibody. Biologically functional antibody fragments which can be used include those fragments sufficient for binding of the antibody fragment to a Candida IleRS to occur, such as Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the $CH_1$ domain and hinge region of the heavy chain.

Preparation of immunizing antigen, and polyclonal and monoclonal antibody production can be performed using any suitable technique. A variety of methods have been described (see e.g., Kohler, et al., *Nature* 256: 495–497 (1975) and *Eur. J. Immunol.* 6: 511–519 (1976); Milstein, et al., *Nature* 266: 550–552 (1977); Koprowski, et al., U.S. Pat. No. 4,172,124; Harlow, E. and Lane, D.; 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M., et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably those obtained from the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Assays for Inhibitors and Tester Strains

The enzymatic assays, binding assays, and construction of tester strains described below, which rely upon the nucleic acids and proteins of the present invention, can be used, alone or in combination with each other or other suitable methods, to identify inhibitors of one or more Candida isoleucyl-tRNA synthetases.

Enzyme Assay

Upon isolation from a species of the genus Candida, a IleRS gene can be incorporated into an expression system for production of the IleRS enzyme as a native or a fusion protein, followed by isolation and testing of the enzyme in vitro. The isolated or purified Candida IleRSs can also be used in further structural studies that allow for the design of antibiotics which specifically target one or more aaRSs of Candida, while not affecting or minimally affecting host or mammalian (e.g., human) aaRSs. Because the amino acid sequences of the tRNA synthetases have diverged over evolution, significant differences exist between the structure of the enzymes from mammals (e.g., human, bovine) and mammalian pathogens, and the design or selection of inhibitors can exploit the structural differences between the pathogen aaRS and the host (e.g., a mammalian host, such a human) aaRS to yield specific inhibitors of the pathogen aaRS, which may further have antimicrobial activity.

Furthermore, isolated, active Candida IleRSs can be used in an in vitro method of screening for inhibitors of isoleucyl-tRNA synthetase activity in which the inhibitory effect of a compound is assessed by monitoring IleRS activity according to standard techniques. For example, inhibitors of the activity of isolated, recombinant *C. albicans* IleRS can be identified by the method. In one embodiment, the isolated IleRS enzyme is maintained under conditions suitable for isoleucyl-adenylate formation, the enzyme is contacted with a compound to be tested, and formation of the isoleucyl-adenylate is monitored by standard assay. A reduction in the activity measured in the presence of compound, as compared with the activity in the absence of compound, is indicative of inhibition of isoleucyl-tRNA synthetase activity by the compound.

For example, the extent of isoleucyl-adenylate formation catalyzed by purified TyrRS can be measured using an ATP-pyrophosphate exchange assay in the presence and in the absence of a candidate inhibitor (Calendar, R. and Berg, P., *Biochemistry* 5:1690–1695 (1966)). In this reaction, the enzymatic synthesis of ATP from AMP and pyrophosphate in the absence of tRNA is monitored. A candidate inhibitor can be added to a suitable reaction mixture (e.g., 100 mM Tris-HCl, pH 7.5/5 mM $MgCl_2$/10 mM 2-mercaptoethanol/ 10 mM KF/2 mM ATP/2 mM [$^{32}$P]pyrophosphate/1 mM isoleucine), and the mixture is incubated at 25° C. IleRS (to a final concentration of ~10 nM) is added to initiate the reaction. Aliquots of the reaction are removed at various times and quenched in 7% (vol/vol) cold perchloric acid, followed by the addition of 3% (wt/vol) charcoal suspended in 0.5% HCl. The ATP adsorbed to charcoal is filtered onto glass fiber pads (Schleicher & Schuell), and formation of [$^{32}$P]ATP is quantified by liquid scintillation counting in Hydrofluor (National Diagnostics, Manville, N.J.). The enzyme activity measured in the presence of the compound can be compared with the activity in the absence of the compound to assess the level of inhibition. Alternatively, a candidate inhibitor can be preincubated with enzyme under suitable conditions. Preincubation in the absence of substrate provides a more sensitive assay for the detection of inhibition (e.g., detects slow binding inhibitors). For example, the compound can be added to a mixture containing ~10 nM isoleucyl-tRNA synthetase in 100 mM Tris-HCl, pH 7.5/5 mM $MgCl_2$/10 mM 2-mercaptoethanol/10 mM KF, and preincubated at 25° C. for 20 minutes. To initiate the reaction, ATP, [$^{32}$P]pyrophosphate and isoleucine are added to final concentrations of 2 mM, 2 mM and 1 mM, respectively. The reaction can be monitored as described above, and the activity measured in the presence of compound is compared with the activity in the absence of compound to assess the level of inhibition.

In another embodiment, formation of the aminoacylated tRNA is monitored in a standard aminoacylation assay. Inhibitors identified by enzymatic assay can be further assessed for antimicrobial activity using tester strains as described herein, or using other suitable assays. For example, the extent of aminoacylation of tRNA with isoleucine catalyzed by IleRS (e.g., a GST fusion) can be measured by monitoring the incorporation of [$^3$H]isoleucine into trichloroacetic acid-precipitable [$^3$H]isoleucyl-tRNA in the presence of a candidate inhibitor, as compared with activity in the absence inhibitor. Appropriately diluted IleRS can be preincubated for 20 minutes at 25° C. in, for example, 50 mM HEPES, pH 7.5/0.1 mg/ml BSA (bovine serum albumin)/10 mM $MgCl_2$/10 mM 2-mercaptoethanol/20 mM KCl/1–20% DMSO (preferably about 1%) in the presence or absence of a compound to be tested. The preincubation mixture can be supplemented with ATP, [$^3$H]isoleucine and tRNA to final concentrations of, for example, 4 mM ATP/20 $\mu$M [$^3$H]isoleucine (0.6 $\mu$Ci), and 90 $\mu$M crude tRNA or 2 $\mu$M specific tRNA$^{Ile}$. The reaction is maintained at 25° C., and aliquots are removed at specific times, and applied to filter paper discs (3 MM, Whatman) that have been pre-soaked with 5% (wt/vol) trichloroacetic acid. Filters are washed for three 10-minute periods in 5% trichloroacetic acid, rinsed in 95% ethanol and 100% ether, and the incorporation of $^3$H-isoleucine into tRNA (formation of $^3$H-Ile-tRNA) can be measured in Betafluor by liquid scintillation counting. The aminoacylation assay can also be performed without preincubation under suitable conditions (e.g., using ~0.4 nM IleRS in a reaction mixture containing 50 mM HEPES, pH 7.5/0.1 mg/ml BSA (bovine serum albumin)/10 mM $MgCl_2$/10 mM, 2-mercaptoethanol/20 mM KCl/1–20% DMSO/4 mM ATP/20 $\mu$M [$^3$H]isoleucine (0.6 $\mu$Ci), and 90 $\mu$M crude tRNA or 2 $\mu$M specific tRNA$^{Ile}$) in the presence or absence of test compound. An $IC_{50}$ value (the concentration of inhibitor causing 50% inhibition of enzyme activity) for a known amount of active IleRS can be determined.

Binding Assay

An isolated, recombinant aaRS or a portion thereof, and suitable fusion proteins can be used in a method to select and identify compounds which bind specifically to Candida IleRSs, such as *C. albicans* isoleucyl-tRNA synthetase, and which are potential inhibitors of IleRS activity. Compounds selected by the method can be further assessed for their inhibitory effect on IleRS activity and for antimicrobial activity.

In one embodiment, an isolated or purified Candida IleRS can be immobilized on a suitable affinity matrix by standard techniques, such as chemical cross-linking, or via an antibody raised against the isolated or purified IleRS, and bound to a solid support. The matrix can be packed in a column or other suitable container and is then contacted with one or more compounds (e.g., a mixture) to be tested under conditions suitable for binding of compound to the IleRS. For example, a solution containing compounds can be made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds.

Alternatively, the elution buffer can comprise a release component or components designed to disrupt binding of compounds (e.g., one or more substrates or substrate analogs which can disrupt binding of compound to the IleRS, such as isoleucine, ATP, tRNA$^{Ile}$, or other suitable molecules which competitively inhibit binding).

Fusion proteins comprising all of, or a portion of, the IleRS linked to a second moiety not occurring in the Candida IleRS as found in nature (see above), can be prepared for use in another embodiment of the method. Suitable fusion proteins for this purpose include those in which the second moiety comprises an affinity ligand (e.g., an enzyme, antigen, epitope). The fusion proteins can be produced by the insertion of an IleRS gene or portion thereof into a suitable expression vector, which encodes an affinity ligand (e.g., pGEX-4T-2 and pET-15b, encoding glutathione S-transferase and His-Tag affinity ligands, respectively). The expression vector can be introduced into a suitable host cell for expression. Host cells are lysed and the lysate, containing fusion protein, can be bound to a suitable affinity matrix by contacting the lysate with an affinity matrix under conditions sufficient for binding of the affinity ligand portion of the fusion protein to the affinity matrix.

In one aspect of this embodiment, the fusion protein can be immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the IleRS portion of the bound fusion protein. Next, the affinity matrix with bound fusion protein can be washed with a suitable wash buffer to remove unbound compounds and non-specifically bound compounds. Compounds which remain bound can be released by contacting the affinity matrix with fusion protein bound thereto with a suitable elution buffer (a compound elution buffer). Wash buffer can be formulated to permit binding of the fusion protein to the affinity matrix, without significantly disrupting binding of specifically bound compounds. In this aspect, compound elution buffer can be formulated to permit retention of the fusion protein by the affinity matrix, but can be formulated to interfere with binding of the compound(s) tested to the IleRS portion of the fusion protein. For example, a change in the ionic strength or pH of the elution buffer can lead to release of compounds, or the elution buffer can comprise a release component or components designed to disrupt binding of compounds to the IleRS portion of the fusion protein (e.g., one or more substrates or substrate analogs which can disrupt binding of compounds to the IleRS portion of the fusion protein, such as isoleucine, ATP, or tRNA$^{Ile}$, or other suitable molecules which competitively inhibit binding).

Immobilization can be performed prior to, simultaneous with, or after contacting the fusion protein with compound, as appropriate. Various permutations of the method are possible, depending upon factors such as the compounds tested, the affinity matrix-ligand pair selected, and elution buffer formulation. For example, after the wash step, fusion protein with compound bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

To enrich for specific binding to the IleRS portion of the fusion protein, compounds can be pre-treated, for example with affinity matrix alone, with affinity ligand or a portion thereof (e.g., the portion present in the fusion protein), either alone or bound to matrix, under conditions suitable for binding of compound to the IleRS portion of the bound fusion protein.

One or more compounds can be tested simultaneously according to the method. Where a mixture of compounds is tested, the compounds selected by the foregoing processes can be separated (as appropriate) and identified by suitable methods (e.g., PCR, sequencing, chromatography). Large combinatorial libraries of compounds (e.g., organic compounds, peptides, nucleic acids) produced by combinatorial chemical synthesis or other methods can be tested (see e.g., Ohlmeyer, M. H. J., et al., *Proc. Natl. Acad. Sci. USA* 90:10922–10926 (1993) and DeWitt, S. H., et al., *Proc. Natl. Acad. Sci. USA* 90:6909–6913 (1993), relating to tagged compounds; see also Rebek, et al., Process for Creating Molecular Diversity, U.S. Ser. No. 08/180,215, filed Jan. 12, 1994, relating to compounds without tags; see also, Rutter, W. J., et al., U.S. Pat. No. 5,010,175; Huebner, V. D., et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible. Where compounds do not carry tags, chromatographic separation, followed by mass spectrophotometry to ascertain structure, can be used to identify individual compounds selected by the method, for example.

Random sequence RNA and DNA libraries (see Ellington, A. D., et al., *Nature* 346: 818–822 (1990); Bock, L. C., et al., *Nature* 355: 584–566 (1992); and Szostak, J. W., *Trends in Biochem. Sci.* 17:89–93 (March, 1992)) can also be screened according to the present method to select RNA or DNA molecules which bind to a Candida IleRS. Such molecules can be further assessed for antimicrobial effect upon introduction into a cell (e.g., by expression in the case of an RNA molecule selected by the method).

Tester Strains

Nucleic acids of the present invention can also be used in constructing tester strains for in vivo assays of the effect on the activity of the Candida enzyme of a substance which is added to tester strain cells. A tester strain comprises a host cell having a defect in a gene encoding an endogenous aaRS, and a heterologous aaRS gene which complements the defect in the host cell gene. Thus, complementation of a particular defective host cell aaRS gene by a heterologous aaRS gene is a threshold requirement for a tester strain. Because the aaRS genes are essential, the heterologous gene can be introduced into the host cell simultaneously with inactivation of the host cell gene to preserve viability. Alternatively, the heterologous gene can be introduced into the host cell before inactivation or loss of the host cell gene. In this case, to test for complementation, the host cell is then subjected to some change in conditions (e.g., a change in temperature, growth medium, selection conditions) which causes inactivation or loss of either the host aaRS gene or gene product, or both.

If the heterologous gene complements the inactivated host cell gene, such a cell can be used to determine whether a substance that is introduced into the cells for testing, can interact specifically with the heterologous tRNA synthetase (or a component in the pathway of the expression of the heterologous tRNA synthetase gene) to cause loss of function of the tested heterologous tRNA synthetase in those host cells. Thus, such cells are "tester strains". Successful cross-species complementation has been described, for example, for yeast seryl-tRNA synthetase and for yeast isoleucyltRNA synthetase in *E. coli* (Weygand-Durasevic, I., et al., *Eur. J. Biochem* 214:869–877 (1993); Racher, K. I., et al.,*J. Biol. Chem.* 266:17158–17164 (1991)).

In tester cells to be used in an assay for chemical substances that can inhibit the function of a specific aaRS, the gene for the aminoacyl-tRNA synthetase can, for example, physically replace the host cell aaRS gene or can be present in addition to a host aaRS gene that does not produce a functional product, and the heterologous gene whose gene product is to be tested complements the host gene. A substance to be tested is administered to the tester cells, and the viability or growth of such cells can be compared with that of cells of a suitable control.

As a tester strain comprises a host cell comprising a heterologous aaRS gene (i.e., one from a heterologous species), a suitable host cell is heterologous with respect to the species from which the gene to be tested is isolated. For instance, suitable host cells to test *Candida albicans* genes can be host cells of a species other than *C. albicans*. Examples of species which are suitable for use as hosts for the construction of tester strains are *E. coli, B. subtilis*, and *S. cerevisiae*. These species are especially amenable to genetic manipulation because of their history of extensive study.

Suitable host cells having a genotype useful for the construction of a tester strain can be constructed or selected using known methods. For example, both in *E. coli* and in *S. cerevisiae*, a first plasmid which contains a functional copy of a host chromosomal aaRS gene (which is to be inactivated later), and some selectable marker gene, can be constructed and introduced into cells. Then, an inactivating mutation can be caused in the chromosomal copy of the aaRS gene.

This can be accomplished, for instance, by causing or selecting for a double crossover event which creates a deletion and insertion. This can be done by introducing into the cells double-stranded DNA having regions of homology to the DNA flanking the target aaRS gene, and having between these regions a gene encoding a selectable marker, either on a suitable vector or as a DNA fragment, as appropriate (Jasin, et al., U.S. Pat. No. 4,713,337; Schimmel, P., U.S. Pat. No. 4,963,487; Toth, M. J. and Schimmel, P., *J. Biol. Chem.* 261:6643–6646 (1986); Rothstein, R., *Methods in Enzymology* 194:281–301 (1991)). Such an approach simultaneously inserts a selectable marker and results in a deletion of the endogenous gene between the flanking sequences provided. Where needed to maintain viability, a compatible maintenance plasmid is provided encoding an endogenous or complementing aaRS.

A test plasmid which is compatible with the maintenance plasmid, and which contains the aaRS gene to be tested for complementation, can be introduced into the host cells. If the first plasmid has been constructed to have a mechanism to allow for inhibition of its replication (for example, a temperature sensitive replicon) or to have a mechanism by which cells containing the first plasmid can be selected against (by, for example, the use of 5-fluoroorotic acid to select against *S. cerevisiae* cells which have a first plasmid containing the URA3 gene), cells which survive by virtue of having a complementing aaRS gene on the second plasmid can be selected (Sikorsky, R. S. and Boeke, J. D., *Methods in Enzymology* 194:302–318 (1991)).

Causing or selecting for a double crossover event which creates a deletion and insertion can be used in itself as a one-step method of constructing a tester strain in which a native aaRS gene is replaced by the corresponding foreign gene whose gene product is to be tested. Endogenous recombination mechanisms have been used to advantage previously in *E. coli, B. subtilis*, and *S. cerevisiae*, among other organisms. This method depends on the ability of the heterologous gene to be tested to complement the native corresponding aaRS gene. This can be done by introducing into the cells double-stranded DNA having regions of homology to the DNA flanking the target native aaRS gene, and having between these regions a gene encoding a selectable marker as well as the heterologous aaRS gene intended to replace the native aaRS gene. The survival of cells expressing the selectable marker is indicative of expression of the introduced heterologous aaRS gene and complementation of the defect in the endogenous synthetase.

For example, a tester strain useful for testing the effect of a compound on the function of IleRS expressed by an inserted *C. albicans* gene, can be constructed in a one-step method in a suitable host cell. Optional positive and negative controls for this cross-species transformation can be used to show that the resulting strain depends on the IleRS gene from *C. albicans* for growth and that this recombination event is not lethal. For example, *S. cerevisiae* cells can be transformed with a suitable construct, such as a linearized plasmid containing an insert. Generally, the construct includes a selectable marker gene for antibiotic resistance, or other suitable selectable marker. In one embodiment, a linearized plasmid which contains the *C. albicans* IleRS gene and an antibiotic resistance gene, situated between sequences homologous to the flanking sequences of the endogenous IleRS gene of the host cells, is used to transform the host cell. For a positive control, the linearized plasmid can be constructed in a similar fashion, except that the native *S. cerevisiae* IleRS gene replaces the *C. albicans* gene, such that a normal *S. cerevisiae* IleRS gene is located adjacent to the antibiotic resistance marker in the insert. As a negative control, the insert can be designed to contain only the flanking sequences and the antibiotic resistance marker, for example. Antibiotic resistant transformants are not expected upon transformation with the negative control construct, as homologous recombination with the construct results in deletion of the endogenous IleRS gene. Successful construction of a tester strain can also be confirmed by Southern analysis.

In cases of gene duplication (LysU and LysS in *E. coli* a (Kawakami, K., et al., *Mol. Gen. Genet.* 219:333–340 (1989); Leveque, F., et al., *Nucleic Acids Res.* 18:305–312 (1990); Clark, R. L. and Neidhardt, F. C., *J. Bacteriol.* 172:3237–3243 (1990)), or the presence of a cryptic gene (ileZ in *B. subtilis*, Glaser, P., et al., *DNA Sequ. and Mapping* 1:251–61 (1990); Henkin, T. M., et al., *J. Bacteriol.* 174:1299–1306 (1992), a suitable tester strain can be constructed by simultaneous inactivation of both of the host genes, or by sequential inactivation. For instance, inactivation of one host gene by a suitable method, such as by insertion of a selectable marker, can be followed by a one-step gene replacement of the remaining host gene with a heterologous Candida aaRS gene and a second selectable marker.

The yeast *S. cerevisiae* offers additional possibilities for genetic manipulations to create tester strains, relative to bacteria. Yeast integrating plasmids, which lack a yeast origin of replication, can be used for making alterations in the host chromosome (Sikorski, R. S. and Heiter, P., *Genetics* 122:19–27 (1989); Gietz, R. D. and Sugino, A., *Gene* 74:527–534 (1988)). In another embodiment, one-step gene disruptions can be performed in diploid cells using a DNA fragment comprising a copy of an aaRS gene (optionally containing a deletion in the aaRS gene) having an insertion of a selectable marker in the aaRS gene. A suitable fragment can be introduced into a diploid cell to disrupt a chromosomal copy of the yeast gene. Successful integration of the disrupted aaRS gene can be confirmed by Southern blotting and by tetrad analysis of the sporulated diploid cells. The diploid cells heterozygous for the disrupted aaRS gene provide a diploid host strain which can be transformed with a plasmid containing the heterologous aaRS gene. These cells can be sporulated and the haploid spores analyzed for rescue of the defective chromosomal aaRS by the heterologous aaRS gene.

Alternatively, those diploid cells that are found to contain one copy of the disrupted chromosomal aaRS gene, as well as one functional copy, can be transformed with a maintenance plasmid which contains a gene which complements the disruption, such as the corresponding wild type yeast aaRS gene, and which provides for a mechanism to select against survival of the cells containing this plasmid. These cells can then be made to sporulate to obtain a haploid null strain containing the disrupted chromosomal aaRS gene and the wild type gene on the maintenance plasmid. This haploid host strain can then be transformed with a test plasmid which expresses a heterologous aaRS gene, and the maintenance plasmid can be selected against by growing this strain under appropriate conditions.

Construction of a tester strain may start with the isolation of a mutant host strain which produces, for example, an inactive tRNA synthetase specific for a particular amino acid, a tRNA synthetase which is conditionally inactivatible, or which carries a chromosomal deletion of a tRNA synthetase. A number of *E. coli* and *S. cerevisiae* strains have been described that can be used for constructing tester strains. Some of these strains are described below for illustrative purposes. The procedures used to isolate and/or construct these *E. coli* and *S. cerevisiae* strains, or similar procedures, can be used or adapted to make additional mutant strains in *E. coli*, *S. cerevisiae* or other host organisms.

*E. coli* strains having a defect, such as a null mutation, in an aminoacyl-tRNA synthetase gene can be constructed using a cloned *E. coli* aaRS gene. Each aminoacyl-tRNA synthetase from *E. coli* has been cloned (see Meinnel, T., et al., 1995, "Aminoacyl-tRNA Synthetases: Occurrence, Structure and Function," In: *tRNA: Structure, Biosynthesis and Function*, Söll, D. and RajBhandary, U., Eds., (American Society for Microbiology: Washington, D.C.), Chapter 14, pp. 251–292, the teachings of which are incorporated herein by reference). The cloned genes can be incorporated into a suitable construct and be used as maintenance plasmids in a suitable host cell.

A number of *E. coli* strains have been characterized in which an aaRS gene has been inactivated by some method, in whole or in part, yielding an observable phenotypic defect which can be detectably complemented. For example, null strains in which the gene encoding IleRS has been inactivated (IQ843, IQ844, see Shiba, K. and Schimmel, P., *J. Biol. Chem.* 267:22703–22706 (1992)), and a mutant strain (MI1, see Starzyk, et al., *Science* 237:1614–1618 (1987) and Iaccarino and Berg, *J. Bacteriol.* 105:527–537 (1970)) having an isoleucine auxotrophy due to an elevated $K_m$ for isoleucine of the enzyme encoded by the chromosomal ileS allele, have been described.

*E. coli* strain IQ843/pRMS711 and its derivative IQ844/pRMS711 contain a chromosomal deletion of the ileS gene (ΔileS203::kan), and are propagated by expression of wild type IleRS at 30° C. from a temperature-sensitive maintenance plasmid designated pRMS711, which encodes the wild type ileS gene and a gene which confers chloramphenicol resistance. pRMS711 cannot replicate at 42° C., thus, at the non-permissive temperature, the maintenance plasmid is lost. Following the introduction of a test construct into these strains, the growth of chloramphenicol sensitive colonies at a non-permissive temperature (e.g., 42° C.) is indicative of complementation of the chromosomal ileS deletion by the introduced construct (Shiba, K. and Schimmel, P., *Proc. Natl. Acad. Sci. USA* 89:1880–1884 (1992); Shiba, K. and Schimmel, P., *Proc. Natl. Acad. Sci. USA* 89:9964–9968 (1992); Shiba, K. and Schimmel, P., *J. Biol. Chem.* 267:22703–22706 (1992)).

Temperature sensitive alleles are examples of genes encoding conditionally inactivatable tRNA synthetases. For example, temperature-sensitive alleles of the genes encoding cytoplasmic IleRS (ils1-1) and MetRS (mes1-1) have been described in *S. cerevisiae* (Hartwell, L. H., and McLaughlin, C. S., *J. Bacteriol.* 96:1664–1671 (1968); McLaughlin, C. S., and Hartwell, L. H., *Genetics* 61:557–566 (1969)), and are available from the Yeast Genetic Stock Center (University of California-Berkeley; catalog nos. 341 and 19:3:4, respectively).

The *S. cerevisiae* genome has been fully sequenced and all of the aminoacyl-tRNA synthetases have been identified. The KRS1 gene was shown to be essential by the construction of a disrupted allele of KRS1 (Martinez, R., et al., *Mol. Gen. Genet.* 227:149–154 (1991). For construction of a tester strain in *S. cerevisiae*, a plasmid such as the one reported by P. Walter, et al. (*Proc. Natl. Acad. Sci. USA* 80:2437–2441, (1983)), which contains the wild type cytoplasmic methionyl-tRNA synthetase gene of *S. cerevisiae*, MES1, can be used to construct mes1 strains, and for the construction of maintenance plasmids to create cytoplasmic tester strains for a MetRS (see also Fasiolo, F., et al., *J. Biol. Chem.* 260:15571–15576 (1985)).

Strains having a defect in mitochondrial aminoacyl-tRNA synthetase can be constructed using a cloned mitochondrial aaRS gene, and used to make tester strains (see Meinnel, T. et al., 1995, "Aminoacyl-tRNA synthetases: Occurrence, Structure and Function", In: *tRNA: Structure, Biosynthesis and Function*, Söll, D. and RajBhandary, U, Eds., American Society for Microbiology: Washington, D.C., Chapter 14, pp. 251–292; also see ATCC Catalog of Recombinant DNA Materials, American Type Culture Collection, Rockville, Md., regarding mitochondrial aaRS genes. For example, an *S. cerevisiae* strain has been constructed which carries a disruption of MSY1, the gene encoding mitochondrial isoleucyl-tRNA synthetase. Plasmids carrying MSY1 which rescue this defect, also have been constructed (Hill, J. and Tzagoloff, A., Columbia University; see Edwards, H. and Schimmel, P., *Cell* 51:643–649 (1987)).

In *S. cerevisiae*, to construct a maintenance plasmid or a test plasmid carrying a heterologous gene, a suitable vector, such as a yeast centromere plasmid (CEN; single-copy) or 2μ vector (high copy) can be used. A heterologous gene to be tested can also be incorporated into the chromosome, using an integrating plasmid, for example. Examples of convenient yeast vectors for cloning include vectors such as those in the pRS series (integrating, CEN, or 2μ plasmids differing in the selectable marker (HIS3, TRP1, LEU2, URA3); see Christianson, T. W., et al., *Gene* 110:119–122 (1992) regarding 2μ vectors; see Sikorski, R. S. and Hieter, P., *Genetics* 122:19–27 (1989) regarding integrating and CEN plasmids which are available from Stratagene, La Jolla)) and shuttle vectors (integrating, CEN or 2μ vectors) which contain the multiple cloning site of pUC19 (Gietz, R. D. and Sugino, A., *Gene* 74:527–534 (1988)). Examples of expression vectors include pEG (Mitchell, D. A., et al., *Yeast* 9:715–723 (1993)) and pDAD1 and pDAD2, which contain a GAL1 promoter (Davis, L. I. and Fink, G. R., *Cell* 61:965–978 (1990)).

A variety of promoters are suitable for expression. Available yeast vectors offer a choice of promoters. In one embodiment, the inducible GAL1 promoter is used. In another embodiment, the constitutive ADH1 promoter (alcohol dehydrogenase; Bennetzen, J. L. and Hall, B. D., *J. Biol. Chem.* 257:3026–3031 (1982)) can be used to express an inserted gene on glucose-containing media. An example of a vector suitable for expression of a heterologous aaRS gene in yeast is pQB169 (Example 7).

For illustration, a yeast tester strain can be constructed as follows. A *Saccharomyces cerevisiae* strain with convenient markers, such as FY83 (MATa/MATα lys2-128δ/lys2-128δ leu2Δ1/leu2Δ1 ura3-52/ura3-52 trp1Δ63/trp1Δ63) can be used as a host cell.

A nucleic acid encoding a yeast cytoplasmic aaRS can be used to create a null allele of the yeast cytoplasmic aaRS gene. For example, a deletion/insertion allele can be constructed by excising the aaRS open reading frame, including the promoter region and 3' flanking region or portions thereof from a cloned gene, and replacing the excised sequence with a selectable marker (e.g., TRP1). This aaRS::TRP1 fragment can be used to transform the diploid strain FY83, and Trp$^+$ transformants can be selected (Rothstein, J., *Methods in Enzymol.* 101:202–211 (1983)). Standard genetic procedures can be employed to identify the appropriate integrant created by this one-step gene disruption (a diploid having the genotype MATa/MATα lys2-128δ/lys2-128δ leu2Δ1/leu2Δ1 ura3-52/ura3-52 trp1Δ63/trp1Δ63 aaRS::TRP1/aaRS); Rose, M. D., et al., *Methods in Yeast Genetics*, 1990, Cold Spring Harbor Press, Cold Spring Harbor, N.Y.).

To construct a maintenance plasmid, a fragment containing the aaRS coding region, its promoter and some of the 3' untranslated region (e.g., a region approximately equivalent to that deleted in the construction of the null allele above) can be excised and introduced into a vector such as YCplac33, a CEN plasmid containing a URA3 selectable marker (Gietz, R. D. and Sugino, A., *Gene* 74:527–534 (1988)). The resulting plasmid can be used to transform the aaRS::TRP1/aaRS diploid described above, and Ura$^+$ transformants which contain the maintenance plasmid can be selected. The resulting diploid can be sporulated and a haploid Trp$^+$Ura$^+$ spore (an aaRS null strain), corresponding to a aaRS::TRP1 strain dependent upon the URA3-aaRS maintenance plasmid can be isolated.

To construct a test plasmid (a plasmid bearing a heterologous tRNA synthetase gene to be tested for its ability to complement the defect in the endogenous yeast gene), a heterologous aaRS gene to be tested can be inserted into a suitable vector for expression. For instance, the multicopy vector pQB169 described in Example 7 can be used. A fragment containing the *C. albicans* aaRS gene can be inserted into pQB169, using one or more suitable restriction sites in the multiple cloning site, for example. Alternatively, to test whether a relatively reduced level of expression of the heterologous tRNA synthetase gene permits complementation, a fragment containing the *C. albicans* aaRS gene can be inserted into a CEN plasmid such as pQB172 (Example 7) for expression. Preferably, the heterologous gene is inserted into the vector so that its ATG start codon is the first ATG within 50 to 100 bp of the transcription start site of the ADH promoter of the vector.

Because these plasmids bear the LEU2 selectable marker, they can be used to transform a null strain, such as the Trp$^+$Ura$^+$Leu– strain described, and Leu$^+$ transformants containing the test plasmid can be selected. Leu$^+$Ura$^+$Trp$^+$ transformants (containing a aaRS::TRP1 allele, a URA3 maintenance plasmid, and the LEU2 test plasmid) can be tested for growth on media containing 5-fluoroorotic acid (5-FOA). 5-FOA is toxic to URA3 cells, and causes loss of the URA3 maintenance plasmid (Boeke, J., et al., *Mol. Gen. Genet.* 197:345–346 (1984)). Accordingly, growth of cells on media containing 5-FOA is indicative of complementation of the lethal deletion in the aaRS gene on the chromosome (aaRS::TRP1) by the heterologous aaRS gene on the test plasmid. Cells that are unable to grow on 5-FOA are dependent upon the maintenance plasmid for viability, and therefore, are indicative of insufficient activity to complement the lethal deletion in the aaRS gene. Where complementation is observed, the strain can be used to test for inhibitors of the product of the heterologous gene encoded by the test plasmid.

In another embodiment, a eucaryotic host cell is used to construct a mitochondrial tester strain. For example, in yeast, each of the mitochondrial tRNA synthetases is essential for growth on non-fermentable carbon sources (e.g., glycerol). Thus, complementation tests can be conducted in mitochondrial tester strains. As the genes encoding mitochondrial aminoacyl-tRNA synthetases are typically nuclear-encoded, the procedures described above can be modified to construct mitochondrial tester strains having a defect in a mitochondrial aminoacyl-tRNA synthetase. Modification is necessitated by the fact that yeast strains with a defect in mitochondrial protein synthesis, such as a defective aminoacyl-tRNA synthetase, lose their mitochondrial DNA, rapidly becoming rho$^-$. As a result, these strains are unable to grow on non-fermentable carbon sources even if a complementing gene is introduced into the strain. Therefore, in a haploid strain having a defect in, for example, the yeast mitochondrial isoleucyl-tRNA synthetase gene (e.g., a gene disruption with a cosegregating selectable marker constructed as indicated above; see also Tzagoloff, A., et al., *J. Biol. Chem.* 263(2): 850–856 (1988)), the haploid strain can be crossed with a rho$^+$ strain having a wild-type mitochondrial isoleucyl-tRNA synthetase gene to restore the mitochondrial DNA. The resulting rho$^+$ diploid can then be transformed with a plasmid which encodes the wild-type yeast mitochondrial isoleucyl-tRNA synthetase (i.e., a maintenance plasmid) and a second selectable marker. Following sporulation, progeny spores which carry the defective mitochondrial IleRS, identified by the presence of the cosegregating selectable marker, and the maintenance plasmid, identified by the presence of the second selectable marker, and which are rho$^+$, can be isolated (e.g., by tetrad analysis). Strains constructed in this manner would be suitable for complementation assays using Candida isoleucyl-tRNA synthetases.

For instance, a plasmid encoding a Candida isoleucyl-tRNA synthetase gene can be introduced into such a strain on a second plasmid having a third selectable marker. As indicated above, the maintenance plasmid can be selected against (e.g., where the selectable marker is URA3, selection on 5-fluoroorotic acid leads to loss of the maintenance plasmid), and complementation by the Candida gene can be monitored on a non-fermentable carbon source.

In another embodiment, a mitochondrial isoleucyl-tRNA synthetase gene disruption with a cosegregating selectable marker can be constructed in a diploid rho$^+$ strain (see e.g., Edwards, H. and Schimmel, P., *Cell* 51:643–649 (1987)). A plasmid encoding a Candida isoleucyl-tRNA synthetase gene is introduced on a plasmid having a second selectable marker. Sporulation of a resulting diploid yields two progeny spores carrying the yeast mitochondrial isoleucyl-tRNA synthetase gene disruption, identified by the presence of a cosegregating selectable marker, and two progeny spores carrying the corresponding wild-type gene. The presence of the plasmid can be monitored by the presence of the second selectable marker. Complementation by the Candida gene on the introduced plasmid is indicated by growth on non-fermentable carbon sources of spores carrying the disrupted isoleucyl-tRNA synthetase gene.

In the case of a mitochondrial tester strain, the Candida aminoacyl-tRNA synthetase can be imported into mitochondria to achieve complementation of the mitochondrial defect. When it is necessary to achieve import or desirable to improve the efficiency of import of the aminoacyl-tRNA synthetase in the host cell, a gene fusion can be constructed using a sequence encoding a mitochondrial targeting sequence which functions in the host cell. For example, a mitochondrial targeting sequence can be introduced at the amino-terminal end of the Candida aminoacyl-tRNA synthetase. In one embodiment in yeast, the Candida aaRS gene or a sufficient portion thereof is introduced into a vector in which it is placed under the control of the minimal alcohol dehydrogenase promoter and is fused to the yeast cytochrome oxidase IV targeting signal derived from plasmid pMC4 (Bibus, et al., *J. Biol. Chem.* 263:13097 (1988)). Expression of the construct yields a fusion protein with an N-terminally located cytochrome oxidase IV targeting signal joined to the Candida aaRS protein.

If the construction methods described here are not successful initially, one or more natural or synthetic Candida or other (e.g., procaryotic, such as a bacterial, or eukaryotic, such as a mammalian or fungal) tRNA gene(s) can be introduced into the host cell to provide one or more cognate tRNAs for the Candida aaRS. The tRNA genes of a number of species have been cloned and sequenced (Steinberg, S., et al., "Compilation of tRNA sequences and sequences of tRNA genes", *Nucleic Acids Res.* 21:3011–3015 (1993)). A method for constructing a strain of *Streptomyces lividans* in which an essential tRNA gene has been inactivated in the chromosome, and the gene is instead maintained on a plasmid, has been described (Cohen, S. N., WO 94/08033 (1994)).

Use of Tester Strains

To assess the inhibitory effect of a substance on a tester strain, the cells are maintained under conditions suitable for complementation of the host cell defect, under which complementation of the host cell defect is dependent upon the test gene (i.e., assay conditions). A substance to be tested is administered to the tester cells, and the viability or growth of the tester cells can be compared with that of cells of one or more suitable controls. A variety of control experiments can be designed to assess the inhibitory effect of a substance and/or the specificity of inhibition. The following examples are provided for purposes of illustration.

A preliminary test for inhibitory effect may be conducted where desired. For example, a substance to be tested can be administered to tester cells maintained under assay conditions, and the viability or growth of the tester cells in the presence of the substance can be compared with that of tester cells maintained under the same conditions in the absence of the substance. If it is determined that the substance inhibits growth of the tester cells, a further assessment of the specificity of inhibition by the substance can be conducted as described below.

Alternatively, the inhibitory effect of a substance on tester cell growth and the specificity of inhibition can be determined without conducting the preliminary test for inhibitory activity. The following examples, in which the various cell types are in each case exposed to drug, are provided for purposes of illustration only.

To determine the specificity of inhibition, the viability or growth of the tester cells can be compared with that of cells of one or more suitable control strains maintained under the same conditions. In particular, tester strains and control strains are maintained under assay conditions, and exposed to the substance to be tested.

Strains which are similar to the tester strain, but lack the heterologous aminoacyl-tRNA synthetase gene present in the tester strain (i.e., the "test gene"), can serve as control strains. These control strains comprise a "control gene" which is an aminoacyl-tRNA synthetase gene other than the heterologous Candida aaRS gene present in the tester strain (i.e., an aaRS gene from a different species, such as a procaryotic or eukaryotic species). The control gene can be a cytoplasmic or mitochondrial aaRS gene, and it encodes an aaRS specific for the same amino acid as the aaRS encoded by the test gene. Viability or growth of the control strain is dependent upon the control gene under the conditions of the assay.

In one embodiment, a cell which is a cell of the same species as the host cell used to construct the tester strain, and which further comprises a control aaRS gene, is selected as a control. For example, the control gene can be a wild-type aaRS gene from the control strain species which encodes an aaRS specific for the same amino acid as the aaRS encoded by the test gene. Such a cell can be used when, for example, the substance or compound to be tested does not significantly affect growth of the control strain under the assay conditions. For example, where an *E. coli* host is used to construct a tester strain having a *C. albicans* aaRS gene, an *E. coli* strain having a wild-type *E. coli* control gene can be used as a control strain. As another example, if a yeast host cell having a defect in a mitochondrial aaRS gene is used to construct the tester strain, a yeast strain comprising the wild type mitochondrial gene can be used as a control strain.

In another embodiment, the control strain can be a strain distinct from the tester strain, which is constructed in a manner which generally parallels that of the tester strain comprising the test gene, such that complementation of the host cell defect, which is also present in the control strain, is dependent upon the control gene under the assay conditions. In this embodiment, the control strain preferably comprises a host cell of the same species as the host cell used to construct the tester strain, and is closely related in genotype to the tester strain. These preferred control strains comprise a "control gene," which, as indicated above, is an aaRS gene other than the test gene (i.e., an aaRS gene from a different species, such as a heterologous procaryotic or eukaryotic species). Furthermore, the control gene, which can be cytoplasmic or mitochondrial, encodes an aaRS specific for the same amino acid as the test gene. Preferably, the control gene is selected from a species which is a host for the pathogen from which the test gene is derived, permitting the identification of specific inhibitors which selectively inhibit the pathogen aaRS (e.g., human control gene for an *C. albicans* test gene). Alternatively, because the eukaryotic aminoacyl-tRNA synthetases are generally more closely related to each other than to procaryotic aminoacyl-tRNA synthetases, a control gene from another eukaryote (e.g., a different mammalian species) can be used in lieu of one selected from the host species (e.g., a rat or mouse control gene for an *C. albicans* test gene).

For example, a strain isogenic with a tester strain, except for the substitution of a human control gene, can serve as a control strain. Such a control strain can be constructed using the same methods and the same host cell used to construct the tester strain, with the exception that a human control gene is introduced into the host cell in lieu of the heterologous Candida aaRS gene present in the tester.

Under the conditions of this assay, growth or viability of the control strain is dependent upon the control aaRS gene, which complements the host cell aaRS defect in the control strain. Specific inhibition by a substance can be determined by comparing the viability or growth of the tester strain and control strain in the presence of the substance.

In some cases, further controls may be desired to assess specific inhibition. For this purpose, one or more additional "comparison control" strains are used for purposes of comparison. These additional controls can be used to assess the relative effects of a substance upon growth of the tester and control strains in the presence of the substance.

Strains useful for this purpose include, for example, strains of the same species as the host cell used to construct the tester strain, which contain a wild type version of the aaRS gene which is inactivated in the tester strain. In one embodiment, where an *E. coli* host is used to construct a tester strain comprising a *C. albicans* test gene, an *E. coli* strain comprising a wild-type *E. coli* aaRS gene can be used as a comparison control strain. In another embodiment, "parental-type" cells (e.g., parent host cells or a similar strain) are used as comparison controls. For example, the parent host cells of the tester strain can serve as a comparison control strain for the tester strain. Where the tester strain and the control strain have the same parent, a single strain can be used as the comparison control strain for both tester and control strains.

For example, a parent host cell from which the tester and control strains were both constructed (e.g., by inactivation and replacement of the wild type host aaRS gene) can be used as a comparison control strain. This comparison control strain contains a wild type version of the aaRS gene which is inactivated in the tester and control strains, and the viability or growth of this comparison control strain is dependent upon the wild type aaRS under the conditions of the assay. Specific inhibition of the heterologous Candida aaRS encoded by the test gene (or a step in the expression of the Candida gene) is indicated if, after administering the substance to the tester strain, growth of the tester strain is reduced as compared with an appropriate comparison control strain, and growth of the control strain is not reduced, or is relatively less reduced, as compared with its appropriate comparison control strain.

Testing for Antibiotic Resistance to tRNA Synthetase Inhibitors

Mutation of a drug target can reduce the effectiveness of antimicrobial or antibiotic agents, and can confer drug resistance. Thus, mutation of a target aminoacyl-tRNA synthetase, such as a *C. albicans* IleRS, could reduce the effectiveness of an inhibitor of aaRS activity. To test for mutations that confer resistance to an inhibitor (e.g., an inhibitor of aaRS activity, including such an inhibitor having antimicrobial activity) a variety of approaches can be used. Mutant Candida aaRS genes can be obtained, for example, by isolation of a mutant gene, or by preparing an individual mutant gene or an expression library of mutant Candida aaRS genes, such as a library of mutants of a *C. albicans* IleRS gene. The mutant gene or gene library can be introduced into suitable host cells for screening for resistance to a compound.

An isolated tRNA synthetase gene, such as a *C. albicans* aaRS gene, can be mutagenized by any suitable method including, but not limited to, cassette mutagenesis, PCR mutagenesis (e.g., the fidelity of PCR replication can be reduced to induce mutation by varying $Mg^{2+}$ concentration, increasing the number of amplification cycles, altering temperatures for annealing and elongation, to yield random mutants), or chemical mutagenesis (e.g., nitrosoguanidine, ethylmethane sulfonate (EMS), hydroxylamine) of the entire gene or a portion thereof. The mutagenesis products can be used to construct an expression library of mutant genes (e.g., by inserting the gene into an expression vector, or replacing a portion of an expression vector comprising the wild-type gene with mutant fragments) which is introduced into a host cell.

In one embodiment, if the inhibitor is known to inhibit the host cell (e.g., *E. coli*, yeast, *Bacillus subtilis*) aminoacyl-tRNA synthetase specific for the same amino acid, the mutant genes can be introduced into the wild-type host and the resulting cells can be exposed to drug to assess resistance.

In another embodiment, the procedures described above relating to tester strains are used in the method to identify mutants resistant to inhibitor. Introduction of the heterologous mutant aaRS gene(s) (i.e., mutant test gene(s)) into a host cell is carried out as described above for the production of tester strains. Using MetRS as an example, the library can be introduced into a host cell having a defect in the endogenous gene encoding MetRS. The metG null strain of *E. coli* designated MN9261/pRMS615 is an example of the type of strain that can be constructed and used as a host for the introduction of mutant Candida aaRS gene(s) (in that case, MetRS genes; see Kim, et al., *Proc. Natl. Acad. Sci. USA* 90:10046–10050 (1993), describing a strain which carries a null allele of metG, and a temperature sensitive maintenance plasmid, carring a wild type metG allele (encoding *E. coli* MetRS) and having a temperature sensitive replicon which causes loss of the maintenance plasmid at the non-permissive temperature).

Active, drug-resistant mutants are then identified by a selection process in which cells containing mutant genes encoding active aaRS are identified, and the effect of an inhibitor upon aaRS activity is assessed. Cells are maintained under conditions suitable for expression of the mutated gene, and cells containing an active mutant aaRS (e.g., an active recombinant *C. albicans* IleRS) are identified by complementation of the host cell defect. Where complementation occurs, each resulting transformant is, in essence, a tester strain comprising a mutant test gene. Cells containing active mutant aaRS as determined by complementation of the host cell defect are then exposed to inhibitor, and the effect of inhibitor on cell growth or viability is assessed to determine whether the active mutant aaRS further confers resistance to inhibitor.

In the case of the metG null strain, complementation by the Candida gene is indicated by growth at the non-permissive temperature at which the maintenance plasmid is lost. Cells which survive loss of the maintenance plasmid due to the presence of the complementing mutant gene are then challenged with inhibitor to assess resistance. Resistance can be assessed by comparison to a suitable control by methods analogous to those described above for determining inhibition and/or the specificity of inhibition of a substance in tester cells. For example, the relative effects of an inhibitor upon a tester strain comprising the mutant test gene and upon a tester strain differing only in that it contains the test gene lacking the mutation, can be assessed by comparing the viability or growth of cells which are dependent upon either the test gene or mutant test gene for growth under conditions suitable for complementation of the host cell defect. For instance, the effect of inhibitor on the protein encoded by the test gene lacking the mutation can be determined by comparing the growth of cells containing the test gene in the presence of drug to the growth of such cells in the absence of drug, and the effect of inhibitor on the protein encoded by a mutant test gene can be determined by comparing growth of cells containing the mutant test gene in the presence of drug to the growth of such cells in the absence of drug. A decrease in the inhibitory effect on growth of cells carrying the mutant test gene as compared to the inhibitory effect against cells carrying the test gene lacking the mutation is indicative of resistance.

Cells containing a complementing mutant test gene which further confers resistance to an inhibitor can be used to identify derivatives of the inhibitor with improved antimicrobial effect, which circumvent resistance. Such cells can also be used to identify additional inhibitors having inhibitory activity against the active mutant aaRS encoded by the mutant test gene.

In another embodiment, a naturally occurring mutant Candida aaRS gene which confers resistance to an inhibitor upon a Candida cell, can be isolated from the Candida organism using nucleic acids of the present invention as probes. The cloned gene can then be introduced into a host cell as described for the production of tester strains. Tester cells comprising the mutant test gene which confers resistance, and which complements the host defect, can be used as described herein to identify additional inhibitors having reduced susceptibility to the resistance mutation or derivatives of the inhibitor with improved inhibitory activity.

Vectors carrying mutant genes which confer resistance to inhibitor can be recovered and the insert analyzed to locate and identify the mutation by standard techniques, such as DNA sequence analysis, to yield additional information regarding the nature of mutations capable of conferring resistance to selected inhibitors. Mutant proteins can also be expressed and purified for further characterization by in vitro kinetic and binding assays.

Applications in Biochemistry

The Candida isoleucyl-tRNA synthetase or stable subdomains of the protein can be used in a method to separate isoleucine from a mixture of isoleucine and other compounds such as other amino acids, or to specifically isolate L-isoleucine from D-isoleucine. The isoleucyl-tRNA synthetase can be chemically attached to a solid support material packed in a column or other suitable container. Alternatively, a fusion protein, such as a GST-tRNA synthetase fusion or a His tag-tRNA synthetase fusion (having a histidine hexamer tail), can permit attachment to a suitable solid support which binds the GST portion or His tag portion of the fusion protein, respectively. For example, a mixture of isoleucine and other compounds can be loaded onto a column under conditions in which isoleucine binds to isoleucyl-tRNA synthetase, while other compounds present in the mixture flow through the column. In a later step, isoleucine can be released from isoleucyl-tRNA synthetase by changing the conditions in the column, such as washing with a solution of high ionic strength to elute L-isoleucine, for example.

In a similar manner, the isoleucyl-tRNA synthetase can be used in a method to isolate tRNA that is specifically recognized by the tRNA synthetase.

The Candida isoleucyl-tRNA synthetase can be used in the quantitative determination of isoleucine by its conversion to the corresponding aminoacyl-hydroxamate (isoleucyl-hydroxamate). An example of an appropriate assay is illustrated by the following series of reactions.

$$\text{isoleucine} + ATP \rightarrow \text{isoleucine} - AMP + PP_i$$

(in the presence of excess pyrophosphatase and ATP at pH 7.5, where pyrophosphatase catalyzes the conversion of the product inorganic pyrophospate ($PP_i$) to inorganic orthophospate ($P_i$); ATP is adenosine triphospate; AMP is adenosine monophosphate)

$$\text{isoleucine} - AMP + NH_2OH \rightarrow \text{isoleucine} - NHOH + AMP \text{ (at pH 7.5)}$$

$$\text{isoleucine} - NHOH + FeCl_3 \rightarrow \text{colored complex (at acidic pH)}$$

The resulting colored complex can be quantitated by spectrophotometric measurements of absorbance at 540 nm, and compared with a standard curve made using known concentrations of isoleucine. This assay is based on the reactions described by Stulberg and Novelli, *Methods in Enzymology* 5:703–707 (1962).

The Candida isoleucyl-tRNA synthetases can also be used for the quantitative determination of ATP. In the presence of excess amino acid such as isoleucine, and in the presence of pyrophosphatase to convert the product $PP_i$ to $P_i$, the ATP is quantitatively converted to AMP and inorganic pyrophosphate by the isoleucyl-tRNA synthetase. For example, $$\text{isoleucine} + ATP \;\; \text{isoleucine} - AMP + PP_i \text{ (in the presence of IleRS)}$$

$$PP_i + H_2O \rightarrow 2P_i \text{ (in the presence of pyrophosphatase)}$$

$P_i$ can be quantitated by reaction with molybdate, measuring the absorbance at 580 nm and comparing to a standard curve made using known quantities of orthophosphate.

Exemplification

The present invention will now be illustrated by the following Examples, which are not intended to be limiting in any way.

Materials and Methods

All restriction enzymes were purchased from New England Biolabs (Beverly, Mass.) unless otherwise stated. Ultrapure deoxynucleotide triphosphates (dNTPs) were purchased from Pharmacia. Overnight refers to more than 8 hours (up to 16 hours). Radioactive compounds were purchased from Dupont NEN. All bacterial transformations were done with the $CaCl_2$ procedure, unless otherwise stated. Sequencing was done using the Sequenase kit from USB. Procedures for standard techniques (e.g. bacterial transformation) and reagent preparation (e.g. TAE buffer) were done as described in Sambrook, J., et al., *Molecular Cloning: A Laboratory Manual*, 2nd Ed., Cold Spring Harbor Laboratory, Cold Spring Harbor, N.Y. (1989). Media for yeast cultures and experimental techniques used for yeast manipulations were as described in *Methods in Yeast Genetics: A Laboratory Manual* Rose, M. D., F. Winston and P. Hieter, eds., Cold Spring Harbor Laboratory Press, Cold Spring Harbor, N.Y. (1990).

Abbreviations

PCR=polymerase chain reaction; ORF=open reading frame; IPTG=isopropyl-β-D-thio-galactopyranoside; LB=Luria Broth EDTA=ethylenediaminetetraacetic acid; DTT=dithiothreitol; PBS=phosphate buffered saline; BSA= bovine serum albumin; TCA=tricholoracetic acid; IPTG= isopropyl-β-D-thiogalactoside; 5-FOA=5-fluoroorotic acid; SDS=sodium dodecyl sulfate

EXAMPLE 1

PCR Amplification of DNA Fragments of Isoleucyl-tRNA Synthetase Genes From *C. albicans* Genomic DNA PCR was used to obtain DNA fragments of isoleucyl-tRNA synthetase (IleRS) genes using genomic DNA from *C.*

*albicans* strain SC5314 as template (Gillum, A. et al., *Mol. Gen. Genet.* 198:179–182 (1984); a gift of Brendan Cormack, Stanford University). The PCR primers were designed to contain coding sequences for highly conserved regions in IleRSs. Conserved regions were found by aligning the amino acid sequences of IleRSs from several different organisms, using the PILEUP program (Needleman and Wunsch, *J. Mol. Biol.* 48:443–453, 1970). From the aligned sequences, the "distances" between any two selected sequences, the evolutionarily conserved residues, and the average similarity among all members at each position were calculated using the DISTANCE, the PRETTY and the PLOTSIMILARITY programs, respectively. These programs, designed by the Genetics Computer Group (Madison, Wis.), use the modified Dayhoff comparison table (Gribskov and Burgess, *Nucleic Acids Res.* 14: 6745–6763 (1986)) for calculation.

The following sequences retrieved from GenBank were used in the multiple alignments of IleRS amino acid sequences: *T. thermophila* (Csank, C., et al., *J. Biol. Chem.* 267:4592–4599 (1992)), *S. cerevisiae* (Englisch, U., et al., *Biol. Chem. Hoppe-Seyler* 368:971–979 (1987)), *M. thermoautotrophicum* (Jenal, U., et al., *J. Biol. Chem.* 266:10570–10577 (1991)), and *E. coli* (Webster, T. A., et al., *Science* 226:1315–1317 (1984)). *T. thermophilus* (Kiyotaka Shiba) was also used in the multiple alignment.

Several conserved regions were chosen for the design of degenerate oligonucleotides which were used to generate PCR fragments of the *Candida albicans* IleRS gene. Table 1 shows the sequence of the degenerate oligonucleotide primers used for PCR amplification of the *C. albicans* isoleucyl-tRNA synthetases.

EXAMPLE 2

Cloning and Characterization of the PCR Products

The PCR products were visualized following electrophoresis on an agarose gel and staining with ethidium bromide. PCR fragments with the expected sizes were purified using a GeneClean II kit (Bio 101, LaJolla, Calif.), and ligated into pT7Blue T-Vector (Novagen, Madison, Wis.). The ligation mixtures were used to transform *E. coli* DH5α competent cells which were then spread on LB agar plates containing 100 μg/ml ampicillin, 50 μg/ml X-Gal (5-bromo-4-chloro-3-indolyl-β-D-galactoside) and 1 mM IPTG. White colonies were screened by direct colony PCR using vector specific reverse (U19) and forward (T7) primers to detect the presence and size of inserts. Colonies containing inserts of the expected size were used to inoculate 3 ml of LB containing 100 μg/ml ampicillin and the cultures were incubated at 37° C. overnight to produce cells for plasmid DNA isolation. Plasmid DNA was purified using the Wizard kit (Promega, Madison, Wis.), and the sequences of the inserts were determined by the dideoxy method using the USB Sequenase kit with 7-deaza-G (7-deaza-2'-deoxyguanosine-5'-triphosphate labeling mix).

Querying the sequences of the PCR products against the GenBank and the Swiss Protein Bank databases using the DNASTAR program and the BLAST program at the National Center for Biotechnology Information (NCBI), confirmed that the sequences of the PCR fragments encoded polypeptides having amino acid sequences similar to known isoleucyl-tRNA synthetase amino acid sequences. The sequences were most similar to those of cytoplasmic IleRSs

TABLE 1

Sequences of Degenerate PCR Primers Used for Amplification of *C. albicans* Isoleucyl-tRNA Synthetases

| PRIMER NAME | SEQ ID | PRIMER SEQUENCE (5'->3') |
|---|---|---|
| KIYO-16 | 3 | <u>GCG AAT TCG</u> GIT GGG AYA CIC AYG GIS TIC C |
| KIYO-17 | 4 | <u>GCG AAT TCG</u> GIT GGG AYT GYC AYG GIC TIC C |
| KIYO-18 | 5 | <u>GCG AAT TCG</u> ICA RCG ITA YTG GGG IRT ICC IAT |
| KIYO-19 | 6 | <u>GCG AAT TCG</u> IAA YCG ITW YTG GGG IAC ICC IMT |
| KIYO-20 | 7 | <u>GCG AAT TCR</u> AAC CAI CCI CGI GTY TGR TCI WWI CCY TC |
| KIYO-36 | 8 | GGI ARI GTC CAI GGI GTI GTI GTC CA |
| KIYO-37 | 9 | TWY ATG GAR TCI ACI TGG TGG GYI TTI AAR CA |

R = A or G, Y = C or T, M = A or C, W = A or T, S = G or C, H = A, T, or C, K = G or T; I = inosine; underlined bases were introduced to generate an *Eco*RI restriction site and are not present in the gene. Primer names are sometimes abbreviated, as in Table 2, to K-16, K-17, etc.

Unless otherwise stated, each PCR described in the exemplification using degenerate oligonucleotides as primers was done in a 50 μl volume with 15 ng of *Candida albicans* genomic DNA from strain SC5314 (provided by Brendan Cormack, Stanford University), 100 pmoles of each primer, 1 mM Tris-HCl pH 8.3, 150 μM MgCl$_2$, 5 mM KCl, 10 μg/ml gelatin, 50 μM of each dNTP, and 1.25 units of Taq DNA polymerase (Boehringer Mannheim). The reactions were performed in a PTC-100 thermal cycler (M J research, Inc. Watertown, Mass.) for 30 cycles (94° C. for 30 seconds, 55° C. for 30 seconds, 72° C. for 70 seconds, followed by a 4 minute extension at 72° C.).

of eucaryotes, rather than mitochondrial or bacterial IleRSs. Results of the query are summarized in Table 2.

TABLE 2

RESULTS OF PCR AMPLIFICATIONS USING COMBINATIONS OF DEGENERATE PRIMERS DEFINED IN TABLE 1

| Primer Combination/ Fragment | Expected Size (bp) | PCR Product | Origin | Highest Similarity |
|---|---|---|---|---|
| K-17/K-36 | 450 | + | cytoplasmic | *S. cerevisiae* cytoplasmic |
| K-16/K-17/K-20 | 1500 | + | cytoplasmic | *S. cerevisiae* |

TABLE 2-continued

RESULTS OF PCR AMPLIFICATIONS USING COMBINATIONS OF DEGENERATE PRIMERS DEFINED IN TABLE 1

| Primer Combination/ Fragment | Expected Size (bp) | PCR Product | Origin | Highest Similarity |
|---|---|---|---|---|
| | | | | cytoplasmic |
| K-18/K-19/K-20 | | – | | |
| K-16/K-36 | 450 | + | cytoplasmic | S. cerevisiae cytoplasmic |
| K-37/K-20 | | – | | |
| K-36/K-37 | | – | | |

EXAMPLE 3

Screening of C. albicans Genomic Libraries

A. Synthesis of specific DNA probes

From the sequencing information obtained from the PCR products of Example 2, specific oligonucleotides were designed (see Table 3) and used to generate a specific PCR fragment, using the plasmid containing the subcloned PCR fragment K16/K17/K20 as template. Following purification with the GeneClean II kit (Bio 101), the PCR fragment was used as template to generate radiolabeled probe DNA by PCR or with the Random Primed DNA Labeling Kit (Boehringer Mannheim), using [$^{32}$P]dCTP. The unincorporated nucleotides were removed by gel filtration using pre-packed Sephadex G-25 columns (Boehringer-Mannheim). These DNA probes were used in a Southern analysis to show that they hybridized selectively to C. albicans DNA under high stringency conditions.

The Southern blot was generated as follows. EcoRI digested rat (10 μg), yeast S. cerevisiae (2.5 μg), E. coli (1 μg), and C. albicans (2.5 μg) genomic DNAs were loaded onto a 0.8% agarose gel in TAE buffer and the gel was subjected to electrophoresis overnight. The gel was then briefly depurinated in 250 mM HCl, denatured in 0.5M NaOH/1.5M NaCl, and neutralized in 1M Tris-HCl pH 7.4/1.5M NaCl. The DNA was transferred onto a Gene-Screen Plus nylon membrane (Dupont) overnight in 20× SSC (1× SSC is 150 mM NaCl, 15 mM Na-citrate, pH 7.0). Prehybridization and hybridization solutions consisted of 5× SSC, 5× Denhardt's solution, 0.5% SDS, 5 mM EDTA, and 20 μg/ml of salmon sperm DNA. Each filter was incubated overnight at 65° C. with $10^6$ cpm of probe per ml hybridization solution. The filters were then washed three times, for at least 30 minutes, in 2× SSC/0.1% SDS at 65° C. The results of this hybridization experiment were visualized by autoradiography on X-ray film (Kodak X-OMAT).

Figure 4A:
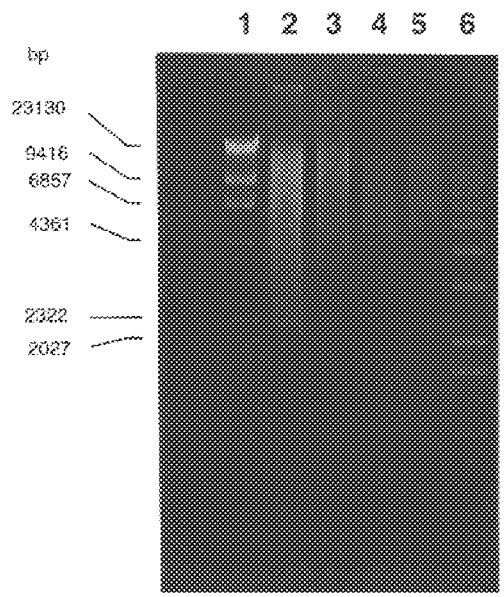
FIGS. 4A and 4B illustrate a Southern hybridization experiment.
Figure 4B:
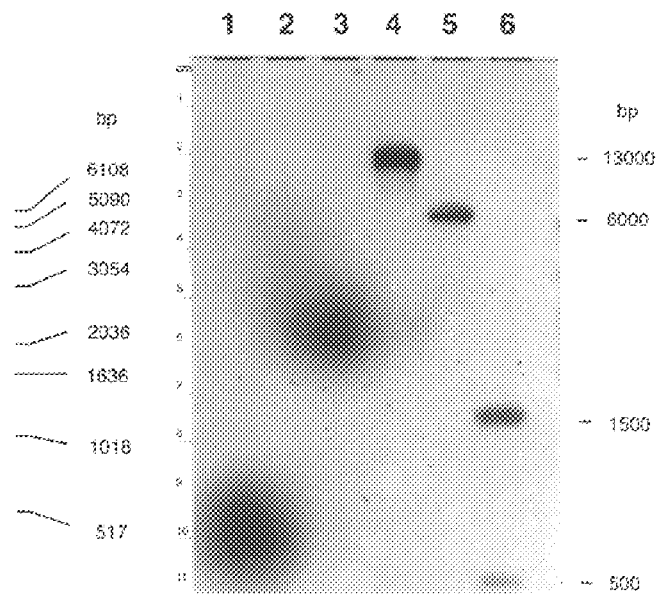

Hybridization under these conditions was observed in the C. albicans DNA lane. A fainter band was also observed in the yeast S. cerevisiae lane (FIGS. 4A and 4B). These Southern hybridization results provided evidence that these PCR fragments were from C. albicans and could be used as probes to screen a genomic library from C. albicans with high stringency to selectively isolate the cytoplasmic tRNA synthetase gene.

TABLE 3

Oligonucleotide Primers Used for PCR Amplification of DNA Fragments for Use as Probes

| Oligonucleotide Sequence | SEQ | PCR Probe |
|---|---|---|
| C-20-2: 5'-<u>GAT</u>TGCGAATTCGAACCAGC-3' | 10 | C-20-1/C-20- |
| C-20-1: 5'-GGAGATGGATTGATATGGAC-3' | 11 | |

Note: C-20-1 corresponds to bases 808–827 in SEQ ID NO:1. C-20-2 (SEQ ID NO:10) is an artificial sequence. The underlined bases are part of the PT7Blue T-Vector cloning site. The rest of the nucleotides were modified from the degenerate primer KIYO-20. Because the degenerate positions R and I present in KIYO-20 are G and G, respectively, in the sequenced PCR clone (in bold in C-20-2 above) and G and A, respectively, in the C. albicans gene, this oligonucleotide cannot be used to produce genomic sequence DNA from genomic template DNA without introducing changes in the primer region.

B. Library screening

Two genomic C. albicans DNA libraries, constructed with DNA from strain WO-1 or with DNA from the highly pathogenic strain C9, were purchased from Dr. P. Magee (University of Minnesota). The Candida albicans strain C9 genomic library consists of DNA fragments of a Sau3A partial digest ligated into the BamHI site of the shuttle vector YPB (Goshorn, A., et al., Infect. Immun. 60:876–884 (1992), Goshorn, A. and Scherer, S., Genetics 123:667–673 (1989), Kwon-Chung, K. J., et al., Infect. Immun. 49:571–575 (1985)). The Candida albicans strain WO-1 pEMBLY23 library consists of HindIII and BamHI partial digest DNA fragments ligated into the BamHI site of the yeast shuttle vector pEMBLY23 (Slutsky, B. M., et al., J. Bacteriol. 169:189 (1987); Baldari, C. and Cesareni, G., Gene 35:27 (1985)). The libraries were plated on 20×20 cm square LB+amp plates such that each plate contained 20,000 to 50,000 colonies (6 to 10 genome equivalents), and the plates were incubated overnight at 37° C. Colonies were transferred to nylon membranes (GeneScreen Plus, Dupont). Each filter was successively transferred to solution I (10% SDS) for 3 minutes, then to solution II (0.5M NaOH/1.5M NaCl) for 5 minutes, and to solution III (1.5M NaCl/0.5M Tris-HCl pH 8.0) for 5 minutes for lysis, denaturation and neutralization, respectively. The filters were then air-dried, and baked in a vacuum oven at 80° C. for 2 to 3 hours. The filters were prehybridized for several hours at 65° C. in hybridization solution (5× Denhardt's solution/5× SSC/ 0.5% SDS/10 mM EDTA and 20 μg/ml salmon sperm DNA) and then hybridized overnight with labeled probe. Probe C20-1/C20-2 was made by using primers C20-1 and C20-2 on pC$^3$305 as template. pC$^3$305 was obtained by cloning the 1.5 kb PCR product (obtained using K-16 and K-20 primers) into pT7Blue T-Vector. The percent identity between the DNA sequences of S. cerevisiae and C. albicans in this 1.5 kb region is 68%, while the overall DNA identity of the ORFs of the IleRS genes of S. cerevisiae and C. albicans using the Clustal method (with the PAM250 residue weight table; DNASTAR, Madison, Wis.) is 60%. The filters were then washed three times with 2× SSC/0.1% SDS at 65° C. and exposed to X-ray film at −80° C. to identify positive clones.

Positive colonies were picked and resuspended into 1 ml of LB+amp medium. To obtain single colonies (200–500 per plate), various dilutions were spread on 150 mm diameter LB+amp plates and incubated overnight at 37° C. Colonies were transferred to Colony/Plaque Screen membranes (Dupont NEN) and retested for hybridization to the probes as described above. Plasmids from single positive clones were isolated and digested with EcoRI (C9 library) or BamHI/HindIII (WO-1 library) restriction enzymes to determine the size of the inserts. The digested clones were also analyzed by Southern hybridization using the same DNA probes as for the library screening. Internal sequencing primers were used to sequence the cloned inserts to confirm that they contained motifs characteristic of IleRS genes. The internal sequencing primers were designed based on sequence information obtained from the original PCR products (Table 2).

C. Results of library screen

Probe C-20-1/C-20-2 (see Example 3A) specific for the cytoplasmic IleRS, was used to screen the C9 *C. albicans* genomic library. Ten out of 30,000 colonies originally hybridized to the radiolabeled probe. Those 10 colonies were purified and tested again for hybridization to the probe. Seven of the 10 colonies hybridized in the secondary screening. EcoRI digestion of the 7 positive clones showed two populations of inserts. Six contained the same 7 kb insert, whereas clone CK-3 contained a 12 kb insert. Clone CK-3 (also named $pC^3410$) contained the full length isoleucyl-tRNA synthetase as determined by partial sequencing with IleRS-specific internal primers and vector-specific primers. Using clone CK-3, the entire gene and its flanking regions were sequenced by the dideoxy chain termination (Sanger) method, using at each round of sequencing, primers designed from sequence information obtained at the previous rounds of sequencing.

Plasmid $pC^3410$ (in *E. coli* DH5α) was deposited in accordance with the provisions of the Budapest Treaty at the American Type Culture Collection (ATCC), 12301 Parklawn Drive, Rockville, MD. 20852, U.S.A. on Oct. 30, 1997, and was assigned Accession Number 98564.

EXAMPLE 4

Nucleotide Sequence and Deduced Amino Acid Sequence of *C. albicans* IleRS Gene Sequencing was done directly on the purified CK-3 plasmid clone using oligonucleotides specific to the internal sequences of the gene to extend toward the 5' and 3' end of the gene within the insert. The sequence within the ORF of the *C. albicans* IleRS was determined for both DNA strands. The individual sequences obtained at each round of sequencing were assembled using the DNA Sequence Management Program of the DNASTAR package to generate contiguous sequences. The methionine initiation codon was identified by comparison with sequences of corresponding IleRS genes present in the GenBank, using the Multiple Sequence Alignment program from the DNASTAR package.

The 3720 nucleotide sequence containing the *C. albicans* cytoplasmic isoleucyl-tRNA synthetase gene (IleRS or CaIleRS) is shown in SEQ ID NO:1. The ORF is 3267 base pairs and encodes a polypeptide of 1088 amino acids (SEQ ID NO:2), with translation starting at the ATG at position 375. The amino acid sequence deduced from the IleRS gene contains two characteristic peptide motifs present in all class I synthetases ($^{61}$HYGH$^{64}$ and $^{609}$KMSKR$^{613}$). The sequences of degenerate primers KIYO-16 and KIYO-17 were found to correspond to nucleotides 639–664 of SEQ ID NO:1; the sequence of degenerate primers KIYO-18 and KIYO-19 were found to correspond to nucleotides 1770–1798 of SEQ ID NO:1.

*Candida albicans* uses a non-universal genetic code; the codon CUG, which normally codes for leucine in most organisms, including *S. cerevisiae*, codes for serine in several species of Candida (Ohama, T., et al., *Nucleic Acids Res.* 17:4039–4046 (1993)). There are two CUG codons in the *Candida albicans* IleRS ORF which correspond to amino acid residues 390 and 1065 in the polypeptide. When the *C. albicans* IleRS gene is expressed in *S. cerevisiae*, or other organisms which use the universal genetic code, the CUG codons are expected to encode leucine at these sites in the expressed recombinant protein (SEQ ID NO:2). When the *C. albicans* IleRS gene is expressed in *Candida albicans* or in other species of Candida which use non-universal decoding, the expected amino acid residues at positions 390 and 1065 are serine (SEQ ID NO:23). Amino acid residues 390 and 1065 are located in non-conserved regions of the protein.

The *C. albicans* IleRS amino acid sequence was compared with the IleRS sequences available in GenBank by using the Multiple Sequence Alignment Program from the DNASTAR (Madison, Wis.) package. Percent similarity and percent divergence among these sequences were determined using the Clustal method with the PAM250 residue weight table. The percent similarity between the predicted amino acid sequence of the *C. albicans* IleRS and the protein identified as IleRS from *S. cerevisiae* was found to be 62%. Other sequences in GenBank were less related.

EXAMPLE 5

Expression of *C. albicans* Isoleucyl-tRNA Synthetase as N-terminal GST-Fusion Protein The DNA fragment comprising the ORF of the *C. albicans* IleRS was amplified by PCR using the following oligonucleotide primers and clone CK-3 as DNA template.

C-5' (SEQ ID NO:12): 5'-CTGCAGCTGAGAAGGAGA<u>GGATCC</u>ATGTCGTTACAAGAAAGCAACAACAATAT-CCC-3'

C-3' (SEQ ID NO:13): 5'-CG<u>GAATTC</u>ACTAAATTTTT-AATAAACGCAAATTAAACAC-3'

The 5' oligonucleotide primer (56 bases) contains, among other restriction sites, a BamHI site (underlined) immediately upstream from the ATG initiation codon (in bold). The last 32 bases are complementary to the 5' coding sequence of the gene. The 3' oligonucleotide primer (39 bases) contains an EcoRI restriction site (underlined) downstream from the stop codon (in bold, TAG in the coding strand). The last 30 bases are complementary to the 3' end of the gene.

PCR amplifications were carried out in 50 μl volumes as described in Example 1, but with 3 units of Vent DNA polymerase (New England Biolabs) and in the presence of 6 mM MgSO$_4$, 200 nM of each primer and 100 ng of CK-3 plasmid template, for 24 cycles of 94° C. (30 seconds), 62° C. (45 seconds), and 72° C. (130 seconds). The 3.3 kb PCR fragment produced by this reaction was purified with the GeneClean II kit, digested with BamHI and EcoRI restriction enzymes, purified again (GeneClean II) and ligated into BamHI/EcoRI digested yeast expression vector pQB83 (a shuttle vector that contains the URA3 and the ampicillin resistance markers; a derivative of pEG(KG) (Mitchell, D. A. et al., *Yeast* 9:715–723 (1993)), yielding plasmid pQB83CAIRS-1. This construct produces an N-terminal GST-fusion protein under the control of the Gal promoter.

The *C. albicans* IleRS expression construct pQB83CAIRS-1 was used to transform *E. coli* DH5α MAX efficiency competent cells (Gibco BRL). *E. coli* transformants containing the correct insert were identified by colony PCR. The plasmids were isolated and introduced into *S. cerevisiae* strain QBY3 (W303; Elion, E. A. et al., *Proc. Natl. Acad. Sci. USA* 88:9392–9396 (1991)); MATa ade2-1 his3-11,15 leu2-3,112 ura3-1 trp1-63 can1-100 Gal$^+$) which was then grown on SC-Ura plates at 30° C. for two days. A single colony was used to inoculate SC-Ura medium containing 2% dextrose, and the culture was incubated at 30° C. overnight. The cells were transferred to SC-Ura medium containing 2% raffinose and incubated at 30° C. At an $OD_{600}$ between 0.5 and 1, the cells were transferred to 30° C. SC-Ura medium containing 2% galactose for induction, and grown overnight at 30° C. Following the growth period, the cells were harvested by centrifugation and lysed at 4° C. by vortexing with glass beads in lysis buffer (25 mM Tris-HCl pH 7.5, 150 mM NaCl, 10 mM EDTA, 1 mM $NaN_3$, 0.1% Triton X-100, 10% glycerol, 1 mM DTT) containing 5 µg/ml each of leupeptin, pepstatin, chymostatin and papain. The cell lysate was centrifuged for 5 minutes at 2500×g and total soluble proteins were recovered in the supernatant (crude extract). The recombinant GST-IleRS protein was purified by affinity chromatography as described in Example 6.

EXAMPLE 6

Purification and Enzymatic Characterization of Fusion Protein

A. Purification

Figure 1B:
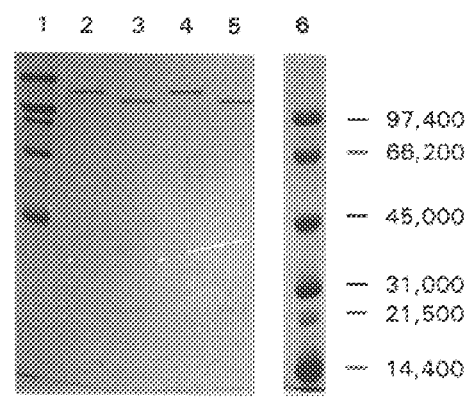

Following cell lysis, whole cell extracts of QBY3/pQB83CAIRS-1 were clarified by centrifugation at 20,000×g for 15 minutes at 4° C. Clarified cell extracts were tested for isoleucyl-tRNA synthetase activity to verify the presence of active protein. Yeast cell extracts containing unmodified pQB83 alone were used as a negative control. GST-fusion proteins were purified by affinity chromatography on Glutathione Sepharose 4B resin (Pharmacia) equilibrated with PBS. Cell extracts were filtered through a 0.45 µm filter (Nalgene) and either mixed with the resin in batch or loaded onto a column containing the resin. Unbound proteins were washed off the resin with ice cold PBS (10 bed volumes) and bound proteins were eluted off the resin in 3 bed volumes of PBS containing 10 mM glutathione, then concentrated by ultrafiltration using centrifuge concentrators (Centiprep 30 or Centricon 30, from Amicon), and stored at pH 7.5 at −20° C. in 40% glycerol in the presence of 5 to 20 mM DTT. The GST moiety was removed by incubation of the purified proteins with 0.5 unit thrombin at 16° C. for 16 hours. Proteins were visualized on a 10% SDS-polyacrylamide gel following staining with Coomassie blue (FIGS. 1A and 1B). The purity of the GST-IleRS was estimated to be at least about 85%.

B. Enzymatic activity

The purified recombinant GST-fusion protein and the product after thrombin cleavage of the GST-fusion protein were tested for their charging activities. Charging assays were based on the procedure of Shepard et al. (*Proc. Natl. Acad. Sci. USA* 89:9964–68 (1992)). Unless otherwise stated, a typical 50 µl reaction was carried out at 25° C. and contained 4 mM ATP, 20 µM of [$^3$H]isoleucine, 90 µM crude tRNA from *E. coli* (Sigma) or brewer's yeast (Boehringer Mannheim), 10 µM KF, 50 mM HEPES, pH 7.5, 10 mM $MgCl_2$, 10 mM DTT or β-mercaptoethanol and 30 mM $NH_4Cl$. Purified enzyme was diluted in 100 mM HEPES, pH 7.5, 20 mM DTT and 0.1 mg/ml BSA.

Figure 2:
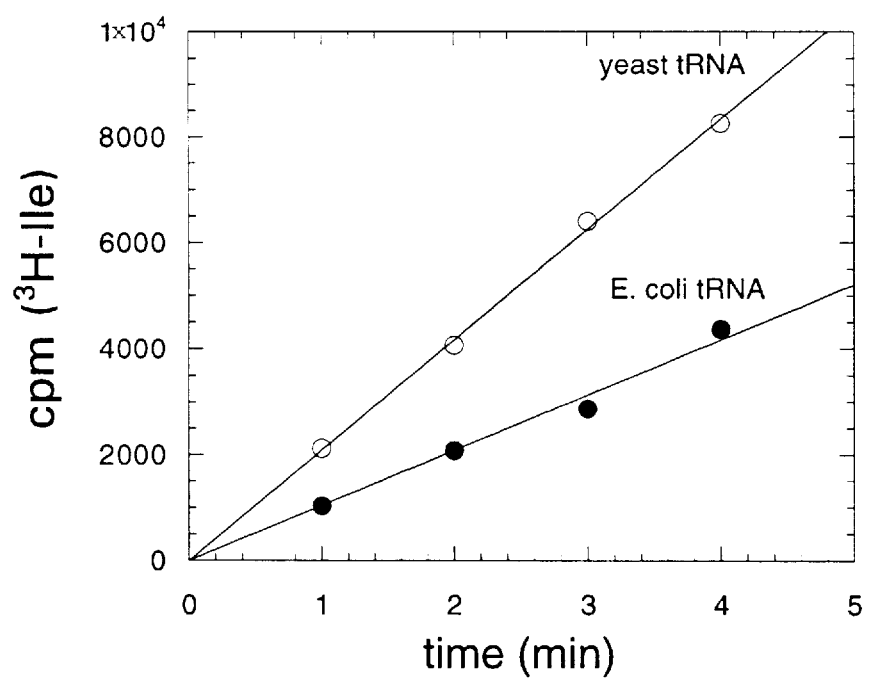
FIG. 2 is a graph illustrating the aminoacylation activity (cpm, counts per minute of [$^3$H]isoleucyl-tRNA) over time (minutes) of (uncleaved) purified N-terminal GST-IleRS (produced in *S. cerevisiae*) using crude total tRNA from *E. coli* (●) or brewer's yeast (○). See Example 6B.

Reactions were started by the addition of enzyme to the reaction mixture preincubated at 25° C. At various time intervals, 10 µl of the reaction mix was spotted on 3MM Whatman filter circles which were then immersed in ice cold 5% TCA. After three washes in ice cold 5% TCA (at least 15 minutes each), the filters were rinsed once with cold ethanol, once with ether, and air dried. The radioactivity was quantitated by counting the filters in a table top scintillation counter (Packard) in the presence of scintillation fluid (Betafluor; National Diagnostics). See FIG. 2.

For determination of $K_m$, various concentrations of one substrate (ATP, amino acid, or tRNA) were used while the other two substrates were kept at saturating concentrations. To test the effect of temperature, the reactions were incubated at 25°, 30°, 37° and 42° C. The Bradford assay was used for determination of total protein. The proportion of active enzyme was calculated by monitoring the formation of the amino acid-adenylate:enzyme complex using a nitrocellulose filter binding assay in the presence of various dilutions of enzyme preparation. A 50 µl reaction contained 1 mM ATP, 1 unit of pyrophosphatase, 50 mM Tris-HCl, pH 5.8, 10 mM $MgCl_2$, 30 mM KCl, 20 mM DTT, 40 µM of radioactively labeled amino acid, and diluted enzyme.

Purified *C. albicans* GST-isoleucyl-tRNA synthetase (GST-IleRS) had an approximate molecular weight of 150 kD. Thrombin-treated enzyme had an apparent molecular weight of 124 kD. The purified enzyme (with or without the GST moiety) was able to efficiently aminoacylate both *E. coli* and yeast total tRNAs (purchased from Sigma and Boehringer Mannheim, respectively). The $K_m$ for isoleucine was determined using crude yeast tRNA (Boehringer Mannheim) and 2 to 32 µM of [$^3$H]isoleucine (specific activity=2200 cpm/pmol). The $K_m$ value was 17 µM±4.8 µM. The amount of active enzyme was approximately 70% of total enzyme or 1.09 nM for $K_m$ determination. At this concentration, $V_{max}$ was 4±0.5 nM/s and $k_{cat}$ was 3.7±0.5 per sec. The optimum temperature for enzymatic activity was found to be 37° C. The kinetic parameters were similar for the *C. albicans* GST-IleRS fusion protein and the GST-IleRS cleaved protein, suggesting that the GST moiety does not affect the folding and activity of the IleRS enzyme.

EXAMPLE 7

Genetic Complementation of *S. cerevisiae* tRNA Synthetase Null Mutants

The ability of the isolated *C. albicans* isoleucyl-tRNA synthetase gene to complement a *Saccharomyces cerevisiae* ils1 null strain was tested. For complementation assays in *S. cerevisiae*, a yeast haploid ils1 null strain (QBY187) was constructed (see below for details). The haploid null strain contains a chromosomal deletion of the gene encoding isoleucyl-tRNA synthetase, and a maintenance plasmid (pQB89) bearing a URA3 selectable marker, which provides wild type IleRS activity in trans. The *Candida albicans* isoleucyl-tRNA synthetase gene was cloned in a yeast expression vector (pQB169) that contains a LEU2 selectable marker, to yield plasmid pQB169+IleRS (also named $pC^3408$ and $pC^3409$). For complementation assays, the yeast haploid null strain was transformed with $pC^3408$ and transformants were selected on minimal plates lacking leucine and uracil. Cells were selected for loss of the URA3 maintenance plasmid pBQ89, containing the wild type yeast IleRS gene (ILS1), by plating the transformants on media containing 5-FOA. Survival of cells on 5-FOA-containing media demonstrates that the *Candida albicans* IleRS gene can substitute for the *S. cerevisiae* enzyme in vivo, as the *Candida albicans* gene becomes the sole source of isoleucyl-tRNA synthetase enzymatic activity after the loss of the maintenance plasmid.

Constructing a *Saccharomyces cerevisiae* ils1 null strain

To construct a chromosomal deletion of ILS1 by gamma-transformation (Sikorski, R. S. and Hieter, P., *Genetics* 122:19–27 (1989)), a TRP1 integrating plasmid, pRS304 (Sikorski, R. S. and Hieter, P., *Genetics* 122:19–27 (1989)), containing 5' and 3' flanking sequences of ILS1 was made.

ILS1, the gene encoding the cytoplasmic isoleucyl-tRNA synthetase of *S. cerevisiae*, has been cloned and sequenced previously (Englisch, U., et al., *Biol. Chem. Hoppe-Seyler* 368:971–979 (1987); Martindale, D. W., et al., *Curr. Genetics* 15:99–106 (1989)). ATCC lambda clone PM4967 (ATCC Accession Number 70323; American Type Culture Collection, Rockville, Md.), containing about 20 kb of the *S. cerevisiae* genome from chromosome II that includes the ILS1 gene, was used to infect *E. coli* strain C600. Phage DNA was isolated and digested with either EcoRI restriction enzyme, releasing a 6 kb fragment, or with BamHI restriction enzyme, releasing a 5.2 kb fragment containing the ILS1 gene and flanking DNA. Both fragments contained the ILS1 gene and flanking DNA. The EcoRI fragment was subcloned into the EcoRI restriction site of phagemid pBSKS(+) (Stratgene), yielding pQB76, and the BamHI fragment was subcloned into the low copy number YCplac33 or YEplac181 plasmids (YCplac33 is a URA3, CEN4 plasmid; Gietz, R. D. and Sugino, A., *Gene* 74:527–534 (1988)), yielding the ILS1 maintenance plasmid pQB89 and positive control plasmid pQB93, respectively.

To construct a chromosomal deletion of ILS1 by gamma-transformation (Sikorski, R. S., and Hieter, P. *Genetics* 122:19–27 (1989)), a TRP1 integrating plasmid, pRS304 (Sikorski, R. S., and Hieter, P. *Genetics* 122:19–27 (1989)), containing 5' and 3' flanking sequences of ILS1, was made. The 1 kb EcoRI-BamHI fragment (5' flank) and the 800 bp HpaI-EcoRI fragment (3' flank) of plasmid pQB76 were ligated to BamHI/SmaI digested pRS304 to produce plasmid pQB118. Digestion of pQB118 with EcoRI yields a linear piece of DNA with the TRP1 marker (and plasmid DNA) between the flanking sequences of ILS1. Strain FY83 (MATa/α lys2-128δ/lys2-128δ leu2Δ1/leu2Δ1 ura3-52/ura3-52 trp1Δ63/trp1Δ63), obtained from Fred Winston (Harvard Medical School), was transformed with 5 μg of EcoRI-digested pQB118 and plated on SC-Trp plates to construct a heterozygous (i.e., ILS1⁺/ils1Δ::TRP1) strain by one-step gene disruption (Rothstein, J., *Methods in Enzymology* 101:202–211 (1983)). Independent Trp⁺ transformants were purified, their genomic DNA isolated, digested with XbaI, and screened by Southern analysis for disruption of the ILS1 gene, using the 800 bp EcoRI-HpaI ("3'-flank") DNA fragment as a probe. A transformant (QBY182) containing both a 2.5 kb (ILS1) and a 4.2 kb (ils1Δ::TRP1) band was sporulated, and upon tetrad analysis revealed 2:2 segregation for viability on minimal media lacking leucine. All viable spores were Trp-, indicating that TRP1 is linked to inviability, as expected for spores inheriting the chromosome with the ils1Δ::TRP1 disruption.

To construct the haploid null strain QBY187, strain QBY182 was transformed to Ura⁺ with the ILS1 maintenance plasmid pQB89. This transformant was sporulated, and following tetrad analysis, two haploid Trp⁺ Ura⁺ spores of opposite mating type were identified and designated QBY187 (MATα leu2Δ1 lys2-128δ ura3-52 trp1Δ63 ils1Δ::TRP1 /pQB89) and QBY188 (MATa leu2Δ1 lys2-128δ ura3-52 trp1Δ63 ils1Δ::TRP1/pQB89).

Construction of yeast expression vectors pQB169 and pQB172

Plasmid pMC4 carries the ADH promoter of *S. cerevisiae*, and downstream of the promoter, the coding sequence for the cytochrome oxidase IV mitochondrial targeting peptide (Pinkham, J., et al., *Mol. Cell. Biol.* 14:4643–4652, (1994); Hurt, E. C., et al., *J. Biol. Chem.* 262:1420–1424 (1987); Hurt, E. C., et al., *EMBO J.* 3:3149–3156 (1984)). Derivatives of plasmid pMC4 can be constructed which lack a functional mitochondrial targeting sequence, allowing cytoplasmic expression. Alternatively, the ADH promoter of pMC4 can be excised and inserted into another suitable vector. Plasmids pQB169 and pQB172, which were constructed for the expression of heterologous genes in yeast cytoplasm, are examples of vectors constructed in this manner.

pQB169 pQB169 contains the constitutive ADH promoter, a polylinker and the ILS1 transcriptional terminator. A 450 bp fragment containing the constitutive ADH promoter (pADH) with its transcriptional start sites (but not a translational start site, i.e., ATG) was amplified by PCR using plasmid pMC4 as template. Primers were designed to incorporate a HindIII restriction site at the 5' end (HindIII site in bold below in primer JK-1, SEQ ID NO:14) of the fragment and a PstI restriction site at the 3' end (PstI site in bold below in primer JK-2, SEQ ID NO:15):

JK-1 (SEQ ID NO:14):
5'-CCAAGAAGCTTGAAGTAATAATAGGCGCATGC-3'

JK-2 (SEQ ID NO:15):
5'-CGTACTGCAGGATTGTATGCTTGGTATAGC-3'

The resulting PCR product was cleaved with HindIII and PstI restriction enzymes, and the HindIII-PstI fragment containing pADH was subcloned into the HindIII and PstI restriction sites of vector YEplac181 (Gietz, R. D. and Sugino, A., *Gene* 74: 527–534 (1988)), a 2μ LEU2 yeast shuttle vector, to yield intermediate plasmid pQB147.

For efficient transcription termination, a 270 bp terminator fragment (tILS1), containing conserved transcription termination signals (Zaret, K. S., and F. Sherman, *Cell* 28: 563–573 (1982)) was generated by PCR, using plasmid pQB89 as template.

The 270 bp tILS1 PCR fragment was engineered to have an EcoRI restriction site at the 5' end (EcoRI site in bold below in JK-5, SEQ ID NO:16), and a NarI restriction site at the 3' end (NarI site in bold below in JK-6, SEQ ID NO:17), and contains the 3' untranslated region of ILS1, including bases 3519–3846 of the ILS1 gene (Englisch, U. et al., *Hoppe-Seyler* 368:971–979 (1987)). The primers used to prepare this fragment were as follows:

JK-5 (SEQ ID NO:16): 5'-GGA ATT CTG AAA ACA ACT CAT ATA AAT ACG-3'

JK-6 (SEQ ID NO:17): 5'-GAG GCG CCC TCT TAT CAA TCC CCT CCT CAA CC-3'

The resulting PCR product was cleaved with EcoRI and NarI restriction enzymes. pQB147 was cleaved with EcoRI and NarI, and the EcoRI-NarI tILS1 fragment was subcloned into the EcoRI and NarI restriction sites of the vector to yield expression vector pQB169. Transformants of *E. coli* DH5α containing pQB169 were obtained. Transcription of a gene inserted into this vector can be initiated from pADH, and translation can be initiated at the first ATG of the insert.

To make a single-copy (CEN) version of this vector, the expression cassette (pADH-polylinker-tILS1) of pQB169 was excised with HindIII and NarI, and was subcloned into the HindIII and NarI restriction sites of HindIII-NarI digested YCplac111 (Gietz and Sugino, *Gene* 74:527–534 (1988)) to yield pQB172. Transformants of *E. coli* DH5α containing pQB172 were obtained.

Construction of pC³408 and complementation results

The construction of the plasmid expressing the *Candida albicans* isoleucyl-tRNA synthetase for complementation in yeast was as follows. The EcoRI/BamHI digested and purified 3.3 kb PCR fragment containing the entire *C. albicans* IleRS gene (see Example 5) was ligated into the shuttle vector pQB169 (LEU2, bla) at the EcoRI and BamHI sites to yield pQB169+IleRS (also named pC$^3$408 and pC$^3$409). This construct put the *C. albicans* IleRS gene under the control of the yeast ADH promoter. The ligation mixture was used to transform strain QBY187 (MATα leu2Δ1 lys2-128δ ura3-52 trp1Δ63 ils1Δ::TRP1/pQB89); selection for transformants was on SC-Leu.

Figure 3:
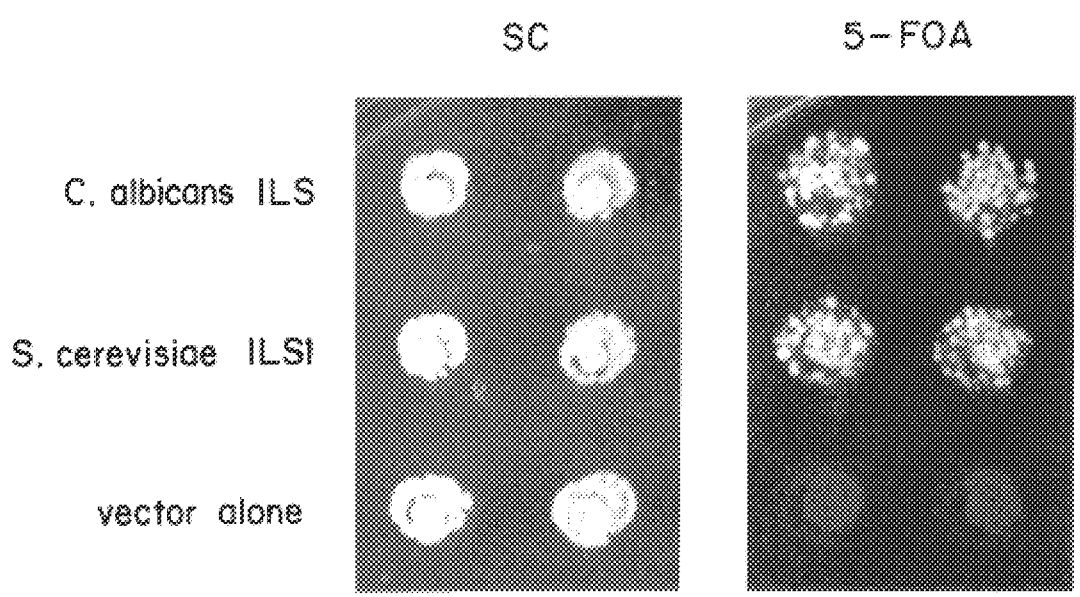
FIG. 3 consists of photographs which show the results of complementation of *S. cerevisiae* strain QBY187 by plasmid pQB169+IleRS (expressing the *Candida albicans* IleRS gene; also called pC$^3$408 or pC$^3$409), by plasmid pQB93 (expressing wild type *S. cerevisiae* IleRS gene) or by pQB169 (vector alone). Cell suspensions (in water) were made from individual colonies of QBY187/pC$^3$408, QBY187/pQB93 and QBY187/pQB169. Cells from the suspensions were spotted sequentially onto SC-Leu agar plates (SC) and SC+5-FOA agar plates (5-FOA). The photograph shows the growth, after 48 hours at 37° C., of a cluster of colonies arising from these spotted cells.

The *C. albicans* IleRS gene was found to rescue the null mutant QBY187 as demonstrated by the ability of the yeast cells containing plasmid pC$^3$408 to grow on SC+5-FOA agar, where 5-FOA selects for the loss of pQB89, the ILS1 maintenance plasmid (FIG. 3). This provided evidence that the *Candida albicans* IleRS gene was expressed from the yeast promoter and produced active protein capable of functioning in vivo.

The loss of pQB89 from the survivors on SC+5-FOA agar was verified. Plasmid DNA was isolated from several colonies of QBY187/pC$^3$408 on 5-FOA plates and the DNA was shown by restriction digest to correspond to the *Candida albicans* IleRS clones. In addition, colonies growing on 5-FOA were tested for growth on several media, in particular SC-Ura media, to verify that the maintenance plasmid was lost. No growth on SC-Ura indicated loss of pQB89.

EXAMPLE 8

Aminoacylation Activity of IleRS Isolated from *C. albicans*

For *C. albicans* isoleucyl-tRNA synthetase, the kinetic values of the naturally occurring and recombinant enzymes have been determined, and they compare very well. Isoleucyl-tRNA synthetase activities have been tested directly in crude extracts obtained by mechanical cell breakage using glass beads (described by S. M. Jazwinski "Preparation of Extracts from Yeast" in "Guide to Protein Purification," by M. P. Deutscher (editor) *Methods in Enzymology* volume 182, Academic Press, Inc. (1990)). The cell breakage was followed by preparation of a 100S supernatant (by an initial low speed spin at 17,000 rpm for 30 min), to remove cell debris and glass beads, followed by a high speed spin at 36,500 rpm for 1 hour (100,000 g) by ultracentrifugation in a 70Ti rotor. However, the IleRS activity was more stable if the 100S supernatant is purified by a DEAE column. Elution was done with 500 mM NaCl or potassium phosphate, using a gradient or a stepwise elution. Fractions containing IleRS activity were pooled and concentrated, and stored at –20° C. in 40% glycerol. The activity has remained stable over an 8 month period.

Preparation of 100S supernatant

A single colony of the *Candida albicans* strain ATCC Accession No. 90028 was grown in YEPD to saturation (30° C., 2 days). 5 μl of this saturated culture was used as inoculum for one liter of YPD broth in a 2 liter flask. Incubation was carried out at 30° C. overnight in a shaking incubator (225 rpm). Log-phase cells (OD$_{600}$=8–10) were harvested by low-speed centrifugation (3,000 rpm for 5 min). The cell pellet was washed (with distilled H$_2$O or 100 mM Tris, pH 7.4) and resuspended as a 40% cell paste in chilled buffer A (20 mM KPO$_4$, pH 7.4 or 20 mM NaCl, pH 8.0, 10% glycerol, 5 mM DTT and 1–2 "Complete" tablets (a cocktail of protease inhibitors from Boehringer-Mannheim)).

Cells were broken after addition of an equal volume of glass beads (0.45 micron in diameter; Biospecs) in a Bead-Beater (Biospecs) with 1 min pulses and 1 min cooling periods at 4° C. Total breakage time varied depending on the efficiency of lysis. The 100S supernatant was collected after two centrifugation steps; the conductivity and pH of the supernatant were adjusted before application onto the DEAE column (DEAE Sepharose Fast Flow (Pharmacia LKB Biotechnology)).

Aminoacylation assays

Figure 5:
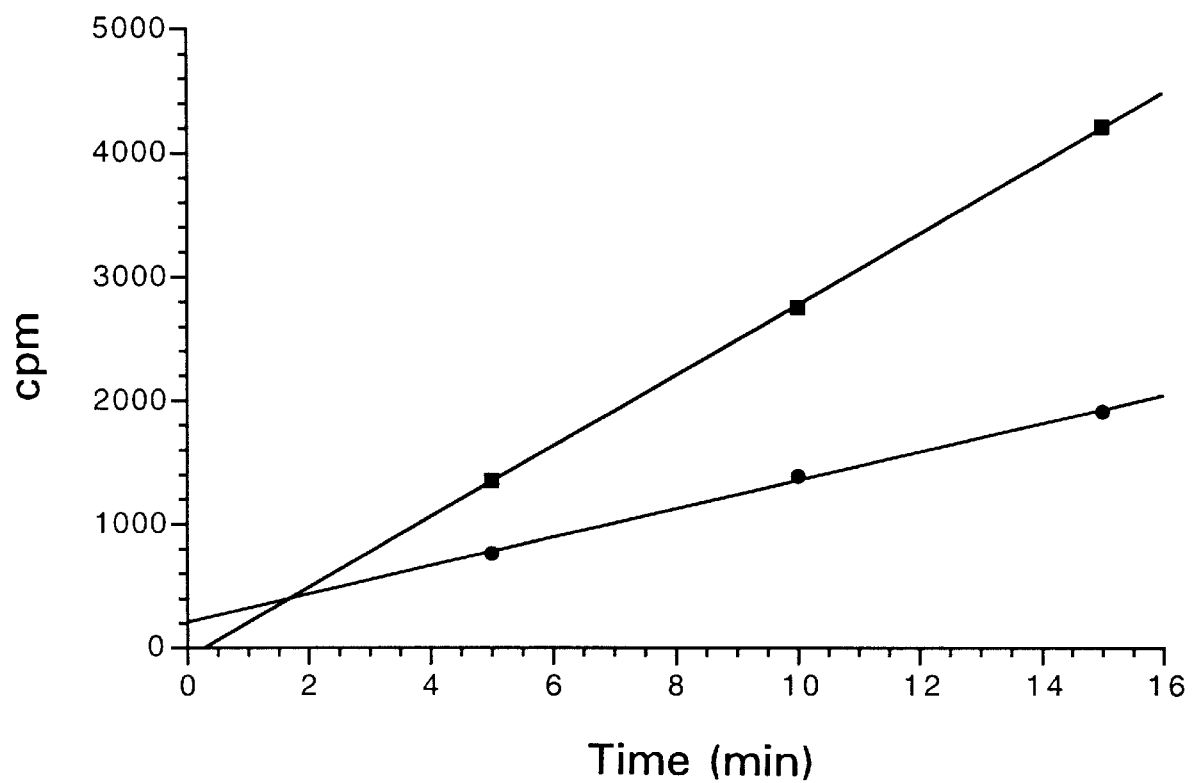
FIG. 5 is a graph showing aminoacylation activity (cpm, counts per minute of [³H]isoleucyl-tRNA) over time (minutes) of C. albicans isoleucyl-tRNA synthetase partially purified as in Example 8, using crude total tRNA from brewer's yeast as substrate. Lot Ca 5,6,7 was made from 8 liters of culture. The activities of 1:50 (■) and 1:100 (●) final dilutions of enzyme are shown.

Aminoacylation reactions were carried out at 25° C. in 30 mM HEPES pH 7.5, 30 mM KCl, 5 mM MgCl$_2$, 10 mM DTT, 20 μM [$^3$H]amino acid, 90 μM brewer's yeast tRNA (Boehringer-Mannheim Biochemicals, Inc.), 2 mM ATP, 10 mM KF, and a suitable dilution of the partially purified enzyme from *C. albicans*. 15 μl of each reaction were quenched in a 96-well filter plate (Millipore, cat# MAFBNOB50) prefilled with 100 μl of cold 5% TCA. The liquid in the filter plate was drained by applying vacuum suction on the manifold. The plate was subsequently washed 2 times with 200 μl 5% TCA, 2 times with 100 μl double distilled H$_2$O with continuous vacuum suction, and once with 100 μl EtOH. The plate was heat-dried under vacuum, 100 μl Microscint was added to each well, and the aminoacylated tRNA was quantitated by scintillation counting in a Topcount (Packard) scintillation counter. A typical result of a time course aminoacylation assay is shown in FIG. 5.

EXAMPLE 9

Assay for Inhibitors of Enzymatic Activity

To detect inhibitors of enzymatic activity, the extent of aminoacylation of tRNA with isoleucine was assessed using the GST-fusion IleRS encoded by pQB83CAIRS-1 and purified as in Example 6A and diluted 1:245. Aminoacylation activity was measured by monitoring the incorporation of [$^3$H]isoleucine into tRNA. Aminoacylation reactions in the absence of test compounds were measured as control activity, reactions with known inhibitors were employed to assess the sensitivity of the system, and reactions containing test compounds were used to identify novel inhibitors.

Isoleucyl-tRNA synthetase enzyme was first pre-incubated at 25° C. with 50 mM HEPES (pH 7.5), 0.05 mg/ml bovine serum albumin, 10 mM dithiothreitol, and 2.5% dimethyl sulfoxide (DMSO) with or without a test compound in a volume of 20 microliters in the wells of a microtiter plate (Falcon tissue culture plate, #3077). After 30 minutes, the pre-incubation mixture was supplemented to give a final concentration in the assay of 10 mM magnesium chloride, 50 mM potassium chloride, 0.08 mM ATP, 20 μM [$^3$H]isoleucine (4.7 Ci/mmol), 90 μM crude brewer's yeast tRNA and 1.4% DMSO, to a final volume of 35 microliters, and incubated at 25° C. A 15 microliter aliquot was removed at 10 minutes and added to an individual well of a Millipore filtration plate (MultiScreen-FB, MAFB NOB 10) containing 100 microliters of cold 5% (wt/vol) trichloroacetic acid. Trichloroacetic acid-precipitable [$^3$H]isoleucyl-tRNA was collected by filtration on a Millipore MultiScreen filtration station. Filtration plates were washed two times with 5% trichloroacetic acid, twice with water, and dried overnight. Radioactivity was quantitated with Packard Microscint-20 in a Packard TopCount microplate scintillation counter. Inhibitor activity was reported as a percentage of the control aminoacylation activity, as shown in Table 5 below.

TABLE 5

| Compound ID | Concentration in assay (µM) | cpm | % activity |
|---|---|---|---|
| none | 0 | 1767 | 100 |
| CB-168 | 20 | 338 | 19 |
| CB-168 | 2 | 1233 | 70 |
| CB-168 | 0.2 | 1636 | 93 |
| CB-56521 | 20 | 112 | 6.3 |
| CB-56521 | 2 | 119 | 6.7 |
| CB-56521 | .2 | 248 | 14 |
| CB-56521 | .02 | 702 | 40 |
| CB-56521 | .002 | 1434 | 81 |
| CB-56521 | .0002 | 1541 | 87 |

EXAMPLE 10

PCR-directed Mutagenesis to Change CTG Codons in C. albicans IleRS Gene to TCT While CTG codons are decoded as serine in some Candida species, including *C. albicans*, in *S. cerevisiae* they are read as leucine. The $K_m$ of the recombinant GST-fusion protein as measured for isoleucine (17 µM) is comparable to the $K_m$ determined for the naturally-occurring protein in a partially purified extract (5 µM), so it is unlikely the CTG-encoded leucine residues that are located in non-conserved portions of the *Candida albicans* IleRS affect the activity of the recombinant protein as it is produced in *S. cerevisiae*. However, in order to produce a recombinant protein that is identical in amino acid composition to the protein produced in *Candida albicans*, PCR mutagenesis was used to change the two CTG codons to TCT, one of the most highly used serine codons in *S. cerevisiae*.

Figure 6:
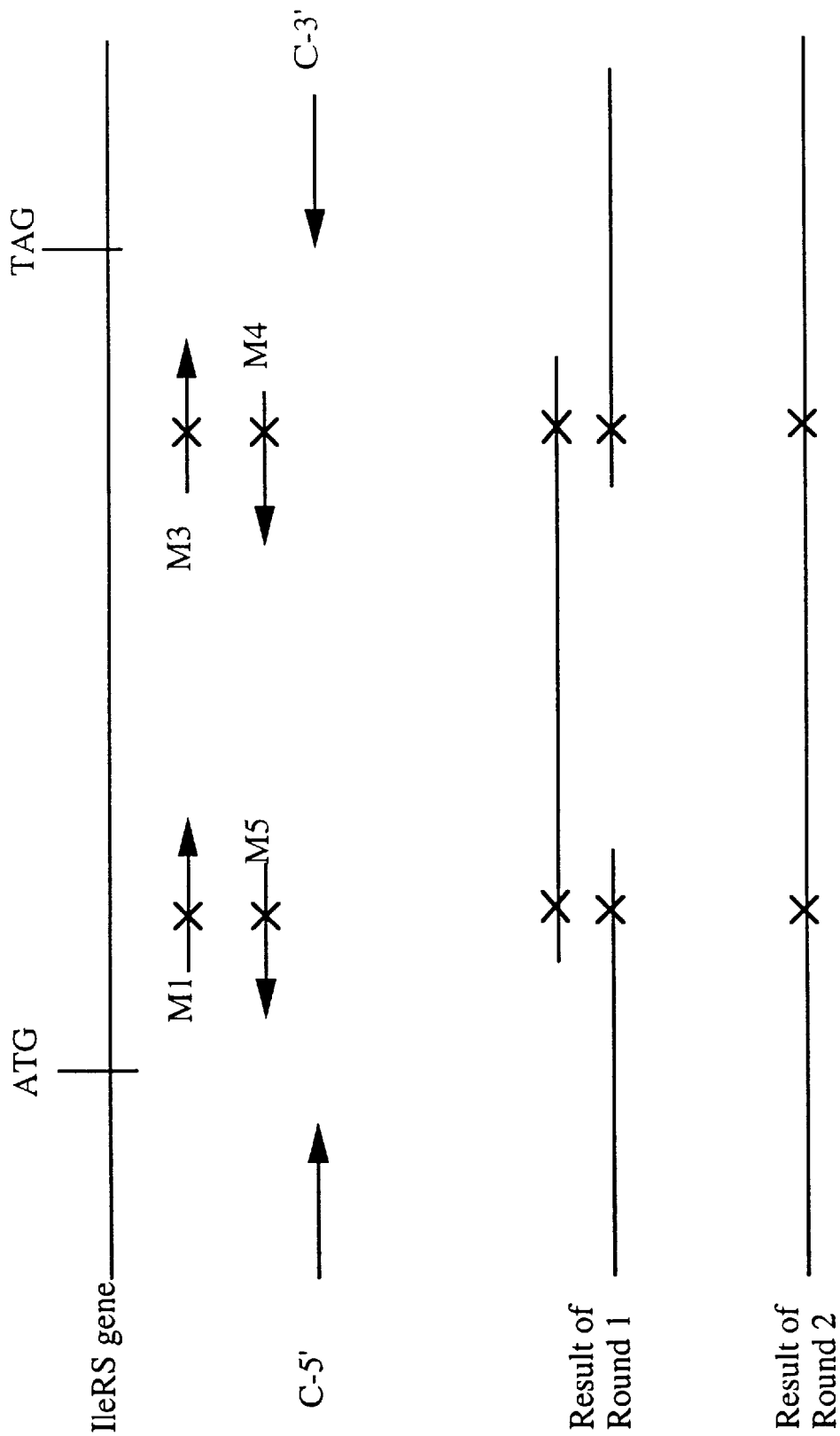
FIG. 6 is a diagram illustrating the scheme used to change the two CTG codons in the C. albicans IleRS Gene to TCT by PCR-directed mutagenesis. See Example 10.

PCR mutagenesis was used to prepare a DNA encoding the full length ORF with the incorporated changes to the *Candida albicans* IleRS gene (FIG. 6). Vent DNA polymerase (using a standard PCR reaction cocktail on 0.2 µg of pC³410 as template) was employed to generate three overlapping PCR fragments in a first round of mutagenesis: C-5' (5' primer for cloning in pQB83 yeast expression vector) with CaIleRS-M-5#, CaIleRS-M-1# with CaIleRS-M-4#, and CaIleRS-M-3# with C-3' (3' primer for cloning in pQB83 yeast expression vector).

CaIleRS-M-1# (SEQ ID NO:18; corresponds to nucleotides 1524–1565 of coding strand of SEQ ID NO:22)
5'-GTTATTATCAAGAAATTAtctGAAGAAGGTAGAC-TCTTGGTC-3'

CaIleRS-M-3# (SEQ ID NO:19; corresponds to nucleotides 3551–3589 of coding strand of SEQ ID NO:22)
5'-GAAGGAAGCACAAGATtctGCTAATGTCATTACC-GATG-3'

CaIleRS-M-4# (SEQ ID NO:20; corresponds to nucleotides 3545–3583 of non-coding strand of SEQ ID NO:22)
5'-GTAATGACATTAGCagaATCTTGTGCTTCCTTCAA-TTCC-3'

CaIleRS-M-5# (SEQ ID NO:21; corresponds to nucleotides 1520–1559 of non-coding strand of SEQ ID NO:22)
5'-GAGTCTACCTTCTTCagaTAATTTCTTGATAATAA-CCTTG-3'

The mixture was heated to 94° C. for 2 min followed by 30 cycles of denaturation (94° C., 30 sec), annealing (50° C., 30 sec) and extension (72° C., 2.5 min) and an extra 4 min incubation at 72° C. at the end of the 30 cycles. PCR fragments from this round of PCR were gel purified and used as template for a second PCR reaction, this time employing only C-5' and C-3' primers, but otherwise with PCR conditions identical to the previous round. Approximately 100 bases in the region of the mutagenized codons were sequenced to verify that the PCR mutagenesis procedure was successful. These regions correspond to nucleotides 1445 to 1558 and 3473 to 3600 in SEQ ID NO:22. This DNA fragment is to be cloned in a *Saccharomyces cerevisiae* expression system, sequenced in its entirety to verify that no other changes were introduced inadvertently during the mutagenesis steps and expressed.

Equivalents

Those skilled in the art will be able to recognize, or be able to ascertain, using no more than routine experimentation, many equivalents to the specific embodiments of the invention described herein. Such equivalents are intended to be encompassed by the following claims.

---

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 3720 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( i x ) FEATURE:
        ( A ) NAME/KEY: CDS
        ( B ) LOCATION: 375..3638

( x i ) SEQUENCE DESCRIPTION: SEQ ID NO:1:

-continued

```
TTTTGGATAC TATCAAACAA GAGGAATGAC TAATACAGAA TTAGTGTTAC GAATCAATGG    60

CACTACAGCA ACTTTCAACA AAATAATCTA CGTTCAAAAT ATAATATATA CTATTAAATA   120

AAATCAAATA ATAAAATAAT TTTAAAGAAA GTAGTACCAG CTCTTTTTTT TGTTTCCGTT   180

TATACCATCC AAATCAATTC CTATTAGTCG GGATCATTGA TTGAGTGAGT GAGTGAGTGA   240

TGACTGAGCA GCAGGTCGTG CGATCTCACG ATATGTGTCA CAACGAAACC TGAAAAAAAA   300

AAAGACTCAA AAATTTTTTT CTTCTCTTCC GTCTATTACT CATCTATACA TCAACAAGTT   360

GGTACTTTAC AGAT ATG TCG TTA CAA GAA AGC AAC AAC AAT ATC CCT CAA    410
            Met Ser Leu Gln Glu Ser Asn Asn Asn Ile Pro Gln
             1               5                  10

GGT GCT TTT AGT TTT CCT AAG GAA GAA GAA GCA GTT ATC AAA CAT TGG    458
Gly Ala Phe Ser Phe Pro Lys Glu Glu Glu Ala Val Ile Lys His Trp
         15                  20                  25

GAT GAT GTC AAT GCT TTT CAA AGA ACT TTA GAG TTG ACT GAA GAT TTA    506
Asp Asp Val Asn Ala Phe Gln Arg Thr Leu Glu Leu Thr Glu Asp Leu
     30                  35                  40

CCG CCA TTT GCG TTT TTT GAC GGA CCA CCA TTT GCC ACT GGT ACT CCT    554
Pro Pro Phe Ala Phe Phe Asp Gly Pro Pro Phe Ala Thr Gly Thr Pro
 45                  50                  55                  60

CAT TAC GGG CAC ATT TTG GCC TCT ACA GTC AAA GAT ATT ATC CCA CGT    602
His Tyr Gly His Ile Leu Ala Ser Thr Val Lys Asp Ile Ile Pro Arg
                 65                  70                  75

TAT GCC ACC ATG AAC GGG TAT CAT GTG GAG AGA AGA TTC GGT TGG GAT    650
Tyr Ala Thr Met Asn Gly Tyr His Val Glu Arg Arg Phe Gly Trp Asp
             80                  85                  90

ACC CAC GGT TTG CCA GTA GAA CAT GAA ATT GAC AAA AAG TTG AAC ATT    698
Thr His Gly Leu Pro Val Glu His Glu Ile Asp Lys Lys Leu Asn Ile
         95                 100                 105

ACC TCG AAA GAA GAT GTT TAT GCC ATG GGT ATT GAC AAG TAC AAT GCT    746
Thr Ser Lys Glu Asp Val Tyr Ala Met Gly Ile Asp Lys Tyr Asn Ala
 110                 115                 120

GAA TGT CGT GCA ATT GTG ATG AGA TAC GCT GAT GAA TGG CGT AGA ACA    794
Glu Cys Arg Ala Ile Val Met Arg Tyr Ala Asp Glu Trp Arg Arg Thr
 125                 130                 135                 140

ATC AAG AGA TTG GGG AGA TGG ATT GAT ATG GAC AAC GAT TAC AAA ACC    842
Ile Lys Arg Leu Gly Arg Trp Ile Asp Met Asp Asn Asp Tyr Lys Thr
             145                 150                 155

TTG TAC CCT GAA TTT ATG GAA TCT GTG TGG TGG GCT TTC AAG GAG TTG    890
Leu Tyr Pro Glu Phe Met Glu Ser Val Trp Trp Ala Phe Lys Glu Leu
         160                 165                 170

TTT AAC AAG GAT GCC GTT TAT AGA GGT TTG AGG GTC ATG CCT TAT TCC    938
Phe Asn Lys Asp Ala Val Tyr Arg Gly Leu Arg Val Met Pro Tyr Ser
 175                 180                 185

ACT GCT TGT ACC ACA CCA TTG TCG AAC TTT GAA GCC CAA CAA AAC TAT    986
Thr Ala Cys Thr Thr Pro Leu Ser Asn Phe Glu Ala Gln Gln Asn Tyr
 190                 195                 200

AAA GAA GTT AAC GAC CCA GCA CTT ACT ATT TCG TTC CCA TTG CTT GAT   1034
Lys Glu Val Asn Asp Pro Ala Leu Thr Ile Ser Phe Pro Leu Leu Asp
 205                 210                 215                 220

AAC GAA GAC ACT TGT TTG GTT GCT TGG ACT ACC ACG CCA TGG ACC TTA   1082
Asn Glu Asp Thr Cys Leu Val Ala Trp Thr Thr Thr Pro Trp Thr Leu
             225                 230                 235

CCT GCA AAT CTT GCG TTA GCA GTT AAT CCA AAG TTT GAG TAT GTA AAG   1130
Pro Ala Asn Leu Ala Leu Ala Val Asn Pro Lys Phe Glu Tyr Val Lys
         240                 245                 250

ATT TTT GAT GAG GAA AAA AAG AAA AAC TTT ATT CTT TTG GAA AGT TTG   1178
Ile Phe Asp Glu Glu Lys Lys Lys Asn Phe Ile Leu Leu Glu Ser Leu
 255                 260                 265
```

```
ATC AGT ACT TTG TAC AAG AAA CCT AAA TCG GCC AAG TTC AAG GTT GTT    1226
Ile Ser Thr Leu Tyr Lys Lys Pro Lys Ser Ala Lys Phe Lys Val Val
    270                 275                 280

GAG AAA ATT TTG GGT AAA GAT TTA GTT GGA CTC AAA TAC AAG CCA TTG    1274
Glu Lys Ile Leu Gly Lys Asp Leu Val Gly Leu Lys Tyr Lys Pro Leu
285                 290                 295                 300

TTC AAT TAC TTT TAC GAA GAT TTC AAG GAT ACT GGG TTC AGA GTT ATT    1322
Phe Asn Tyr Phe Tyr Glu Asp Phe Lys Asp Thr Gly Phe Arg Val Ile
                    305                 310                 315

CCA GCC GAC TAT GTT ACC AAC GAT TCT GGT ACT GGT ATT GTC CAT CAA    1370
Pro Ala Asp Tyr Val Thr Asn Asp Ser Gly Thr Gly Ile Val His Gln
                320                 325                 330

GCC CCA TCC TAT GGT GAA GAG GAT TTC AAC AGT ACC AAA GCC GCA GGA    1418
Ala Pro Ser Tyr Gly Glu Glu Asp Phe Asn Ser Thr Lys Ala Ala Gly
            335                 340                 345

GTC ATC AAC GAA AAG AAG TTG CCA CCA AGC ATT GTT GAT GAT TCA GGG    1466
Val Ile Asn Glu Lys Lys Leu Pro Pro Ser Ile Val Asp Asp Ser Gly
350                 355                 360

AGA ATG GAA TCC AAT GTT CCT GAA ATT GCC GGA ATG TAC TTT AAG GAT    1514
Arg Met Glu Ser Asn Val Pro Glu Ile Ala Gly Met Tyr Phe Lys Asp
365                 370                 375                 380

GCC GAC AAG GTT ATT ATC AAG AAA TTA CTG GAA GAA GGT AGA CTC TTG    1562
Ala Asp Lys Val Ile Ile Lys Lys Leu Leu Glu Glu Gly Arg Leu Leu
                    385                 390                 395

GTC AAC ACC CAA GTA AAG CAC TCG TAC CCA TTC TGT TGG AGA TCA GAT    1610
Val Asn Thr Gln Val Lys His Ser Tyr Pro Phe Cys Trp Arg Ser Asp
                400                 405                 410

ACT CCA TTG ATG TAC AGA ACC GTC CCT GCA TGG TTT GTT AGA ATT GGC    1658
Thr Pro Leu Met Tyr Arg Thr Val Pro Ala Trp Phe Val Arg Ile Gly
            415                 420                 425

GAA GTC ATT CCT GAA ATG TTG GAT AAT GTT GAA AAG ACA AAC TGG GTT    1706
Glu Val Ile Pro Glu Met Leu Asp Asn Val Glu Lys Thr Asn Trp Val
        430                 435                 440

CCT TCC AAC ATT AAA GAT AAG AGA TTT TCC AAC TGG ATT GCC AAT GCC    1754
Pro Ser Asn Ile Lys Asp Lys Arg Phe Ser Asn Trp Ile Ala Asn Ala
445                 450                 455                 460

AGA GAC TGG AAC ATT TCC AGA AAT AGA TAC TGG GGT ACA CCA ATT CCA    1802
Arg Asp Trp Asn Ile Ser Arg Asn Arg Tyr Trp Gly Thr Pro Ile Pro
                    465                 470                 475

TTA TGG GTT TCT GAC GAT TTC GAA GAA ATG GTG TGT GTT GGT TCT ATC    1850
Leu Trp Val Ser Asp Asp Phe Glu Glu Met Val Cys Val Gly Ser Ile
                480                 485                 490

CAA GAA TTA AGG GAG TTA TCT GGT CGT GAT GAC ATT ACT GAT ATT CAC    1898
Gln Glu Leu Arg Glu Leu Ser Gly Arg Asp Asp Ile Thr Asp Ile His
            495                 500                 505

CGT GAG AGC ATC GAT TCT ATT ACC ATC CCA TCC AAA AAG GGT AAG GGC    1946
Arg Glu Ser Ile Asp Ser Ile Thr Ile Pro Ser Lys Lys Gly Lys Gly
510                 515                 520

CAA TTG AAG AGA ATC GAA GAA GTT TTT GAT TGT TGG TTT GAA TCT GGT    1994
Gln Leu Lys Arg Ile Glu Glu Val Phe Asp Cys Trp Phe Glu Ser Gly
525                 530                 535                 540

TCT ATG CCA TAT GCA TCC AAA CAT TAT CCA TTT GAA AAT GAA AAG AAG    2042
Ser Met Pro Tyr Ala Ser Lys His Tyr Pro Phe Glu Asn Glu Lys Lys
                    545                 550                 555

TTT TTG GAT GCC TTC CCG GCA AAT TTC ATT TCC GAA GGT TTA GAT CAA    2090
Phe Leu Asp Ala Phe Pro Ala Asn Phe Ile Ser Glu Gly Leu Asp Gln
                560                 565                 570

ACT AGA GGT TGG TTC TAC ACA TTG ACT GTA TTG GGT ACC CAT TTG TTC    2138
Thr Arg Gly Trp Phe Tyr Thr Leu Thr Val Leu Gly Thr His Leu Phe
            575                 580                 585
```

| | | | | | | | | | | | | | | | | |
|---|---|---|---|---|---|---|---|---|---|---|---|---|---|---|---|---|
| AAA | ACC | GCA | CCA | TAT | CAA | AAT | GTT | ATT | GTC | ACT | GGT | ATT | GTG | TTG | GCT | 2186 |
| Lys | Thr | Ala | Pro | Tyr | Gln | Asn | Val | Ile | Val | Thr | Gly | Ile | Val | Leu | Ala | |
| | 590 | | | | 595 | | | | | 600 | | | | | | |
| GCT | GAT | GGT | AAA | AAG | ATG | TCG | AAA | CGT | TTG | AAG | AAC | TAC | CCA | GAC | CCA | 2234 |
| Ala | Asp | Gly | Lys | Lys | Met | Ser | Lys | Arg | Leu | Lys | Asn | Tyr | Pro | Asp | Pro | |
| 605 | | | | | 610 | | | | | 615 | | | | | 620 | |
| ACC | TTG | GTG | TTG | GAG | AAA | TAT | GGT | GCC | GAT | GCG | TTG | AGA | TTG | TAC | TTG | 2282 |
| Thr | Leu | Val | Leu | Glu | Lys | Tyr | Gly | Ala | Asp | Ala | Leu | Arg | Leu | Tyr | Leu | |
| | | | | 625 | | | | | 630 | | | | | 635 | | |
| ATC | AAT | TCC | CCA | GTG | TTG | AGA | GCC | GAA | ACA | TTA | AAG | TTT | AAG | GAA | GAA | 2330 |
| Ile | Asn | Ser | Pro | Val | Leu | Arg | Ala | Glu | Thr | Leu | Lys | Phe | Lys | Glu | Glu | |
| | | | 640 | | | | | 645 | | | | | | 650 | | |
| GGT | GTT | AAG | GAA | ATT | GTT | TCC | AGT | GTG | TTA | TTG | CCA | TGG | TAC | AAC | TCC | 2378 |
| Gly | Val | Lys | Glu | Ile | Val | Ser | Ser | Val | Leu | Leu | Pro | Trp | Tyr | Asn | Ser | |
| | | 655 | | | | | 660 | | | | | | 665 | | | |
| TAC | AAG | TTT | TTA | AAG | GAT | GCT | GCT | GAC | CTT | TTC | AAG | AAG | GAT | AAT | GGC | 2426 |
| Tyr | Lys | Phe | Leu | Lys | Asp | Ala | Ala | Asp | Leu | Phe | Lys | Lys | Asp | Asn | Gly | |
| | 670 | | | | | 675 | | | | | 680 | | | | | |
| AAA | GAC | TTT | GTT | TAC | GAC | AGC | AGT | TTA | CAT | TCA | ACC | AAC | GTT | ATG | GAC | 2474 |
| Lys | Asp | Phe | Val | Tyr | Asp | Ser | Ser | Leu | His | Ser | Thr | Asn | Val | Met | Asp | |
| 685 | | | | | 690 | | | | | 695 | | | | | 700 | |
| AGA | TGG | TTA | TTA | GCA | TCA | ATC | CAA | TCT | TTG | ATC | AAG | TTT | ATT | CAC | GAA | 2522 |
| Arg | Trp | Leu | Leu | Ala | Ser | Ile | Gln | Ser | Leu | Ile | Lys | Phe | Ile | His | Glu | |
| | | | | 705 | | | | | 710 | | | | | 715 | | |
| GAA | ATG | ACT | GGG | TAC | AGA | TTA | TAT | ACT | GTT | GTT | CCT | AGA | TTG | TTG | CAT | 2570 |
| Glu | Met | Thr | Gly | Tyr | Arg | Leu | Tyr | Thr | Val | Val | Pro | Arg | Leu | Leu | His | |
| | | | 720 | | | | | 725 | | | | | 730 | | | |
| TTC | ATT | GAC | GAT | TTG | ACC | AAC | TGG | TAC | ATT | AGA | TTC | AAC | CGT | CGT | AGA | 2618 |
| Phe | Ile | Asp | Asp | Leu | Thr | Asn | Trp | Tyr | Ile | Arg | Phe | Asn | Arg | Arg | Arg | |
| | | 735 | | | | | 740 | | | | | 745 | | | | |
| ATC | AAG | GGA | TAT | GCT | TCC | GAC | GAT | GTT | GAA | GAC | ACC | CAA | AAG | GGT | CTC | 2666 |
| Ile | Lys | Gly | Tyr | Ala | Ser | Asp | Asp | Val | Glu | Asp | Thr | Gln | Lys | Gly | Leu | |
| | 750 | | | | | 755 | | | | | 760 | | | | | |
| AAT | ACA | TTG | GTC | GAA | GCG | TTG | TTG | ACA | TTG | TCT | AGA | GCA | ATG | GCT | CCT | 2714 |
| Asn | Thr | Leu | Val | Glu | Ala | Leu | Leu | Thr | Leu | Ser | Arg | Ala | Met | Ala | Pro | |
| 765 | | | | | 770 | | | | | 775 | | | | | 780 | |
| TTC | ACT | CCA | TAC | TTG | GCT | GAT | GGA | ATT | TAC | CAA | AGA | ATC | AAG | GTA | TAC | 2762 |
| Phe | Thr | Pro | Tyr | Leu | Ala | Asp | Gly | Ile | Tyr | Gln | Arg | Ile | Lys | Val | Tyr | |
| | | | | 785 | | | | | 790 | | | | | 795 | | |
| TTT | AAG | CAA | GAA | GAT | TTG | GAA | AAG | ATT | GCT | ATT | AAC | CCT | AAG | AAT | GTT | 2810 |
| Phe | Lys | Gln | Glu | Asp | Leu | Glu | Lys | Ile | Ala | Ile | Asn | Pro | Lys | Asn | Val | |
| | | | 800 | | | | | 805 | | | | | 810 | | | |
| GAC | TTG | AGA | TCA | GTG | CAT | TTC | TTG | AGC | TAC | CCA | TCA | GTG | AGA | CAA | GAG | 2858 |
| Asp | Leu | Arg | Ser | Val | His | Phe | Leu | Ser | Tyr | Pro | Ser | Val | Arg | Gln | Glu | |
| | | 815 | | | | | 820 | | | | | 825 | | | | |
| TTG | TTT | GAT | GAA | AAG | ATT | GAG | GTT | GCT | GTT | GCA | AGA | ATG | CAA | AAG | GTT | 2906 |
| Leu | Phe | Asp | Glu | Lys | Ile | Glu | Val | Ala | Val | Ala | Arg | Met | Gln | Lys | Val | |
| | 830 | | | | | 835 | | | | | 840 | | | | | |
| ATT | GAC | ATG | GCC | AGA | AAC | ATT | AGA | GAA | AAG | AAG | ATG | ATT | TCA | TTA | AAG | 2954 |
| Ile | Asp | Met | Ala | Arg | Asn | Ile | Arg | Glu | Lys | Lys | Met | Ile | Ser | Leu | Lys | |
| 845 | | | | | 850 | | | | | 855 | | | | | 860 | |
| ACT | CCA | TTG | AAT | GAG | TTG | GTG | GTT | TTG | AGT | GCA | GAT | GCT | GAT | TTG | TTG | 3002 |
| Thr | Pro | Leu | Asn | Glu | Leu | Val | Val | Leu | Ser | Ala | Asp | Ala | Asp | Leu | Leu | |
| | | | | 865 | | | | | 870 | | | | | 875 | | |
| AAG | GAC | ATT | GAT | TCT | TTG | AAA | GGA | TAC | ATT | AGT | GAT | GAG | TTG | AAT | GTG | 3050 |
| Lys | Asp | Ile | Asp | Ser | Leu | Lys | Gly | Tyr | Ile | Ser | Asp | Glu | Leu | Asn | Val | |
| | | | 880 | | | | | 885 | | | | | 890 | | | |
| AGA | AAT | GTT | GTC | ATC | ACA | TCA | GAC | GAA | GCC | AAG | TAC | TGT | GTT | GAG | TAC | 3098 |
| Arg | Asn | Val | Val | Ile | Thr | Ser | Asp | Glu | Ala | Lys | Tyr | Cys | Val | Glu | Tyr | |
| | | 895 | | | | | 900 | | | | | 905 | | | | |

| | | | | | | | | | | | | | | | | |
|---|---|---|---|---|---|---|---|---|---|---|---|---|---|---|---|---|
| TCG | TGT | GTT | GCT | GAT | TGG | CCA | GTG | TTG | GGT | AAA | AAG | TTA | AAG | TCA | GAC | 3146 |
| Ser | Cys | Val | Ala | Asp | Trp | Pro | Val | Leu | Gly | Lys | Lys | Leu | Lys | Ser | Asp | |
| 910 | | | | | 915 | | | | | 920 | | | | | | |
| GCC | AAA | AAA | GTC | AAG | GCA | GCA | TTG | CCT | AAA | GTT | TCT | TCT | GAA | GAA | GTT | 3194 |
| Ala | Lys | Lys | Val | Lys | Ala | Ala | Leu | Pro | Lys | Val | Ser | Ser | Glu | Glu | Val | |
| 925 | | | | | 930 | | | | | 935 | | | | | 940 | |
| CAA | AGA | TTT | GCC | GAG | TGT | GGT | AAA | ATC | ACT | GTT | GAT | GGT | ATT | GAC | TTG | 3242 |
| Gln | Arg | Phe | Ala | Glu | Cys | Gly | Lys | Ile | Thr | Val | Asp | Gly | Ile | Asp | Leu | |
| | | | | 945 | | | | | 950 | | | | | 955 | | |
| GTC | ACT | GAA | GAT | TTG | CAA | GTG | CAA | AGA | GGC | TTG | CCA | GCT | TCT | AAA | GCC | 3290 |
| Val | Thr | Glu | Asp | Leu | Gln | Val | Gln | Arg | Gly | Leu | Pro | Ala | Ser | Lys | Ala | |
| | | | 960 | | | | | 965 | | | | | 970 | | | |
| GAA | GAG | GGC | CAA | GAG | TTT | AGA | TCT | CAC | CAA | GAT | GTT | TTG | ATT | ATT | TTG | 3338 |
| Glu | Glu | Gly | Gln | Glu | Phe | Arg | Ser | His | Gln | Asp | Val | Leu | Ile | Ile | Leu | |
| | | 975 | | | | | 980 | | | | | 985 | | | | |
| GAT | GTC | AAT | TTG | CAC | CCT | GAA | TTG | GAA | AGT | GAA | GGT | TTG | GCA | AGA | GAG | 3386 |
| Asp | Val | Asn | Leu | His | Pro | Glu | Leu | Glu | Ser | Glu | Gly | Leu | Ala | Arg | Glu | |
| | 990 | | | | | 995 | | | | | 1000 | | | | | |
| TTG | ATT | AAC | CGT | ATC | CAA | AGA | TTG | CGT | AAA | AAG | GCT | GGT | TTG | AAT | ACC | 3434 |
| Leu | Ile | Asn | Arg | Ile | Gln | Arg | Leu | Arg | Lys | Lys | Ala | Gly | Leu | Asn | Thr | |
| 1005 | | | | | 1010 | | | | | 1015 | | | | | 1020 | |
| ACT | GAC | GAT | GTT | CAA | GTT | CAA | TAC | CGT | GTT | GTC | AAA | GAT | ACT | ATT | GAT | 3482 |
| Thr | Asp | Asp | Val | Gln | Val | Gln | Tyr | Arg | Val | Val | Lys | Asp | Thr | Ile | Asp | |
| | | | | 1025 | | | | | 1030 | | | | | 1035 | | |
| TTG | CCA | AAG | GTT | ATT | AAA | GAC | AAT | GAA | GAG | TTG | TTG | TTG | AAA | TCT | ACC | 3530 |
| Leu | Pro | Lys | Val | Ile | Lys | Asp | Asn | Glu | Glu | Leu | Leu | Leu | Lys | Ser | Thr | |
| | | | 1040 | | | | | 1045 | | | | | 1050 | | | |
| AAA | TAT | CCA | ATT | GAG | GAA | TTG | AAG | GAA | GCA | CAA | GAT | CTG | GCT | AAT | GTC | 3578 |
| Lys | Tyr | Pro | Ile | Glu | Glu | Leu | Lys | Glu | Ala | Gln | Asp | Leu | Ala | Asn | Val | |
| | | 1055 | | | | | 1060 | | | | | 1065 | | | | |
| ATT | ACC | GAT | GAA | GAG | CAA | ACA | ATC | AAC | GAT | ACA | GTG | TTT | AAT | TTG | CGT | 3626 |
| Ile | Thr | Asp | Glu | Glu | Gln | Thr | Ile | Asn | Asp | Thr | Val | Phe | Asn | Leu | Arg | |
| | 1070 | | | | | 1075 | | | | | 1080 | | | | | |

| | | | | | | |
|---|---|---|---|---|---|---|
| TTA | TTA | AAA | ATT | TAGATAGATA | ATTAATACAA | GATTTCCCAT GTACTGATAC | 3678 |
| Leu | Leu | Lys | Ile | | | | |
| 1085 | | | | | | | |

CAGCGCCTCC AACCACTGCT AGTGTTTTGC TATTTACTGT AG        3720

( 2 ) INFORMATION FOR SEQ ID NO:2:

( i ) SEQUENCE CHARACTERISTICS:
        ( A ) LENGTH: 1088 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ser | Leu | Gln | Glu | Ser | Asn | Asn | Asn | Ile | Pro | Gln | Gly | Ala | Phe | Ser |
| 1 | | | | 5 | | | | | 10 | | | | | 15 | |
| Phe | Pro | Lys | Glu | Glu | Glu | Ala | Val | Ile | Lys | His | Trp | Asp | Asp | Val | Asn |
| | | | 20 | | | | | 25 | | | | | 30 | | |
| Ala | Phe | Gln | Arg | Thr | Leu | Glu | Leu | Thr | Glu | Asp | Leu | Pro | Pro | Phe | Ala |
| | | | 35 | | | | | 40 | | | | | 45 | | |
| Phe | Phe | Asp | Gly | Pro | Pro | Phe | Ala | Thr | Gly | Thr | Pro | His | Tyr | Gly | His |
| | | 50 | | | | | 55 | | | | | 60 | | | |
| Ile | Leu | Ala | Ser | Thr | Val | Lys | Asp | Ile | Ile | Pro | Arg | Tyr | Ala | Thr | Met |
| 65 | | | | | 70 | | | | | 75 | | | | | 80 |
| Asn | Gly | Tyr | His | Val | Glu | Arg | Arg | Phe | Gly | Trp | Asp | Thr | His | Gly | Leu |
| | | | | 85 | | | | | 90 | | | | | 95 | |

```
Pro Val Glu His Glu Ile Asp Lys Lys Leu Asn Ile Thr Ser Lys Glu
            100                 105                 110

Asp Val Tyr Ala Met Gly Ile Asp Lys Tyr Asn Ala Glu Cys Arg Ala
        115                 120                 125

Ile Val Met Arg Tyr Ala Asp Glu Trp Arg Arg Thr Ile Lys Arg Leu
        130                 135                 140

Gly Arg Trp Ile Asp Met Asp Asn Asp Tyr Lys Thr Leu Tyr Pro Glu
145                     150                 155                 160

Phe Met Glu Ser Val Trp Trp Ala Phe Lys Glu Leu Phe Asn Lys Asp
                165                 170                 175

Ala Val Tyr Arg Gly Leu Arg Val Met Pro Tyr Ser Thr Ala Cys Thr
            180                 185                 190

Thr Pro Leu Ser Asn Phe Glu Ala Gln Gln Asn Tyr Lys Glu Val Asn
        195                 200                 205

Asp Pro Ala Leu Thr Ile Ser Phe Pro Leu Leu Asp Asn Glu Asp Thr
        210                 215                 220

Cys Leu Val Ala Trp Thr Thr Pro Trp Thr Leu Pro Ala Asn Leu
225                 230                 235                 240

Ala Leu Ala Val Asn Pro Lys Phe Glu Tyr Val Lys Ile Phe Asp Glu
                245                 250                 255

Glu Lys Lys Lys Asn Phe Ile Leu Leu Glu Ser Leu Ile Ser Thr Leu
            260                 265                 270

Tyr Lys Lys Pro Lys Ser Ala Lys Phe Lys Val Val Glu Lys Ile Leu
            275                 280                 285

Gly Lys Asp Leu Val Gly Leu Lys Tyr Lys Pro Leu Phe Asn Tyr Phe
        290                 295                 300

Tyr Glu Asp Phe Lys Asp Thr Gly Phe Arg Val Ile Pro Ala Asp Tyr
305                 310                 315                 320

Val Thr Asn Asp Ser Gly Thr Gly Ile Val His Gln Ala Pro Ser Tyr
                325                 330                 335

Gly Glu Glu Asp Phe Asn Ser Thr Lys Ala Ala Gly Val Ile Asn Glu
            340                 345                 350

Lys Lys Leu Pro Pro Ser Ile Val Asp Asp Ser Gly Arg Met Glu Ser
            355                 360                 365

Asn Val Pro Glu Ile Ala Gly Met Tyr Phe Lys Asp Ala Asp Lys Val
        370                 375                 380

Ile Ile Lys Lys Leu Leu Glu Glu Gly Arg Leu Leu Val Asn Thr Gln
385                 390                 395                 400

Val Lys His Ser Tyr Pro Phe Cys Trp Arg Ser Asp Thr Pro Leu Met
                405                 410                 415

Tyr Arg Thr Val Pro Ala Trp Phe Val Arg Ile Gly Glu Val Ile Pro
            420                 425                 430

Glu Met Leu Asp Asn Val Glu Lys Thr Asn Trp Val Pro Ser Asn Ile
        435                 440                 445

Lys Asp Lys Arg Phe Ser Asn Trp Ile Ala Asn Ala Arg Asp Trp Asn
        450                 455                 460

Ile Ser Arg Asn Arg Tyr Trp Gly Thr Pro Ile Pro Leu Trp Val Ser
465                 470                 475                 480

Asp Asp Phe Glu Glu Met Val Cys Val Gly Ser Ile Gln Glu Leu Arg
                485                 490                 495

Glu Leu Ser Gly Arg Asp Asp Ile Thr Asp Ile His Arg Glu Ser Ile
            500                 505                 510

Asp Ser Ile Thr Ile Pro Ser Lys Lys Gly Lys Gly Gln Leu Lys Arg
```

-continued

|     |     |     |     | 515 |     |     |     |     | 520 |     |     |     |     | 525 |     |     |     |
| --- | --- | --- | --- | --- | --- | --- | --- | --- | --- | --- | --- | --- | --- | --- | --- | --- | --- |

Ile Glu Glu Val Phe Asp Cys Trp Phe Glu Ser Ser Met Pro Tyr
530                535                540

Ala Ser Lys His Tyr Pro Phe Glu Asn Glu Lys Lys Phe Leu Asp Ala
545                550                555                560

Phe Pro Ala Asn Phe Ile Ser Glu Gly Leu Asp Gln Thr Arg Gly Trp
565                570                575

Phe Tyr Thr Leu Thr Val Leu Gly Thr His Leu Phe Lys Thr Ala Pro
580                585                590

Tyr Gln Asn Val Ile Val Thr Gly Ile Val Leu Ala Ala Asp Gly Lys
595                600                605

Lys Met Ser Lys Arg Leu Lys Asn Tyr Pro Asp Pro Thr Leu Val Leu
610                615                620

Glu Lys Tyr Gly Ala Asp Ala Leu Arg Leu Tyr Leu Ile Asn Ser Pro
625                630                635                640

Val Leu Arg Ala Glu Thr Leu Lys Phe Lys Glu Glu Gly Val Lys Glu
645                650                655

Ile Val Ser Ser Val Leu Leu Pro Trp Tyr Asn Ser Tyr Lys Phe Leu
660                665                670

Lys Asp Ala Ala Asp Leu Phe Lys Lys Asp Asn Gly Lys Asp Phe Val
675                680                685

Tyr Asp Ser Ser Leu His Ser Thr Asn Val Met Asp Arg Trp Leu Leu
690                695                700

Ala Ser Ile Gln Ser Leu Ile Lys Phe Ile His Glu Glu Met Thr Gly
705                710                715                720

Tyr Arg Leu Tyr Thr Val Val Pro Arg Leu Leu His Phe Ile Asp Asp
725                730                735

Leu Thr Asn Trp Tyr Ile Arg Phe Asn Arg Arg Arg Ile Lys Gly Tyr
740                745                750

Ala Ser Asp Asp Val Glu Asp Thr Gln Lys Gly Leu Asn Thr Leu Val
755                760                765

Glu Ala Leu Leu Thr Leu Ser Arg Ala Met Ala Pro Phe Thr Pro Tyr
770                775                780

Leu Ala Asp Gly Ile Tyr Gln Arg Ile Lys Val Tyr Phe Lys Gln Glu
785                790                795                800

Asp Leu Glu Lys Ile Ala Ile Asn Pro Lys Asn Val Asp Leu Arg Ser
805                810                815

Val His Phe Leu Ser Tyr Pro Ser Val Arg Gln Glu Leu Phe Asp Glu
820                825                830

Lys Ile Glu Val Ala Val Ala Arg Met Gln Lys Val Ile Asp Met Ala
835                840                845

Arg Asn Ile Arg Glu Lys Lys Met Ile Ser Leu Lys Thr Pro Leu Asn
850                855                860

Glu Leu Val Val Leu Ser Ala Asp Ala Asp Leu Leu Lys Asp Ile Asp
865                870                875                880

Ser Leu Lys Gly Tyr Ile Ser Asp Glu Leu Asn Val Arg Asn Val Val
885                890                895

Ile Thr Ser Asp Glu Ala Lys Tyr Cys Val Glu Tyr Ser Cys Val Ala
900                905                910

Asp Trp Pro Val Leu Gly Lys Lys Leu Lys Ser Asp Ala Lys Lys Val
915                920                925

Lys Ala Ala Leu Pro Lys Val Ser Ser Glu Glu Val Gln Arg Phe Ala
930                935                940

| | | | | | | | | | | | | | | | |
|---|---|---|---|---|---|---|---|---|---|---|---|---|---|---|---|
| Glu | Cys | Gly | Lys | Ile | Thr | Val | Asp | Gly | Ile | Asp | Leu | Val | Thr | Glu | Asp |
| 945 | | | | 950 | | | | | 955 | | | | | | 960 |
| Leu | Gln | Val | Gln | Arg | Gly | Leu | Pro | Ala | Ser | Lys | Ala | Glu | Glu | Gly | Gln |
| | | | | 965 | | | | | 970 | | | | | 975 | |
| Glu | Phe | Arg | Ser | His | Gln | Asp | Val | Leu | Ile | Ile | Leu | Asp | Val | Asn | Leu |
| | | | 980 | | | | | 985 | | | | | 990 | | |
| His | Pro | Glu | Leu | Glu | Ser | Glu | Gly | Leu | Ala | Arg | Glu | Leu | Ile | Asn | Arg |
| | | 995 | | | | | 1000 | | | | | 1005 | | | |
| Ile | Gln | Arg | Leu | Arg | Lys | Lys | Ala | Gly | Leu | Asn | Thr | Thr | Asp | Asp | Val |
| | 1010 | | | | | 1015 | | | | | 1020 | | | | |
| Gln | Val | Gln | Tyr | Arg | Val | Val | Lys | Asp | Thr | Ile | Asp | Leu | Pro | Lys | Val |
| 1025 | | | | | 1030 | | | | 1035 | | | | | | 1040 |
| Ile | Lys | Asp | Asn | Glu | Glu | Leu | Leu | Leu | Lys | Ser | Thr | Lys | Tyr | Pro | Ile |
| | | | | 1045 | | | | | 1050 | | | | | 1055 | |
| Glu | Glu | Leu | Lys | Glu | Ala | Gln | Asp | Leu | Ala | Asn | Val | Ile | Thr | Asp | Glu |
| | | | | 1060 | | | | | 1065 | | | | 1070 | | |
| Glu | Gln | Thr | Ile | Asn | Asp | Thr | Val | Phe | Asn | Leu | Arg | Leu | Leu | Lys | Ile |
| | | | 1075 | | | | 1080 | | | | | 1085 | | | |

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: Not Relevant ( i i ) MOLECULE TYPE: other nucleic acid
        ( A ) DESCRIPTION: /desc = "Oligonucleotide"

( i x ) FEATURE:
        ( A ) NAME/KEY: modified_base
        ( B ) LOCATION: 11
        ( D ) OTHER INFORMATION: /mod_base= i ( i x ) FEATURE:
        ( A ) NAME/KEY: modified_base
        ( B ) LOCATION: 20
        ( D ) OTHER INFORMATION: /mod_base= i ( i x ) FEATURE:
        ( A ) NAME/KEY: modified_base
        ( B ) LOCATION: 26
        ( D ) OTHER INFORMATION: /mod_base= i ( i x ) FEATURE:
        ( A ) NAME/KEY: modified_base
        ( B ) LOCATION: 29
        ( D ) OTHER INFORMATION: /mod_base= i ( x i ) SEQUENCE DESCRIPTION: SEQ ID NO:3:

GCGAATTCGG NTGGGAYACN CAYGGNSTNC C        31

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: Not Relevant ( i i ) MOLECULE TYPE: other nucleic acid
        ( A ) DESCRIPTION: /desc = "Oligonucleotide"

( i x ) FEATURE:
        ( A ) NAME/KEY: modified_base
        ( B ) LOCATION: 11
        ( D ) OTHER INFORMATION: /mod_base= i -continued ( i x ) FEATURE:
    ( A ) NAME/KEY: modified_base
    ( B ) LOCATION: 26
    ( D ) OTHER INFORMATION: /mod_base= i ( i x ) FEATURE:
    ( A ) NAME/KEY: modified_base
    ( B ) LOCATION: 29
    ( D ) OTHER INFORMATION: /mod_base= i ( x i ) SEQUENCE DESCRIPTION: SEQ ID NO:4:

GCGAATTCGG NTGGGAYTGY CAYGGNCTNC C          31

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: Not Relevant ( i i ) MOLECULE TYPE: other nucleic acid
        ( A ) DESCRIPTION: /desc = "oligonucleotide"

( i x ) FEATURE:
        ( A ) NAME/KEY: modified_base
        ( B ) LOCATION: 10
        ( D ) OTHER INFORMATION: /mod_base= i ( i x ) FEATURE:
        ( A ) NAME/KEY: modified_base
        ( B ) LOCATION: 16
        ( D ) OTHER INFORMATION: /mod_base = i ( i x ) FEATURE:
        ( A ) NAME/KEY: modified_base
        ( B ) LOCATION: 25
        ( D ) OTHER INFORMATION: /mod_base= i ( i x ) FEATURE:
        ( A ) NAME/KEY: modified_base
        ( B ) LOCATION: 28
        ( D ) OTHER INFORMATION: /mod_base= i ( i x ) FEATURE:
        ( A ) NAME/KEY: modified_base
        ( B ) LOCATION: 31
        ( D ) OTHER INFORMATION: /mod_base= i ( x i ) SEQUENCE DESCRIPTION: SEQ ID NO:5:

GCGAATTCGN CARCGNTAYT GGGGNRTNCC NAT          33

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: Not Relevant ( i i ) MOLECULE TYPE: other nucleic acid
        ( A ) DESCRIPTION: /desc = "oligonucleotide"

( i x ) FEATURE:
        ( A ) NAME/KEY: modified_base
        ( B ) LOCATION: 10
        ( D ) OTHER INFORMATION: /mod_base= i ( i x ) FEATURE:
        ( A ) NAME/KEY: modified_base
        ( B ) LOCATION: 16
        ( D ) OTHER INFORMATION: /mod_base= i ( i x ) FEATURE:
        ( A ) NAME/KEY: modified_base
        ( B ) LOCATION: 25

(D) OTHER INFORMATION: /mod_base= i (ix) FEATURE:
    (A) NAME/KEY: modified_base
    (B) LOCATION: 28
    (D) OTHER INFORMATION: /mod_base= i (ix) FEATURE:
    (A) NAME/KEY: modified_base
    (B) LOCATION: 31
    (D) OTHER INFORMATION: /mod_base= i (xi) SEQUENCE DESCRIPTION: SEQ ID NO:6:

GCGAATTCGN AAYCGNTWYT GGGGNACNCC NMT      33

(2) INFORMATION FOR SEQ ID NO:7:

(i) SEQUENCE CHARACTERISTICS:
        (A) LENGTH: 38 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "Oligonucleotide"

(ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 18
        (D) OTHER INFORMATION: /mod_base= i (ix) FEATURE:
        (A) NAME/KEY: modified_base
        (B) LOCATION: 21
        (D) OTHER INFORMATION: /mod_base= i (ix) FEATURE:
        (A) NAME/KEY: modified_base
        (B) LOCATION: 30
        (D) OTHER INFORMATION: /mod_base= i (ix) FEATURE:
        (A) NAME/KEY: modified_base
        (B) LOCATION: 33
        (D) OTHER INFORMATION: /mod_base= i (xi) SEQUENCE DESCRIPTION: SEQ ID NO:7:

GCGAATTCRA ACCANCCNCG NGTYTGRTCN WWNCCYTC      38

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "oligonucleotide"

(ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 6
        (D) OTHER INFORMATION: /mod_base= i (ix) FEATURE:

(A) NAME/KEY: modified_base
                (B) LOCATION: 12
                (D) OTHER INFORMATION: /mod_base= i (ix) FEATURE:
                (A) NAME/KEY: modified_base
                (B) LOCATION: 15
                (D) OTHER INFORMATION: /mod_base= i (ix) FEATURE:
                (A) NAME/KEY: modified_base
                (B) LOCATION: 18
                (D) OTHER INFORMATION: /mod_base= i (ix) FEATURE:
                (A) NAME/KEY: modified_base
                (B) LOCATION: 21
                (D) OTHER INFORMATION: /mod_base= i (xi) SEQUENCE DESCRIPTION: SEQ ID NO:8:

GGNARNGTCC ANGGNGTNGT NGTCCA                                                                      26

(2) INFORMATION FOR SEQ ID NO:9:

(i) SEQUENCE CHARACTERISTICS:
                (A) LENGTH: 32 base pairs
                (B) TYPE: nucleic acid
                (C) STRANDEDNESS: single
                (D) TOPOLOGY: Not Relevant (ii) MOLECULE TYPE: other nucleic acid
                (A) DESCRIPTION: /desc = "Oligonucleotide"

(ix) FEATURE:
                (A) NAME/KEY: modified_base
                (B) LOCATION: 12
                (D) OTHER INFORMATION: /mod_base= i (ix) FEATURE:
                (A) NAME/KEY: modified_base
                (B) LOCATION: 15
                (D) OTHER INFORMATION: /mod_base= i (ix) FEATURE:
                (A) NAME/KEY: modified_base
                (B) LOCATION: 24
                (D) OTHER INFORMATION: /mod_base= i (ix) FEATURE:
                (A) NAME/KEY: modified_base
                (B) LOCATION: 27
                (D) OTHER INFORMATION: /mod_base= i (xi) SEQUENCE DESCRIPTION: SEQ ID NO:9:

TWYATGGART CNACNTGGTG GGYNTTNAAR CA                                                               32

(2) INFORMATION FOR SEQ ID NO:10:

(i) SEQUENCE CHARACTERISTICS:
                (A) LENGTH: 20 base pairs
                (B) TYPE: nucleic acid
                (C) STRANDEDNESS: single
                (D) TOPOLOGY: Not Relevant (ii) MOLECULE TYPE: other nucleic acid
                (A) DESCRIPTION: /desc = "Oligonucleotide"

(xi) SEQUENCE DESCRIPTION: SEQ ID NO:10:

GATTGCGAAT TCGAACCAGC                                                                             20

(2) INFORMATION FOR SEQ ID NO:11:

(i) SEQUENCE CHARACTERISTICS:
                (A) LENGTH: 20 base pairs ( B ) TYPE: nucleic acid
( C ) STRANDEDNESS: single
( D ) TOPOLOGY: Not Relevant ( i i ) MOLECULE TYPE: other nucleic acid
( A ) DESCRIPTION: /desc = "Oligonucleotide"

( x i ) SEQUENCE DESCRIPTION: SEQ ID NO:11:

GGAGATGGAT TGATATGGAC 20

( 2 ) INFORMATION FOR SEQ ID NO:12:

( i ) SEQUENCE CHARACTERISTICS:
( A ) LENGTH: 56 base pairs
( B ) TYPE: nucleic acid
( C ) STRANDEDNESS: single
( D ) TOPOLOGY: Not Relevant ( i i ) MOLECULE TYPE: other nucleic acid
( A ) DESCRIPTION: /desc = "Oligonucleotide"

( x i ) SEQUENCE DESCRIPTION: SEQ ID NO:12:

CTGCAGCTGA GAAGGAGAGG ATCCATGTCG TTACAAGAAA GCAACAACAA TATCCC 56

( 2 ) INFORMATION FOR SEQ ID NO:13:

( i ) SEQUENCE CHARACTERISTICS:
( A ) LENGTH: 39 base pairs
( B ) TYPE: nucleic acid
( C ) STRANDEDNESS: single
( D ) TOPOLOGY: Not Relevant ( i i ) MOLECULE TYPE: other nucleic acid
( A ) DESCRIPTION: /desc = "Oligonucleotide"

( x i ) SEQUENCE DESCRIPTION: SEQ ID NO:13:

CGGAATTCAC TAAATTTTTA ATAAACGCAA ATTAAACAC 39

( 2 ) INFORMATION FOR SEQ ID NO:14:

( i ) SEQUENCE CHARACTERISTICS:
( A ) LENGTH: 32 base pairs
( B ) TYPE: nucleic acid
( C ) STRANDEDNESS: single
( D ) TOPOLOGY: Not Relevant ( i i ) MOLECULE TYPE: other nucleic acid
( A ) DESCRIPTION: /desc = "Oligonucleotide"

( x i ) SEQUENCE DESCRIPTION: SEQ ID NO:14:

CCAAGAAGCT TGAAGTAATA ATAGGCGCAT GC 32

( 2 ) INFORMATION FOR SEQ ID NO:15:

( i ) SEQUENCE CHARACTERISTICS:
( A ) LENGTH: 30 base pairs
( B ) TYPE: nucleic acid
( C ) STRANDEDNESS: single
( D ) TOPOLOGY: Not Relevant ( i i ) MOLECULE TYPE: other nucleic acid
( A ) DESCRIPTION: /desc = "Oligonucleotide"

( x i ) SEQUENCE DESCRIPTION: SEQ ID NO:15:

CGTACTGCAG GATTGTATGC TTGGTATAGC 30

( 2 ) INFORMATION FOR SEQ ID NO:16:

( i ) SEQUENCE CHARACTERISTICS:
( A ) LENGTH: 30 base pairs (B) TYPE: nucleic acid
(C) STRANDEDNESS: single
(D) TOPOLOGY: Not Relevant (i i) MOLECULE TYPE: other nucleic acid
(A) DESCRIPTION: /desc = "Oligonucleotide"

(x i) SEQUENCE DESCRIPTION: SEQ ID NO:16:

GGAATTCTGA AAACAACTCA TATAAATACG                        30

(2) INFORMATION FOR SEQ ID NO:17:

(i) SEQUENCE CHARACTERISTICS:
(A) LENGTH: 32 base pairs
(B) TYPE: nucleic acid
(C) STRANDEDNESS: single
(D) TOPOLOGY: Not Relevant (i i) MOLECULE TYPE: other nucleic acid
(A) DESCRIPTION: /desc = "Oligonucleotide"

(x i) SEQUENCE DESCRIPTION: SEQ ID NO:17:

GAGGCGCCCT CTTATCAATC CCCTCCTCAA CC                     32

(2) INFORMATION FOR SEQ ID NO:18:

(i) SEQUENCE CHARACTERISTICS:
(A) LENGTH: 42 base pairs
(B) TYPE: nucleic acid
(C) STRANDEDNESS: single
(D) TOPOLOGY: linear (x i) SEQUENCE DESCRIPTION: SEQ ID NO:18:

GTTATTATCA AGAAATTATC TGAAGAAGGT AGACTCTTGG TC           42

(2) INFORMATION FOR SEQ ID NO:19:

(i) SEQUENCE CHARACTERISTICS:
(A) LENGTH: 38 base pairs
(B) TYPE: nucleic acid
(C) STRANDEDNESS: single
(D) TOPOLOGY: linear (x i) SEQUENCE DESCRIPTION: SEQ ID NO:19:

GAAGGAAGCA CAAGATTCTG CTAATGTCAT TACCGATG               38

(2) INFORMATION FOR SEQ ID NO:20:

(i) SEQUENCE CHARACTERISTICS:
(A) LENGTH: 39 base pairs
(B) TYPE: nucleic acid
(C) STRANDEDNESS: single
(D) TOPOLOGY: linear (x i) SEQUENCE DESCRIPTION: SEQ ID NO:20:

GTAATGACAT TAGCAGAATC TTGTGCTTCC TTCAATTCC              39

(2) INFORMATION FOR SEQ ID NO:21:

(i) SEQUENCE CHARACTERISTICS:
(A) LENGTH: 40 base pairs
(B) TYPE: nucleic acid
(C) STRANDEDNESS: single
(D) TOPOLOGY: linear (x i) SEQUENCE DESCRIPTION: SEQ ID NO:21:

GAGTCTACCT TCTTCAGATA ATTTCTTGAT AATAACCTTG             40

( 2 ) INFORMATION FOR SEQ ID NO:22:

( i ) SEQUENCE CHARACTERISTICS:
        ( A ) LENGTH: 3720 base pairs
        ( B ) TYPE: nucleic acid
        ( C ) STRANDEDNESS: double
        ( D ) TOPOLOGY: Not Relevant ( i x ) FEATURE:
        ( A ) NAME/KEY: CDS
        ( B ) LOCATION: 375..3638

( x i ) SEQUENCE DESCRIPTION: SEQ ID NO:22:

```
TTTTGGATAC  TATCAAACAA  GAGGAATGAC  TAATACAGAA  TTAGTGTTAC  GAATCAATGG        60

CACTACAGCA  ACTTTCAACA  AAATAATCTA  CGTTCAAAAT  ATAATATATA  CTATTAAATA       120

AAATCAAATA  ATAAAATAAT  TTTAAAGAAA  GTAGTACCAG  CTCTTTTTTT  TGTTTCCGTT       180

TATACCATCC  AAATCAATTC  CTATTAGTCG  GGATCATTGA  TTGAGTGAGT  GAGTGAGTGA       240

TGACTGAGCA  GCAGGTCGTG  CGATCTCACG  ATATGTGTCA  CAACGAAACC  TGAAAAAAAA       300

AAAGACTCAA  AAATTTTTTT  CTTCTCTTCC  GTCTATTACT  CATCTATACA  TCAACAAGTT       360

GGTACTTTAC  AGAT ATG TCG TTA CAA GAA AGC AAC AAC AAT ATC CCT CAA            410
              Met Ser Leu Gln Glu Ser Asn Asn Asn Ile Pro Gln
               1               5                        10

GGT GCT TTT AGT TTT CCT AAG GAA GAA GAA GCA GTT ATC AAA CAT TGG              458
Gly Ala Phe Ser Phe Pro Lys Glu Glu Glu Ala Val Ile Lys His Trp
         15                  20                  25

GAT GAT GTC AAT GCT TTT CAA AGA ACT TTA GAG TTG ACT GAA GAT TTA              506
Asp Asp Val Asn Ala Phe Gln Arg Thr Leu Glu Leu Thr Glu Asp Leu
         30                  35                  40

CCG CCA TTT GCG TTT TTT GAC GGA CCA CCA TTT GCC ACT GGT ACT CCT              554
Pro Pro Phe Ala Phe Phe Asp Gly Pro Pro Phe Ala Thr Gly Thr Pro
 45                  50                  55                  60

CAT TAC GGG CAC ATT TTG GCC TCT ACA GTC AAA GAT ATT ATC CCA CGT              602
His Tyr Gly His Ile Leu Ala Ser Thr Val Lys Asp Ile Ile Pro Arg
                 65                  70                  75

TAT GCC ACC ATG AAC GGG TAT CAT GTG GAG AGA AGA TTC GGT TGG GAT              650
Tyr Ala Thr Met Asn Gly Tyr His Val Glu Arg Arg Phe Gly Trp Asp
             80                  85                  90

ACC CAC GGT TTG CCA GTA GAA CAT GAA ATT GAC AAA AAG TTG AAC ATT              698
Thr His Gly Leu Pro Val Glu His Glu Ile Asp Lys Lys Leu Asn Ile
         95                 100                 105

ACC TCG AAA GAA GAT GTT TAT GCC ATG GGT ATT GAC AAG TAC AAT GCT              746
Thr Ser Lys Glu Asp Val Tyr Ala Met Gly Ile Asp Lys Tyr Asn Ala
        110                 115                 120

GAA TGT CGT GCA ATT GTG ATG AGA TAC GCT GAT GAA TGG CGT AGA ACA              794
Glu Cys Arg Ala Ile Val Met Arg Tyr Ala Asp Glu Trp Arg Arg Thr
125                 130                 135                 140

ATC AAG AGA TTG GGG AGA TGG ATT GAT ATG GAC AAC GAT TAC AAA ACC              842
Ile Lys Arg Leu Gly Arg Trp Ile Asp Met Asp Asn Asp Tyr Lys Thr
                145                 150                 155

TTG TAC CCT GAA TTT ATG GAA TCT GTG TGG TGG GCT TTC AAG GAG TTG              890
Leu Tyr Pro Glu Phe Met Glu Ser Val Trp Trp Ala Phe Lys Glu Leu
            160                 165                 170

TTT AAC AAG GAT GCC GTT TAT AGA GGT TTG AGG GTC ATG CCT TAT TCC              938
Phe Asn Lys Asp Ala Val Tyr Arg Gly Leu Arg Val Met Pro Tyr Ser
        175                 180                 185

ACT GCT TGT ACC ACA CCA TTG TCG AAC TTT GAA GCC CAA CAA AAC TAT              986
Thr Ala Cys Thr Thr Pro Leu Ser Asn Phe Glu Ala Gln Gln Asn Tyr
    190                 195                 200

AAA GAA GTT AAC GAC CCA GCA CTT ACT ATT TCG TTC CCA TTG CTT GAT             1034
Lys Glu Val Asn Asp Pro Ala Leu Thr Ile Ser Phe Pro Leu Leu Asp
```

|  |  |  |  |  |  |  |  |  |  |  |  |  |  |  |  |  |
|---|---|---|---|---|---|---|---|---|---|---|---|---|---|---|---|---|
| 205 |  |  |  |  |  | 210 |  |  |  |  | 215 |  |  |  | 220 |  |
| AAC | GAA | GAC | ACT | TGT | TTG | GTT | GCT | TGG | ACT | ACC | ACG | CCA | TGG | ACC | TTA | 1082 |
| Asn | Glu | Asp | Thr | Cys<br>225 | Leu | Val | Ala | Trp<br>230 | Thr | Thr | Thr | Pro | Trp<br>235 | Thr | Leu |  |
| CCT | GCA | AAT | CTT | GCG | TTA | GCA | GTT | AAT | CCA | AAG | TTT | GAG | TAT | GTA | AAG | 1130 |
| Pro | Ala | Asn | Leu<br>240 | Ala | Leu | Ala | Val | Asn<br>245 | Pro | Lys | Phe | Glu | Tyr<br>250 | Val | Lys |  |
| ATT | TTT | GAT | GAG | GAA | AAA | AAG | AAA | AAC | TTT | ATT | CTT | TTG | GAA | AGT | TTG | 1178 |
| Ile | Phe | Asp<br>255 | Glu | Glu | Lys | Lys | Lys<br>260 | Asn | Phe | Ile | Leu | Leu<br>265 | Glu | Ser | Leu |  |
| ATC | AGT | ACT | TTG | TAC | AAG | AAA | CCT | AAA | TCG | GCC | AAG | TTC | AAG | GTT | GTT | 1226 |
| Ile | Ser<br>270 | Thr | Leu | Tyr | Lys | Lys<br>275 | Pro | Lys | Ser | Ala | Lys<br>280 | Phe | Lys | Val | Val |  |
| GAG | AAA | ATT | TTG | GGT | AAA | GAT | TTA | GTT | GGA | CTC | AAA | TAC | AAG | CCA | TTG | 1274 |
| Glu<br>285 | Lys | Ile | Leu | Gly | Lys<br>290 | Asp | Leu | Val | Gly | Leu<br>295 | Lys | Tyr | Lys | Pro | Leu<br>300 |  |
| TTC | AAT | TAC | TTT | TAC | GAA | GAT | TTC | AAG | GAT | ACT | GGG | TTC | AGA | GTT | ATT | 1322 |
| Phe | Asn | Tyr | Phe | Tyr<br>305 | Glu | Asp | Phe | Lys | Asp<br>310 | Thr | Gly | Phe | Arg | Val<br>315 | Ile |  |
| CCA | GCC | GAC | TAT | GTT | ACC | AAC | GAT | TCT | GGT | ACT | GGT | ATT | GTC | CAT | CAA | 1370 |
| Pro | Ala | Asp | Tyr<br>320 | Val | Thr | Asn | Asp | Ser<br>325 | Gly | Thr | Gly | Ile | Val<br>330 | His | Gln |  |
| GCC | CCA | TCC | TAT | GGT | GAA | GAG | GAT | TTC | AAC | AGT | ACC | AAA | GCC | GCA | GGA | 1418 |
| Ala | Pro | Ser<br>335 | Tyr | Gly | Glu | Glu | Asp<br>340 | Phe | Asn | Ser | Thr | Lys<br>345 | Ala | Ala | Gly |  |
| GTC | ATC | AAC | GAA | AAG | AAG | TTG | CCA | CCA | AGC | ATT | GTT | GAT | GAT | TCA | GGG | 1466 |
| Val | Ile | Asn<br>350 | Glu | Lys | Lys | Leu | Pro<br>355 | Pro | Ser | Ile | Val | Asp<br>360 | Asp | Ser | Gly |  |
| AGA | ATG | GAA | TCC | AAT | GTT | CCT | GAA | ATT | GCC | GGA | ATG | TAC | TTT | AAG | GAT | 1514 |
| Arg<br>365 | Met | Glu | Ser | Asn | Val<br>370 | Pro | Glu | Ile | Ala | Gly<br>375 | Met | Tyr | Phe | Lys | Asp<br>380 |  |
| GCC | GAC | AAG | GTT | ATT | ATC | AAG | AAA | TTA | TCT | GAA | GAA | GGT | AGA | CTC | TTG | 1562 |
| Ala | Asp | Lys | Val | Ile<br>385 | Ile | Lys | Lys | Leu | Ser<br>390 | Glu | Glu | Gly | Arg | Leu<br>395 | Leu |  |
| GTC | AAC | ACC | CAA | GTA | AAG | CAC | TCG | TAC | CCA | TTC | TGT | TGG | AGA | TCA | GAT | 1610 |
| Val | Asn | Thr | Gln<br>400 | Val | Lys | His | Ser | Tyr<br>405 | Pro | Phe | Cys | Trp | Arg<br>410 | Ser | Asp |  |
| ACT | CCA | TTG | ATG | TAC | AGA | ACC | GTC | CCT | GCA | TGG | TTT | GTT | AGA | ATT | GGC | 1658 |
| Thr | Pro | Leu<br>415 | Met | Tyr | Arg | Thr | Val<br>420 | Pro | Ala | Trp | Phe | Val<br>425 | Arg | Ile | Gly |  |
| GAA | GTC | ATT | CCT | GAA | ATG | TTG | GAT | AAT | GTT | GAA | AAG | ACA | AAC | TGG | GTT | 1706 |
| Glu | Val | Ile<br>430 | Pro | Glu | Met | Leu<br>435 | Asp | Asn | Val | Glu | Lys<br>440 | Thr | Asn | Trp | Val |  |
| CCT | TCC | AAC | ATT | AAA | GAT | AAG | AGA | TTT | TCC | AAC | TGG | ATT | GCC | AAT | GCC | 1754 |
| Pro | Ser | Asn | Ile | Lys<br>450 | Asp | Lys | Arg | Phe | Ser<br>455 | Asn | Trp | Ile | Ala | Asn | Ala<br>460 |  |
| AGA | GAC | TGG | AAC | ATT | TCC | AGA | AAT | AGA | TAC | TGG | GGT | ACA | CCA | ATT | CCA | 1802 |
| Arg | Asp | Trp | Asn | Ile<br>465 | Ser | Arg | Asn | Arg | Tyr<br>470 | Trp | Gly | Thr | Pro | Ile<br>475 | Pro |  |
| TTA | TGG | GTT | TCT | GAC | GAT | TTC | GAA | GAA | ATG | GTG | TGT | GTT | GGT | TCT | ATC | 1850 |
| Leu | Trp | Val | Ser<br>480 | Asp | Asp | Phe | Glu | Glu<br>485 | Met | Val | Cys | Val | Gly<br>490 | Ser | Ile |  |
| CAA | GAA | TTA | AGG | GAG | TTA | TCT | GGT | CGT | GAT | GAC | ATT | ACT | GAT | ATT | CAC | 1898 |
| Gln | Glu | Leu<br>495 | Arg | Glu | Leu | Ser<br>500 | Gly | Arg | Asp | Asp | Ile<br>505 | Thr | Asp | Ile | His |  |
| CGT | GAG | AGC | ATC | GAT | TCT | ATT | ACC | ATC | CCA | TCC | AAA | AAG | GGT | AAG | GGC | 1946 |
| Arg | Glu | Ser<br>510 | Ile | Asp | Ser | Ile<br>515 | Thr | Ile | Pro | Ser | Lys<br>520 | Lys | Gly | Lys | Gly |  |
| CAA | TTG | AAG | AGA | ATC | GAA | GAA | GTT | TTT | GAT | TGT | TGG | TTT | GAA | TCT | GGT | 1994 |
| Gln | Leu | Lys | Arg | Ile | Glu | Glu | Val | Phe | Asp | Cys | Trp | Phe | Glu | Ser | Gly |  |

-continued

| | | | | | | | | | | | | | | | |
|---|---|---|---|---|---|---|---|---|---|---|---|---|---|---|---|
|525| | | | |530| | | | |535| | | | |540|

| TCT | ATG | CCA | TAT | GCA | TCC | AAA | CAT | TAT | CCA | TTT | GAA | AAT | GAA | AAG | AAG | 2042 |
|---|---|---|---|---|---|---|---|---|---|---|---|---|---|---|---|---|
| Ser | Met | Pro | Tyr | Ala | Ser | Lys | His | Tyr | Pro | Phe | Glu | Asn | Glu | Lys | Lys | |
| | | | | 545 | | | | | 550 | | | | | 555 | | |

| TTT | TTG | GAT | GCC | TTC | CCG | GCA | AAT | TTC | ATT | TCC | GAA | GGT | TTA | GAT | CAA | 2090 |
|---|---|---|---|---|---|---|---|---|---|---|---|---|---|---|---|---|
| Phe | Leu | Asp | Ala | Phe | Pro | Ala | Asn | Phe | Ile | Ser | Glu | Gly | Leu | Asp | Gln | |
| | | | 560 | | | | | 565 | | | | | 570 | | | |

| ACT | AGA | GGT | TGG | TTC | TAC | ACA | TTG | ACT | GTA | TTG | GGT | ACC | CAT | TTG | TTC | 2138 |
|---|---|---|---|---|---|---|---|---|---|---|---|---|---|---|---|---|
| Thr | Arg | Gly | Trp | Phe | Tyr | Thr | Leu | Thr | Val | Leu | Gly | Thr | His | Leu | Phe | |
| | | 575 | | | | | 580 | | | | | 585 | | | | |

| AAA | ACC | GCA | CCA | TAT | CAA | AAT | GTT | ATT | GTC | ACT | GGT | ATT | GTG | TTG | GCT | 2186 |
|---|---|---|---|---|---|---|---|---|---|---|---|---|---|---|---|---|
| Lys | Thr | Ala | Pro | Tyr | Gln | Asn | Val | Ile | Val | Thr | Gly | Ile | Val | Leu | Ala | |
| | 590 | | | | | 595 | | | | | 600 | | | | | |

| GCT | GAT | GGT | AAA | AAG | ATG | TCG | AAA | CGT | TTG | AAG | AAC | TAC | CCA | GAC | CCA | 2234 |
|---|---|---|---|---|---|---|---|---|---|---|---|---|---|---|---|---|
| Ala | Asp | Gly | Lys | Lys | Met | Ser | Lys | Arg | Leu | Lys | Asn | Tyr | Pro | Asp | Pro | |
| 605 | | | | | 610 | | | | | 615 | | | | | 620 | |

| ACC | TTG | GTG | TTG | GAG | AAA | TAT | GGT | GCC | GAT | GCG | TTG | AGA | TTG | TAC | TTG | 2282 |
|---|---|---|---|---|---|---|---|---|---|---|---|---|---|---|---|---|
| Thr | Leu | Val | Leu | Glu | Lys | Tyr | Gly | Ala | Asp | Ala | Leu | Arg | Leu | Tyr | Leu | |
| | | | | 625 | | | | | 630 | | | | | 635 | | |

| ATC | AAT | TCC | CCA | GTG | TTG | AGA | GCC | GAA | ACA | TTA | AAG | TTT | AAG | GAA | GAA | 2330 |
|---|---|---|---|---|---|---|---|---|---|---|---|---|---|---|---|---|
| Ile | Asn | Ser | Pro | Val | Leu | Arg | Ala | Glu | Thr | Leu | Lys | Phe | Lys | Glu | Glu | |
| | | | 640 | | | | | 645 | | | | | 650 | | | |

| GGT | GTT | AAG | GAA | ATT | GTT | TCC | AGT | GTG | TTA | TTG | CCA | TGG | TAC | AAC | TCC | 2378 |
|---|---|---|---|---|---|---|---|---|---|---|---|---|---|---|---|---|
| Gly | Val | Lys | Glu | Ile | Val | Ser | Ser | Val | Leu | Leu | Pro | Trp | Tyr | Asn | Ser | |
| | | 655 | | | | | 660 | | | | | 665 | | | | |

| TAC | AAG | TTT | TTA | AAG | GAT | GCT | GCT | GAC | CTT | TTC | AAG | AAG | GAT | AAT | GGC | 2426 |
|---|---|---|---|---|---|---|---|---|---|---|---|---|---|---|---|---|
| Tyr | Lys | Phe | Leu | Lys | Asp | Ala | Ala | Asp | Leu | Phe | Lys | Lys | Asp | Asn | Gly | |
| | 670 | | | | | 675 | | | | | 680 | | | | | |

| AAA | GAC | TTT | GTT | TAC | GAC | AGC | AGT | TTA | CAT | TCA | ACC | AAC | GTT | ATG | GAC | 2474 |
|---|---|---|---|---|---|---|---|---|---|---|---|---|---|---|---|---|
| Lys | Asp | Phe | Val | Tyr | Asp | Ser | Ser | Leu | His | Ser | Thr | Asn | Val | Met | Asp | |
| 685 | | | | | 690 | | | | | 695 | | | | | 700 | |

| AGA | TGG | TTA | TTA | GCA | TCA | ATC | CAA | TCT | TTG | ATC | AAG | TTT | ATT | CAC | GAA | 2522 |
|---|---|---|---|---|---|---|---|---|---|---|---|---|---|---|---|---|
| Arg | Trp | Leu | Leu | Ala | Ser | Ile | Gln | Ser | Leu | Ile | Lys | Phe | Ile | His | Glu | |
| | | | | 705 | | | | | 710 | | | | | 715 | | |

| GAA | ATG | ACT | GGG | TAC | AGA | TTA | TAT | ACT | GTT | GTT | CCT | AGA | TTG | TTG | CAT | 2570 |
|---|---|---|---|---|---|---|---|---|---|---|---|---|---|---|---|---|
| Glu | Met | Thr | Gly | Tyr | Arg | Leu | Tyr | Thr | Val | Val | Pro | Arg | Leu | Leu | His | |
| | | | 720 | | | | | 725 | | | | | 730 | | | |

| TTC | ATT | GAC | GAT | TTG | ACC | AAC | TGG | TAC | ATT | AGA | TTC | AAC | CGT | CGT | AGA | 2618 |
|---|---|---|---|---|---|---|---|---|---|---|---|---|---|---|---|---|
| Phe | Ile | Asp | Asp | Leu | Thr | Asn | Trp | Tyr | Ile | Arg | Phe | Asn | Arg | Arg | Arg | |
| | | 735 | | | | | 740 | | | | | 745 | | | | |

| ATC | AAG | GGA | TAT | GCT | TCC | GAC | GAT | GTT | GAA | GAC | ACC | CAA | AAG | GGT | CTC | 2666 |
|---|---|---|---|---|---|---|---|---|---|---|---|---|---|---|---|---|
| Ile | Lys | Gly | Tyr | Ala | Ser | Asp | Asp | Val | Glu | Asp | Thr | Gln | Lys | Gly | Leu | |
| | 750 | | | | | 755 | | | | | 760 | | | | | |

| AAT | ACA | TTG | GTC | GAA | GCG | TTG | TTG | ACA | TTG | TCT | AGA | GCA | ATG | GCT | CCT | 2714 |
|---|---|---|---|---|---|---|---|---|---|---|---|---|---|---|---|---|
| Asn | Thr | Leu | Val | Glu | Ala | Leu | Leu | Thr | Leu | Ser | Arg | Ala | Met | Ala | Pro | |
| 765 | | | | | 770 | | | | | 775 | | | | | 780 | |

| TTC | ACT | CCA | TAC | TTG | GCT | GAT | GGA | ATT | TAC | CAA | AGA | ATC | AAG | GTA | TAC | 2762 |
|---|---|---|---|---|---|---|---|---|---|---|---|---|---|---|---|---|
| Phe | Thr | Pro | Tyr | Leu | Ala | Asp | Gly | Ile | Tyr | Gln | Arg | Ile | Lys | Val | Tyr | |
| | | | | 785 | | | | | 790 | | | | | 795 | | |

| TTT | AAG | CAA | GAA | GAT | TTG | GAA | AAG | ATT | GCT | ATT | AAC | CCT | AAG | AAT | GTT | 2810 |
|---|---|---|---|---|---|---|---|---|---|---|---|---|---|---|---|---|
| Phe | Lys | Gln | Glu | Asp | Leu | Glu | Lys | Ile | Ala | Ile | Asn | Pro | Lys | Asn | Val | |
| | | | | 800 | | | | | 805 | | | | | 810 | | |

| GAC | TTG | AGA | TCA | GTG | CAT | TTC | TTG | AGC | TAC | CCA | TCA | GTG | AGA | CAA | GAG | 2858 |
|---|---|---|---|---|---|---|---|---|---|---|---|---|---|---|---|---|
| Asp | Leu | Arg | Ser | Val | His | Phe | Leu | Ser | Tyr | Pro | Ser | Val | Arg | Gln | Glu | |
| | | 815 | | | | | 820 | | | | | 825 | | | | |

| TTG | TTT | GAT | GAA | AAG | ATT | GAG | GTT | GCT | GTT | GCA | AGA | ATG | CAA | AAG | GTT | 2906 |
|---|---|---|---|---|---|---|---|---|---|---|---|---|---|---|---|---|
| Leu | Phe | Asp | Glu | Lys | Ile | Glu | Val | Ala | Val | Ala | Arg | Met | Gln | Lys | Val | |
| | 830 | | | | | 835 | | | | | 840 | | | | | |

| ATT | GAC | ATG | GCC | AGA | AAC | ATT | AGA | GAA | AAG | AAG | ATG | ATT | TCA | TTA | AAG | 2954 |
|---|---|---|---|---|---|---|---|---|---|---|---|---|---|---|---|---|
| Ile | Asp | Met | Ala | Arg | Asn | Ile | Arg | Glu | Lys | Lys | Met | Ile | Ser | Leu | Lys | |

|  |  |  |  |  |  |  |  |  |  |  |  |  |  |  |  |
|---|---|---|---|---|---|---|---|---|---|---|---|---|---|---|---|
| 845 |  |  |  |  | 850 |  |  |  |  | 855 |  |  |  |  | 860 |

```
ACT  CCA  TTG  AAT  GAG  TTG  GTG  GTT  TTG  AGT  GCA  GAT  GCT  GAT  TTG  TTG    3002
Thr  Pro  Leu  Asn  Glu  Leu  Val  Val  Leu  Ser  Ala  Asp  Ala  Asp  Leu  Leu
                    865                     870                     875

AAG  GAC  ATT  GAT  TCT  TTG  AAA  GGA  TAC  ATT  AGT  GAT  GAG  TTG  AAT  GTG    3050
Lys  Asp  Ile  Asp  Ser  Leu  Lys  Gly  Tyr  Ile  Ser  Asp  Glu  Leu  Asn  Val
               880                     885                     890

AGA  AAT  GTT  GTC  ATC  ACA  TCA  GAC  GAA  GCC  AAG  TAC  TGT  GTT  GAG  TAC    3098
Arg  Asn  Val  Val  Ile  Thr  Ser  Asp  Glu  Ala  Lys  Tyr  Cys  Val  Glu  Tyr
          895                     900                     905

TCG  TGT  GTT  GCT  GAT  TGG  CCA  GTG  TTG  GGT  AAA  AAG  TTA  AAG  TCA  GAC    3146
Ser  Cys  Val  Ala  Asp  Trp  Pro  Val  Leu  Gly  Lys  Lys  Leu  Lys  Ser  Asp
910                     915                     920

GCC  AAA  AAA  GTC  AAG  GCA  GCA  TTG  CCT  AAA  GTT  TCT  TCT  GAA  GAA  GTT    3194
Ala  Lys  Lys  Val  Lys  Ala  Ala  Leu  Pro  Lys  Val  Ser  Ser  Glu  Glu  Val
925                     930                     935                     940

CAA  AGA  TTT  GCC  GAG  TGT  GGT  AAA  ATC  ACT  GTT  GAT  GGT  ATT  GAC  TTG    3242
Gln  Arg  Phe  Ala  Glu  Cys  Gly  Lys  Ile  Thr  Val  Asp  Gly  Ile  Asp  Leu
                    945                     950                     955

GTC  ACT  GAA  GAT  TTG  CAA  GTG  CAA  AGA  GGC  TTG  CCA  GCT  TCT  AAA  GCC    3290
Val  Thr  Glu  Asp  Leu  Gln  Val  Gln  Arg  Gly  Leu  Pro  Ala  Ser  Lys  Ala
               960                     965                     970

GAA  GAG  GGC  CAA  GAG  TTT  AGA  TCT  CAC  CAA  GAT  GTT  TTG  ATT  ATT  TTG    3338
Glu  Glu  Gly  Gln  Glu  Phe  Arg  Ser  His  Gln  Asp  Val  Leu  Ile  Ile  Leu
          975                     980                     985

GAT  GTC  AAT  TTG  CAC  CCT  GAA  TTG  GAA  AGT  GAA  GGT  TTG  GCA  AGA  GAG    3386
Asp  Val  Asn  Leu  His  Pro  Glu  Leu  Glu  Ser  Glu  Gly  Leu  Ala  Arg  Glu
990                     995                     1000

TTG  ATT  AAC  CGT  ATC  CAA  AGA  TTG  CGT  AAA  AAG  GCT  GGT  TTG  AAT  ACC    3434
Leu  Ile  Asn  Arg  Ile  Gln  Arg  Leu  Arg  Lys  Lys  Ala  Gly  Leu  Asn  Thr
1005                    1010                    1015                    1020

ACT  GAC  GAT  GTT  CAA  GTT  CAA  TAC  CGT  GTT  GTC  AAA  GAT  ACT  ATT  GAT    3482
Thr  Asp  Asp  Val  Gln  Val  Gln  Tyr  Arg  Val  Val  Lys  Asp  Thr  Ile  Asp
                    1025                    1030                    1035

TTG  CCA  AAG  GTT  ATT  AAA  GAC  AAT  GAA  GAG  TTG  TTG  TTG  AAA  TCT  ACC    3530
Leu  Pro  Lys  Val  Ile  Lys  Asp  Asn  Glu  Glu  Leu  Leu  Leu  Lys  Ser  Thr
               1040                    1045                    1050

AAA  TAT  CCA  ATT  GAG  GAA  TTG  AAG  GAA  GCA  CAA  GAT  TCT  GCT  AAT  GTC    3578
Lys  Tyr  Pro  Ile  Glu  Glu  Leu  Lys  Glu  Ala  Gln  Asp  Ser  Ala  Asn  Val
          1055                    1060                    1065

ATT  ACC  GAT  GAA  GAG  CAA  ACA  ATC  AAC  GAT  ACA  GTG  TTT  AAT  TTG  CGT    3626
Ile  Thr  Asp  Glu  Glu  Gln  Thr  Ile  Asn  Asp  Thr  Val  Phe  Asn  Leu  Arg
1070                    1075                    1080

TTA  TTA  AAA  ATT       TAGATAGATA   ATTAATACAA   GATTCCCAT   GTACTGATAC        3678
Leu  Leu  Lys  Ile
1085

CAGCGCCTCC  AACCACTGCT  AGTGTTTTGC  TATTTACTGT  AG                                3720
```

(2) INFORMATION FOR SEQ ID NO:23:

(i) SEQUENCE CHARACTERISTICS:
        (A) LENGTH: 1088 amino acids
        (B) TYPE: amino acid
        (D) TOPOLOGY: linear (ii) MOLECULE TYPE: protein (xi) SEQUENCE DESCRIPTION: SEQ ID NO:23:

```
Met  Ser  Leu  Gln  Glu  Ser  Asn  Asn  Asn  Ile  Pro  Gln  Gly  Ala  Phe  Ser
1                   5                   10                      15

Phe  Pro  Lys  Glu  Glu  Glu  Ala  Val  Ile  Lys  His  Trp  Asp  Asp  Val  Asn
```

-continued

```
                     20                        25                        30
Ala  Phe  Gln  Arg  Thr  Leu  Glu  Leu  Thr  Glu  Asp  Leu  Pro  Pro  Phe  Ala
          35                       40                       45

Phe  Phe  Asp  Gly  Pro  Pro  Phe  Ala  Thr  Gly  Thr  Pro  His  Tyr  Gly  His
     50                       55                       60

Ile  Leu  Ala  Ser  Thr  Val  Lys  Asp  Ile  Ile  Pro  Arg  Tyr  Ala  Thr  Met
65                       70                       75                        80

Asn  Gly  Tyr  His  Val  Glu  Arg  Arg  Phe  Gly  Trp  Asp  Thr  His  Gly  Leu
               85                       90                            95

Pro  Val  Glu  His  Glu  Ile  Asp  Lys  Lys  Leu  Asn  Ile  Thr  Ser  Lys  Glu
               100                      105                      110

Asp  Val  Tyr  Ala  Met  Gly  Ile  Asp  Lys  Tyr  Asn  Ala  Glu  Cys  Arg  Ala
          115                      120                      125

Ile  Val  Met  Arg  Tyr  Ala  Asp  Glu  Trp  Arg  Arg  Thr  Ile  Lys  Arg  Leu
     130                      135                      140

Gly  Arg  Trp  Ile  Asp  Met  Asp  Asn  Asp  Tyr  Lys  Thr  Leu  Tyr  Pro  Glu
145                      150                      155                      160

Phe  Met  Glu  Ser  Val  Trp  Trp  Ala  Phe  Lys  Glu  Leu  Phe  Asn  Lys  Asp
                    165                      170                      175

Ala  Val  Tyr  Arg  Gly  Leu  Arg  Val  Met  Pro  Tyr  Ser  Thr  Ala  Cys  Thr
               180                      185                      190

Thr  Pro  Leu  Ser  Asn  Phe  Glu  Ala  Gln  Gln  Asn  Tyr  Lys  Glu  Val  Asn
          195                      200                      205

Asp  Pro  Ala  Leu  Thr  Ile  Ser  Phe  Pro  Leu  Leu  Asp  Asn  Glu  Asp  Thr
     210                      215                      220

Cys  Leu  Val  Ala  Trp  Thr  Thr  Pro  Trp  Thr  Leu  Pro  Ala  Asn  Leu
225                      230                      235                      240

Ala  Leu  Ala  Val  Asn  Pro  Lys  Phe  Glu  Tyr  Val  Lys  Ile  Phe  Asp  Glu
               245                      250                      255

Glu  Lys  Lys  Lys  Asn  Phe  Ile  Leu  Leu  Glu  Ser  Leu  Ile  Ser  Thr  Leu
               260                      265                      270

Tyr  Lys  Lys  Pro  Lys  Ser  Ala  Lys  Phe  Lys  Val  Val  Glu  Lys  Ile  Leu
          275                      280                      285

Gly  Lys  Asp  Leu  Val  Gly  Leu  Lys  Tyr  Lys  Pro  Leu  Phe  Asn  Tyr  Phe
     290                      295                      300

Tyr  Glu  Asp  Phe  Lys  Asp  Thr  Gly  Phe  Arg  Val  Ile  Pro  Ala  Asp  Tyr
305                      310                      315                      320

Val  Thr  Asn  Asp  Ser  Gly  Thr  Gly  Ile  Val  His  Gln  Ala  Pro  Ser  Tyr
                    325                      330                      335

Gly  Glu  Glu  Asp  Phe  Asn  Ser  Thr  Lys  Ala  Ala  Gly  Val  Ile  Asn  Glu
               340                      345                      350

Lys  Lys  Leu  Pro  Pro  Ser  Ile  Val  Asp  Asp  Ser  Gly  Arg  Met  Glu  Ser
               355                      360                      365

Asn  Val  Pro  Glu  Ile  Ala  Gly  Met  Tyr  Phe  Lys  Asp  Ala  Asp  Lys  Val
     370                      375                      380

Ile  Ile  Lys  Lys  Leu  Ser  Glu  Glu  Gly  Arg  Leu  Leu  Val  Asn  Thr  Gln
385                      390                      395                      400

Val  Lys  His  Ser  Tyr  Pro  Phe  Cys  Trp  Arg  Ser  Asp  Thr  Pro  Leu  Met
                    405                      410                      415

Tyr  Arg  Thr  Val  Pro  Ala  Trp  Phe  Val  Arg  Ile  Gly  Glu  Val  Ile  Pro
               420                      425                      430

Glu  Met  Leu  Asp  Asn  Val  Glu  Lys  Thr  Asn  Trp  Val  Pro  Ser  Asn  Ile
               435                      440                      445
```

```
Lys  Asp  Lys  Arg  Phe  Ser  Asn  Trp  Ile  Ala  Asn  Ala  Arg  Asp  Trp  Asn
     450                 455                 460

Ile  Ser  Arg  Asn  Arg  Tyr  Trp  Gly  Thr  Pro  Ile  Pro  Leu  Trp  Val  Ser
465                      470                 475                           480

Asp  Asp  Phe  Glu  Glu  Met  Val  Cys  Val  Gly  Ser  Ile  Gln  Glu  Leu  Arg
                    485                      490                      495

Glu  Leu  Ser  Gly  Arg  Asp  Asp  Ile  Thr  Asp  Ile  His  Arg  Glu  Ser  Ile
               500                      505                      510

Asp  Ser  Ile  Thr  Ile  Pro  Ser  Lys  Gly  Lys  Gly  Gln  Leu  Lys  Arg
               515                 520                      525

Ile  Glu  Glu  Val  Phe  Asp  Cys  Trp  Phe  Glu  Ser  Gly  Ser  Met  Pro  Tyr
          530                 535                      540

Ala  Ser  Lys  His  Tyr  Pro  Phe  Glu  Asn  Glu  Lys  Lys  Phe  Leu  Asp  Ala
545                      550                      555                           560

Phe  Pro  Ala  Asn  Phe  Ile  Ser  Glu  Gly  Leu  Asp  Gln  Thr  Arg  Gly  Trp
                    565                      570                      575

Phe  Tyr  Thr  Leu  Thr  Val  Leu  Gly  Thr  His  Leu  Phe  Lys  Thr  Ala  Pro
               580                      585                      590

Tyr  Gln  Asn  Val  Ile  Val  Thr  Gly  Ile  Val  Leu  Ala  Ala  Asp  Gly  Lys
          595                      600                      605

Lys  Met  Ser  Lys  Arg  Leu  Lys  Asn  Tyr  Pro  Asp  Pro  Thr  Leu  Val  Leu
     610                 615                      620

Glu  Lys  Tyr  Gly  Ala  Asp  Ala  Leu  Arg  Leu  Tyr  Leu  Ile  Asn  Ser  Pro
625                      630                 635                           640

Val  Leu  Arg  Ala  Glu  Thr  Leu  Lys  Phe  Lys  Glu  Glu  Gly  Val  Lys  Glu
                    645                      650                      655

Ile  Val  Ser  Ser  Val  Leu  Leu  Pro  Trp  Tyr  Asn  Ser  Tyr  Lys  Phe  Leu
               660                      665                      670

Lys  Asp  Ala  Ala  Asp  Leu  Phe  Lys  Lys  Asp  Asn  Gly  Lys  Asp  Phe  Val
          675                      680                      685

Tyr  Asp  Ser  Ser  Leu  His  Ser  Thr  Asn  Val  Met  Asp  Arg  Trp  Leu  Leu
     690                 695                      700

Ala  Ser  Ile  Gln  Ser  Leu  Ile  Lys  Phe  Ile  His  Glu  Glu  Met  Thr  Gly
705                      710                 715                           720

Tyr  Arg  Leu  Tyr  Thr  Val  Val  Pro  Arg  Leu  Leu  His  Phe  Ile  Asp  Asp
                    725                      730                      735

Leu  Thr  Asn  Trp  Tyr  Ile  Arg  Phe  Asn  Arg  Arg  Ile  Lys  Gly  Tyr
               740                      745                      750

Ala  Ser  Asp  Asp  Val  Glu  Asp  Thr  Gln  Lys  Gly  Leu  Asn  Thr  Leu  Val
          755                      760                      765

Glu  Ala  Leu  Leu  Thr  Leu  Ser  Arg  Ala  Met  Ala  Pro  Phe  Thr  Pro  Tyr
     770                 775                      780

Leu  Ala  Asp  Gly  Ile  Tyr  Gln  Arg  Ile  Lys  Val  Tyr  Phe  Lys  Gln  Glu
785                      790                      795                           800

Asp  Leu  Glu  Lys  Ile  Ala  Ile  Asn  Pro  Lys  Asn  Val  Asp  Leu  Arg  Ser
                    805                      810                      815

Val  His  Phe  Leu  Ser  Tyr  Pro  Ser  Val  Arg  Gln  Glu  Leu  Phe  Asp  Glu
               820                      825                      830

Lys  Ile  Glu  Val  Ala  Val  Ala  Arg  Met  Gln  Lys  Val  Ile  Asp  Met  Ala
     835                      840                      845

Arg  Asn  Ile  Arg  Glu  Lys  Lys  Met  Ile  Ser  Leu  Lys  Thr  Pro  Leu  Asn
850                      855                      860

Glu  Leu  Val  Val  Leu  Ser  Ala  Asp  Ala  Asp  Leu  Leu  Lys  Asp  Ile  Asp
865                 870                      875                           880
```

| | | | | | | | | | | | | | | |
|---|---|---|---|---|---|---|---|---|---|---|---|---|---|---|
| Ser | Leu | Lys | Gly | Tyr<br>885 | Ile | Ser | Asp | Glu | Leu<br>890 | Asn | Val | Arg | Asn | Val  Val<br>895 |
| Ile | Thr | Ser | Asp<br>900 | Glu | Ala | Lys | Tyr | Cys<br>905 | Val | Glu | Tyr | Ser | Cys<br>910 | Val  Ala |
| Asp | Trp | Pro<br>915 | Val | Leu | Gly | Lys | Lys<br>920 | Leu | Lys | Ser | Asp | Ala<br>925 | Lys | Lys  Val |
| Lys | Ala<br>930 | Ala | Leu | Pro | Lys | Val<br>935 | Ser | Ser | Glu | Glu | Val<br>940 | Gln | Arg | Phe  Ala |
| Glu<br>945 | Cys | Gly | Lys | Ile | Thr<br>950 | Val | Asp | Gly | Ile | Asp<br>955 | Leu | Val | Thr | Glu  Asp<br>960 |
| Leu | Gln | Val | Gln | Arg<br>965 | Gly | Leu | Pro | Ala | Ser<br>970 | Lys | Ala | Glu | Glu | Gly  Gln<br>975 |
| Glu | Phe | Arg | Ser<br>980 | His | Gln | Asp | Val | Leu<br>985 | Ile | Ile | Leu | Asp | Val<br>990 | Asn  Leu |
| His | Pro | Glu<br>995 | Leu | Glu | Ser | Glu | Gly<br>1000 | Leu | Ala | Arg | Glu | Leu<br>1005 | Ile | Asn  Arg |
| Ile | Gln<br>1010 | Arg | Leu | Arg | Lys | Lys<br>1015 | Ala | Gly | Leu | Asn | Thr<br>1020 | Thr | Asp | Asp  Val |
| Gln  Val<br>1025 | Gln | Tyr | Arg | Val<br>1030 | Val | Lys | Asp | Thr | Ile<br>1035 | Asp | Leu | Pro | Lys | Val<br>1040 |
| Ile | Lys | Asp | Asn | Glu<br>1045 | Glu | Leu | Leu | Leu | Lys<br>1050 | Ser | Thr | Lys | Tyr | Pro  Ile<br>1055 |
| Glu | Glu | Leu | Lys<br>1060 | Glu | Ala | Gln | Asp | Ser<br>1065 | Ala | Asn | Val | Ile | Thr<br>1070 | Asp  Glu |
| Glu  Gln | Thr<br>1075 | Ile | Asn | Asp | Thr | Val<br>1080 | Phe | Asn | Leu | Arg | Leu<br>1085 | Leu | Lys | Ile |

What is claimed is:

1. An isolated nucleic acid which encodes a Candida isoleucyl-tRNA synthetase.

2. The isolated nucleic acid of claim 1, wherein the isoleucyl-tRNA synthetase is a *Candida albicans* isoleucyl-tRNA synthetase.

3. Isolated nucleic acid which encodes isoleucyl-tRNA synthetase having the amino acid sequence of an isoleucyl-tRNA synthetase isolated from a species of Candida, said nucleic acid hybridizing under high stringency conditions to DNA having the sequence SEQ ID NO:1 or SEQ ID NO:22.

4. Isolated nucleic acid having the sequence of a nucleic acid isolated from a species of Candida and encoding an isoleucyl-tRNA synthetase, which hybridizes under high stringency conditions to DNA having the sequence SEQ ID NO:1 or SEQ ID NO:22.

5. Isolated nucleic acid having the sequence of a nucleic acid isolated from a species of Candida, encoding an isoleucyl-tRNA synthetase which shares at least about 95% percent amino acid sequence similarity with a Candida isoleucyl-tRNA synthetase encoded by SEQ ID NO:1.

6. An essentially pure nucleic acid which hybridizes under very high stringency conditions to DNA having SEQ ID NO:1 or to an RNA counterpart of SEQ ID NO:1, and encodes at least a functional portion of a Candida isoleucyl-tRNA synthetase, said portion having catalytic activity or binding function.

7. An essentially pure nucleic acid of claim 6 wherein the isoleucyl-tRNA synthetase is a *Candida albicans* isoleucyl-tRNA synthetase.

8. An essentially pure nucleic acid which encodes the amino acid sequence SEQ ID NO:2.

9. An essentially pure nucleic acid which encodes the amino acid sequence SEQ ID NO:23.

10. An isolated nucleic acid vector comprising a nucleic acid which encodes a Candida isoleucyl-tRNA synthetase.

11. An isolated nucleic acid vector of claim 10 wherein the isoleucyl-tRNA synthetase is a *Candida albicans* isoleucyl-tRNA synthetase.

12. An isolated nucleic acid vector comprising a nucleic acid which encodes at least a functional portion of a Candida isoleucyl-tRNA synthetase, and which hybridizes to DNA having the sequence SEQ ID NO:1 under very high stringency conditions, said portion having catalytic activity or binding function.

13. An isolated nucleic acid vector comprising isolated nucleic acid having the sequence of a nucleic acid isolated from a species of Candida and encoding an isoleucyl-tRNA synthetase, which nucleic acid hybridizes under high stringency conditions to DNA having the sequence SEQ ID NO:1 or SEQ ID NO:22.

14. An isolated nucleic acid vector comprising nucleic acid which encodes isoleucyl-tRNA synthetase having the amino acid sequence of an isoleucyl-tRNA synthetase isolated from a species of Candida, said nucleic acid hybridizing under high stringency conditions to DNA having the sequence SEQ ID NO:1.

15. A host cell comprising a recombinant nucleic acid which encodes a Candida isoleucyl-tRNA synthetase.

16. A host cell of claim 15 wherein the Candida isoleucyl-tRNA synthetase is a *Candida albicans* isoleucyl-tRNA synthetase.

17. A host cell comprising a recombinant Candida isoleucyl-tRNA synthetase gene which expresses a Candida isoleucyl-tRNA synthetase or a functional portion thereof, said portion having catalytic activity or binding function.

18. A host cell of claim 17 in which the recombinant Candida isoleucyl-tRNA synthetase gene expresses a *Candida albicans* isoleucyl-tRNA synthetase or a functional portion thereof, said portion having catalytic activity or binding function.

19. A host cell comprising isolated nucleic acid having the sequence of a nucleic acid isolated from a species of Candida and encoding an isoleucyl-tRNA synthetase, which nucleic acid hybridizes under high stringency conditions to DNA having the sequence SEQ ID NO:1 or SEQ ID NO:22.

20. An expression vector comprising a nucleic acid encoding a fusion protein comprising a Candida isoleucyl-tRNA synthetase or functional portion thereof having catalytic activity or binding function, wherein said nucleic acid comprises all or part of the coding sequence for a Candida isoleucyl-tRNA synthetase, and wherein the coding sequence is operably linked to one or more expression control sequences.

21. A tester strain comprising a suitable host cell, said host cell comprising a heterologous Candida isoleucyl-tRNA synthetase gene encoding an isoleucyl-tRNA synthetase or portion thereof having catalytic activity or binding function, wherein the gene complements a defect in a host gene encoding isoleucyl-tRNA synthetase.

22. The tester strain of claim 21 in which a host gene encoding an isoleucyl-tRNA synthetase has been lost or has been altered relative to wild type so as to make no gene product, a gene product which is inactive, or a gene product which can be conditionally made inactive.

23. The tester strain of claim 21 in which the host cells are of a genus other than Candida.

24. The tester strain of claim 21 in which the Candida isoleucyl-tRNA synthetase gene encoding an isoleucyl-tRNA synthetase or portion thereof is a *Candida albicans* isoleucyl-tRNA synthetase gene.

25. A method for producing active Candida isoleucyl-tRNA synthetase or a functional portion thereof comprising:
   a) constructing a recombinant nucleic acid vector comprising a coding sequence for Candida isoleucyl-tRNA synthetase or a portion thereof having catalytic activity or binding function, wherein the coding sequence is under the control of transcription signals and is linked to appropriate translation signals;
   b) introducing the vector into suitable host cells which support the replication of the vector; and
   c) maintaining the host cells under conditions in which Candida isoleucyl-tRNA synthetase is expressed.

26. A method for producing active Candida isoleucyl-tRNA synthetase or a functional portion thereof comprising the steps of introducing a recombinant nucleic acid vector comprising a coding sequence for a Candida isoleucyl-tRNA synthetase or a portion thereof having catalytic activity or binding function, into suitable host cells, and maintaining the host cells under conditions in which the gene is expressed.

27. A method for producing a Candida isoleucyl-tRNA synthetase or a functional portion thereof comprising maintaining a host cell containing a recombinant nucleic acid encoding a Candida isoleucyl-tRNA synthetase or a functional portion thereof having catalytic activity or binding function under conditions suitable for expression of the nucleic acid, whereby the encoded Candida isoleucyl-tRNA synthetase or functional portion thereof is expressed and thereby produced.

28. The method of claim 27 further comprising the step of isolating the Candida isoleucyl-tRNA synthetase or functional portion thereof.

29. The method of claim 28 wherein the Candida isoleucyl-tRNA synthetase is a *Candida albicans* isoleucyl-tRNA synthetase.

30. The tester strain of claim 24 wherein the host cell is *Saccharomyces cerevisiae* and the host gene is ILS1.

31. Isolated nucleic acid encoding a polypeptide comprising an amino acid sequence selected from the group consisting of SEQ ID NO:2, SEQ ID NO:23, and portions thereof having catalytic activity or binding function.

32. Isolated nucleic acid encoding a polypeptide comprising a Candida isoleucyl-tRNA synthetase or portion thereof having catalytic or binding function.

33. Isolated nucleic acid encoding a polypeptide comprising a *Candida albicans* isoleucyl-tRNA synthetase or portion thereof having catalytic or binding function.

34. A host cell comprising a recombinant nucleic acid encoding a polypeptide comprising a Candida isoleucyl-tRNA synthetase or portion thereof having catalytic activity or binding function.

35. A method for producing a polypeptide comprising a Candida isoleucyl-tRNA synthetase or portion thereof having catalytic activity or binding function comprising maintaining a host cell of claim 34 under conditions suitable for expression of the nucleic acid, whereby the polypeptide is expressed and thereby produced.

36. The method of claim 35 further comprising isolating the polypeptide.

37. A host cell comprising a recombinant nucleic acid encoding a polypeptide comprising a *Candida albicans* isoleucyl-tRNA synthetase or portion thereof having catalytic activity or binding function, wherein said nucleic acid hybridizes under high stringency conditions to DNA having SEQ ID NO:1.

38. A method for producing a polypeptide comprising a *Candida albicans* isoleucyl-tRNA synthetase or portion thereof having catalytic activity or binding function comprising maintaining a host cell of claim 37 under conditions suitable for expression of the nucleic acid, whereby the polypeptide is expressed and thereby produced.

39. The method of claim 38 further comprising isolating the polypeptide.

40. An isolated nucleic acid, wherein said nucleic acid encodes a polypeptide comprising an isoleucyl-tRNA synthetase or portion thereof which is encoded by pC$^3$410 as deposited under ATCC Accession No. 98564, wherein said isoleucyl-tRNA synthetase or portion thereof has catalytic activity or binding function.

41. The isolated nucleic acid of claim 40, wherein the polypeptide is a fusion protein.

42. An isolated nucleic acid, wherein said nucleic acid encodes a polypeptide comprising an isoleucyl-tRNA synthetase which is encoded by a derivative of pC$^3$410 as pC$^3$410 was deposited under ATCC Accession No. 98564, in which CTG at codon position 390 is altered to TCT and CTG at codon position 1065 is altered to TCT.

43. A nucleic acid vector comprising a nucleic acid which encodes a polypeptide comprising an isoleucyl-tRNA synthetase or portion thereof which is encoded by pC$^3$410 as deposited under ATCC Accession No. 98564, wherein said isoleucyl-tRNA synthetase or portion thereof has catalytic activity or binding function.

44. A nucleic acid vector comprising a nucleic acid, wherein said nucleic acid encodes a polypeptide comprising an isoleucyl-tRNA synthetase which is encoded by a derivative of pC$^3$410 as pC$^3$410 was deposited under ATCC Accession No. 98564, in which CTG at codon position 390 is altered to TCT and CTG at codon position 1065 is altered to TCT.

45. A host cell comprising a recombinant nucleic acid, wherein said nucleic acid encodes a polypeptide comprising an isoleucyl-tRNA synthetase or portion thereof which is encoded by pC$^3$410 as deposited under ATCC Accession No. 98564, wherein said isoleucyl-tRNA synthetase or portion thereof has catalytic activity or binding function.

46. A method for producing a polypeptide comprising an isoleucyl-tRNA synthetase or portion thereof, comprising maintaining a host cell of claim 45 under conditions suitable for expression of said polypeptide, whereby said polypeptide is produced.

47. The method of claim 46 further comprising isolating the polypeptide.

48. A host cell comprising a recombinant nucleic acid, wherein said nucleic acid encodes a polypeptide comprising an isoleucyl-tRNA synthetase which is encoded by a derivative of pC$^3$410 as pC$^3$410 was deposited under ATCC Accession No. 98564, in which CTG at codon position 390 is altered to TCT and CTG at codon position 1065 is altered to TCT.

49. A method for producing a polypeptide comprising an isoleucyl-tRNA synthetase or portion thereof, comprising maintaining a host cell of claim 48 under conditions suitable for expression of said polypeptide, whereby said polypeptide is produced.

50. The method of claim 49 further comprising isolating the polypeptide.

51. Plasmid pC$^3$410 as deposited under ATCC Accession No. 98564.

* * * * *